(12) United States Patent
Prohens López et al.

(10) Patent No.: US 11,591,363 B2
(45) Date of Patent: Feb. 28, 2023

(54) CRYSTALLINE FORMS OF BETA-SITOSTEROL

(71) Applicants: CENTER FOR INTELLIGENT RESEARCH IN CRYSTAL ENGINEERING, S.L., Palma de Mallorca (ES); ALIMENTOMICA, S.L., Campanet (ES)

(72) Inventors: Rafel Prohens López, Sabadell (ES); Rafael Barbas Cañero, Santa Coloma de Gramenet (ES); Anna Portell Bueso, Sabadell (ES); Mariona Palou March, Portocolom (ES); Francisca Serra Vich, Llucmajor (ES); Andreu Palou March, Palmañola (ES)

(73) Assignees: CENTER FOR INTELLIGENT RESEARCH IN CRYSTAL ENGINEERING, S.L., Palma de Mallorca (ES); ALIMENTOMICA, S.L., Campanet (ES)

( * ) Notice: Subject to any disclaimer, the term of this patent is extended or adjusted under 35 U.S.C. 154(b) by 174 days.

(21) Appl. No.: 16/624,842

(22) PCT Filed: Jun. 22, 2018

(86) PCT No.: PCT/EP2018/066745
§ 371 (c)(1),
(2) Date: Dec. 19, 2019

(87) PCT Pub. No.: WO2018/234540
PCT Pub. Date: Dec. 27, 2018

(65) Prior Publication Data
US 2020/0207801 A1 Jul. 2, 2020

(30) Foreign Application Priority Data
Jun. 22, 2017 (EP) .................................... 17382390

(51) Int. Cl.
*A61K 31/56* (2006.01)
*C07J 9/00* (2006.01)

(52) U.S. Cl.
CPC ............. *C07J 9/00* (2013.01); *C07B 2200/13* (2013.01)

(58) Field of Classification Search
CPC .................................. C07J 9/00; A61K 31/56
See application file for complete search history.

(56) References Cited

PUBLICATIONS

Cowins et al, J Incl Phenom Macrocycl Chem (2015), vol. 83, pp. 141-148. (Year: 2015).*

(Continued)

*Primary Examiner* — Craig D Ricci
*Assistant Examiner* — Janet L Coppins
(74) *Attorney, Agent, or Firm* — Squire Patton Boggs (US) LLP

(57) ABSTRACT

The present invention relates to a cocrystal of beta-sitosterol or a pharmaceutically acceptable ester thereof or an edible acceptable ester thereof and an organic carboxylic acid coformer, an hydrate crystal form of beta-sitosterol having 1.25 molecules of water per molecule of beta-sitosterol and a combination that comprises a cocrystal of beta-sitosterol and an organic carboxylic acid; and the hydrate crystal form of beta-sitosterol having 1.25 molecules of water per molecule of beta-sitosterol. It also relates to processes for their preparation, and compositions containing them, as well as their use as a medicament or dietary supplement or functional food, and in particular in the prophylaxis and/or treatment of a disease or conditions that involves an alteration of lipid metabolism, circulating levels of lipids in the blood and/or lipid composition in tissues and organs.

8 Claims, 42 Drawing Sheets

(56) References Cited

PUBLICATIONS

Toda et al, Bull Chem Soc Japan 1993, vol. 66 (1), pp. 320-323. (Year: 1993).*

International Search Report and Written Opinion dated Nov. 22, 2018 for PCT Application No. PCT/EP2018/066745, 24 pages.

Andrade, et al: "Advances in analytical methods to study cholesterol metabolism: the determination of serum noncholesterol sterols", Biomedical Chromatography 2013, vol. 27, No. 10, pp. 1234-1242 (published online Nov. 20, 2012).

Argay, et al: "Crystal structure of stigmast-5-en-3β-ol monohydrate, C29H52O2", Zeitschrift für Kristallographie Jan. 1, 1996, vol. 211, No. 10, pp. 725-727. XP55415864A.

Bernal, et al: "X-Ray Crystallography and the Chemistry of the Steroids Part I", Royal Society of London Philosophical Transactions, Mathematical, Physical and Engineering Sciences, Dec. 31, 1940; vol. 239, No. 802, pp. 135-182. XP55416003A.

Christiansen, et al: "Effect of beta-sitosterol on precipitation of cholesterol from non-aqueous and aqueous solutions", International Journal of Pharmaceutics, 2003, vol. 254, pp. 155-166.

Christiansen, et al: "A novel method of producing a microcrystalline beta-sitosterol suspension in oil", European Journal of Pharmaceutical Sciences Apr. 1, 2002, vol. 15, pp. 261-269. XP009140869A.

Cowins, et al: "Preparation and characterization of [beta]-sitosterol/[beta]-cyclodextrin crystalline inclusion complexes", Journal of Inclusion Phenomena and Macrocyclic Chemistry Kluwer Jul. 30, 2015: vol. 83, No. 1, pp. 141-148. XP35542854.

Garcia-Llatas, et al: "Simultaneous quantification of serum phytosterols and cholesterol precursors using a simple gas chromatographic method", European Journal of Lipid Science and Technology, 2012, vol. 114, No. 5, pp. 520-526.

Meng, et al: "Preparation and properties of phytosterols with hydroxypropyl [beta]-cyclodextrin inclusion complexes", European Food Research and Technology Zeitschrift Für Lebensmitteluntersuchung Und-Forschung A, Springer, Berlin, DE, Sep. 28, 2012; vol. 235, No. 6, pp. 1039-1047. XP35142097.

Moreno-Calvo, et al: "A New Microcrystalline Phytosterol Polymorph Generated Using CO2-Expanded Solvents", Crystal Growth & Design 2014, vol. 14, pp. 58-68.

Reagan-Shaw, et al: "Dose translation from animal to human studies revisited", FASEB Journal 2007, vol. 22, pp. 659-661.

Toda, et al: "Inclusion Complexation Of Cholestanol, Cholesterol, Sitosterol, Stigmasterol, And Ergosterol With Various Guest Compounds", Bulletin Of The Chemical Society Of Japan, Chemical Society Of Japan, Jan. 1, 1993; vol. 66, No. 1, pp. 320-323. XP345424A.

Von Bonsdorff-Nikander, et al: "Physical changes of beta-sitosterol crystals in oily suspensions during heating" AAPS PharmSciTech, Oct. 19, 2005, vol. 6, No. 3, Article 51, pp. E413-E420.

* cited by examiner

1A

1B

CRYSTALLINE FORMS OF BETA-SITOSTEROL

CROSS-REFERENCE

The present application is a national-phase filing of International Application No. PCT/EP2018/066745 (filed Jun. 22, 2018) under 35 U.S.C. § 371, which claims the benefit of and priority to European Patent Application No. EP 17382390.7 (filed on Jun. 22, 2017).

This application claims the benefit of European Patent Application EP17382390.7 filed on Jun. 22, 2017.

The present invention relates to crystals of beta-sitosterol or a pharmaceutically acceptable ester thereof or an edible acceptable ester thereof, processes for their preparation, and compositions comprising them. It also relates to their use as a medicament, dietary supplement or functional food.

BACKGROUND ART

Arteriosclerosis is the thickening, hardening and loss of elasticity of the walls of arteries. This process gradually restricts the blood flow to one's organs and tissues and can lead to severe health risks brought on by atherosclerosis. Atherosclerosis (also known as arteriosclerotic vascular disease or ASVD) is a specific form of arteriosclerosis caused by the build-up of an atheroma in and on the artery walls. The atheroma is an accumulation of degenerative material in the inner layer of an artery wall. The degenerative material forming the atheroma consists of mostly macrophage cells, lipids (fatty compounds), and fibrous connective tissue.

Although the precise significance of an elevation of one or more specific blood lipid fractions is not known, there have been disclosed sufficient evidences that elevated serum cholesterol levels (also known as hypercholesterolemia) were considered to be the most important factor in the ethiology of the atherosclerotic process. Therefore, intensive efforts have been made to find an effective pharmacologic agent that reduces the serum cholesterol levels. High levels of cholesterol in blood and in particular high levels of cholesterol-LDL and also to considerable extend high ratio of cholesterol-LDL to cholesterol-HDL are considered risk factors for arteriosclerosis, atherosclerosis and other alterations and diseases of the blood vessels and cardiovascular system.

Phytosterols (plant sterols) are plant steroids (or phytosteroids), which encompass both plant sterols and plants stanols (phytostanols) are compounds that have a structure similar to cholesterol. In particular, their structures vary only in the carbon side chains and/or the presence or absence of a double bond (e.g. sitosterol and sitostanol). Phytosterols are widely distributed in the plant kingdom and specially found in vegetable oil, and avocados. However, they are not synthesized by the human body and therefore their presence in the body is the result of their consumption as part of the diet.

Particularly, the β-Sitosterol (or beta-sitosterol) is the International Nonproprietary Name (INN) of (17-(5-ethyl-6-methylheptan-2-yl)-10,13-dimethyl-2,3,4,7,8,9,11,12,14,15,16,17-dodecahydro-1H-cyclopenta[a]phenanthren-3-ol. It is the phytosterol more abundant in current diets and in many phytosterol-based functional foods or food supplements. The structure of the beta-sitosterol corresponds to the formula (I):

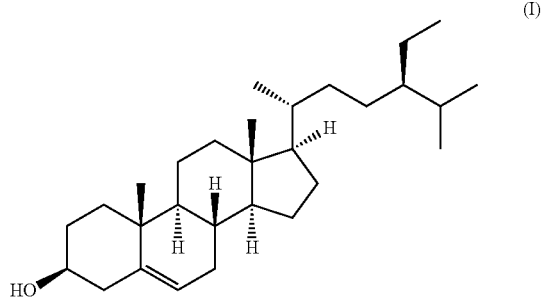

(I)

Several clinical studies disclosed in the state of the art have demonstrated that phytosterols reduce serum cholesterol levels by inhibiting cholesterol absorption in the intestinal lumen and probably by other less known mechanisms. Particularly, beta-sitosterol is useful for the reduction of serum total and LDL-cholesterol levels because the beta-sitosterol competes with cholesterol for up taking the cholesterol by the cells or by interfering with the esterification of cholesterol. In fact, beta-sitosterol has been approved by the FDA (Food and drug Administration) for that indication.

In addition, regarding arteriosclerosis there is also increasing emphasis in other lipid entities such as triglycerides. Therefore, intensive efforts have been and are being made to find pharmacologic agents that possess hypolipemic properties with varying degrees of effectiveness and specificity to the different lipid fractions.

It is known that different solid forms of an active ingredient can have different characteristics, and offer certain advantages, for example with regard to solubility or bioavailability. Thus, the discovery of new solid forms allows for improving the pharmacokinetic and/or pharmacologic or other physicochemical properties of the active ingredients and as a consequence, the characteristics of the pharmaceutical formulations containing the active ingredients, since some forms are more adequate for one type of formulation, and other forms for other different formulations.

Particularly, in recent years cocrystal formation has emerged as a viable strategy towards improving the pharmacokinetic data of active ingredients. By cocrystalizing an active ingredient or a salt of an active ingredient with at least one coformer (the second component of the cocrystal), a new solid state form of the active ingredient is created having unique properties compared with existing solid forms of the active ingredient or its salts. However, cocrystal formation is not predictable, and in fact is not always possible. Moreover, there is no way to predict the properties of a particular cocrystal of a compound until it is formed. Finding the appropriate coformers and right conditions to obtain a particular cocrystal can take significant time, effort and resources.

Monohydrate and hemihydrate forms of beta-sitosterol have been disclosed in the state of the art. In particular, a monohydrate form of beta-sitosterol was obtained by crystallization of the beta-sitosterol in a mixture of acetone and water, then the corresponding hemihydrate was obtained by submitting the monohydrate in dry atmosphere conditions (cf. Leena I. Christiansen et al. "A novel method of producing a microcrystalline beta-sitosterol suspension in oil" European Journal of Pharmaceutical Sciences, 2002, vol. 15, pp. 261-269). Furthermore, other monohydrate and hemihydrate forms of beta-sitosterol have been obtained by crystallization of beta-sitosterol with polysorbate 80 (cf. L. Christiansen et al. "Effect of beta-sitosterol on precipitation of cholesterol from non-aqueous and aqueous solutions", International Journal of Pharmaceutics, 2003, vol. 254, pp. 155-166). Finally, further monohydrate and hemihydrate forms have been also obtained by crystallization of the beta-sitosterol in oil-suspensions (cf. Anna von Bonsdorff-Nikander et al. "Physical changes of beta-sitosterol crystals in oily suspensions during heating" AAPS Pharm. Sci. Tech. 2005, vol 6(3) article 51). All the above mentioned hydrate and hemihydrate forms of beta-sitosterol have been characterized by X-ray powder diffraction (XRPD).

From what is known in the art, there is still the need of finding new pharmacologic agents that possess hypolipemic properties with varying degrees of effectiveness and specificity to the different lipid fractions.

SUMMARY OF INVENTION

The inventors have found that beta-sitosterol or a pharmaceutically acceptable ester thereof or an edible acceptable ester thereof can form cocrystal with an organic carboxylic acid coformer as a hydrogen bond donor coformer. These cocrystals have a high pharmacological activity, for instance contributes to the reduction of high blood lipid levels and/or maintenance of normal plasma or blood lipid levels, including specific fractions of blood cholesterol and of blood triglycerides or triacylglycerols. The provision of cocrystals of beta-sitosterol or a pharmaceutically acceptable ester thereof or an edible acceptable ester thereof gives a new tool to overcome the problems associated with the normalization or maintenance of lipid levels in blood because the inventors have found that such cocrystals of the invention are much more effective and selective at lowering determinate lipid fractions of circulating lipid levels.

On one hand, the inventors have found that cocrystals of beta-sitosterol or a pharmaceutically acceptable ester thereof or an edible acceptable ester thereof having an organic carboxylic acid as a hydrogen bond donor coformer are much more effective and selective at lowering circulating cholesterol levels than the known anhydrous form, the monohydrate form and the hemihydrate form as described in the state of the art.

On the other hand, the inventors have also found that cocrystals of beta-sitosterol or a pharmaceutically acceptable ester thereof or an edible acceptable ester thereof having an organic alcohol as a hydrogen bond donor coformer are much more effective and selective at lowering circulating triglyceride levels than the known anhydrous form, the monohydrate form and the hemihydrate form.

Inventors have also found a hydrate crystal form of beta-sitosterol or a pharmaceutically acceptable ester thereof or an edible acceptable ester thereof that has 1.25 molecules of water per molecule of beta-sitosterol and which is effective and selective at lowering circulating triglyceride levels.

Advantageously, a combination of a cocrystal of beta-sitosterol or a pharmaceutically acceptable ester thereof or an edible acceptable ester thereof and an organic carboxylic acid, with a cocrystal of beta-sitosterol and an organic alcohol, or alternatively with an hydrate crystal form of beta-sitosterol or a pharmaceutically acceptable ester thereof or an edible acceptable ester thereof having 1.25 molecules of water per molecule of beta-sitosterol is much more effective at lowering circulating lipid levels. In particular, this combination is especially advantageous because allows lowering both the levels of cholesterol and triglycerides in blood.

Furthermore, this combination is also advantageous because allows administering both active ingredients separately, sequentially or simultaneously, provided that such administration comprises separate compositions of the two active ingredients.

Therefore, the crystals of the present invention allows designing a personalized treatment (precision medicine or precision nutrition) of the abnormal serum lipid levels based on the specific conditions of the disease or condition that involves the alteration of lipid metabolism, circulating levels of lipids in the blood and/or lipid composition in tissues and organs and also the specific characteristics of the patient to be treated, including its genomic characteristics.

Thus, a first aspect of the invention relates to a cocrystal of beta-sitosterol or a pharmaceutically acceptable ester thereof or an edible acceptable ester thereof and an organic carboxylic acid coformer.

A second aspect of the invention relates to a hydrate crystal form of beta-sitosterol or a pharmaceutically acceptable ester thereof or an edible acceptable ester thereof having 1.25 molecules of water per molecule of beta-sitosterol.

A third aspect of the invention relates to a combination comprising a cocrystal of beta-sitosterol or a pharmaceutically acceptable ester thereof or an edible acceptable ester thereof and an organic carboxylic acid; and a crystal of beta-sitosterol selected from the group consisting of a cocrystal of beta-sitosterol or a pharmaceutically acceptable ester thereof or an edible acceptable ester thereof and an organic alcohol or alternatively a hydrate crystal form of beta-sitosterol or a pharmaceutically acceptable ester thereof or an edible acceptable ester thereof having 1.25 molecules of water per molecule of beta-sitosterol.

A fourth aspect of the invention relates to a composition comprising an effective amount of either a) a cocrystal of beta-sitosterol or a pharmaceutically acceptable ester thereof or an edible acceptable ester thereof and an organic carboxylic acid coformer; or a hydrate crystal form of beta-sitosterol or a pharmaceutically acceptable ester thereof or an edible acceptable ester thereof that has 1.25 molecules of water per molecule of beta-sitosterol; or a combination comprising a cocrystal of beta-sitosterol or a pharmaceutically acceptable ester thereof or an edible acceptable ester thereof and an organic carboxylic acid; and a crystal of beta-sitosterol or a pharmaceutically acceptable ester thereof or an edible acceptable ester thereof selected from the group consisting of a cocrystal of beta-sitosterol and an organic alcohol and a hydrate crystal form of beta-sitosterol or a pharmaceutically acceptable ester thereof or an edible acceptable ester thereof having 1.25 molecules of water per molecule of beta-sitosterol, together with one or more appropriate acceptable excipients or carriers.

A fifth aspect of the invention relates to a cocrystal of beta-sitosterol as defined above; a hydrate crystal form of beta-sitosterol as defined above, or alternatively, a combination as defined above for use as a medicament.

A composition as defined above for use as a medicament is also part of the invention.

And, the sixth aspect of the invention relates to a cocrystal of beta-sitosterol as defined above; a hydrate crystal form of beta-sitosterol as defined above, or alternatively, a combination as defined above, for use in the prophylaxis and/or treatment of a disease or condition which involves an alteration of lipid metabolism, circulating levels of lipids in the blood and/or lipid composition in tissues and organs.

A composition as defined above for use in the prophylaxis and/or treatment of a disease or condition which involves an alteration of lipid metabolism, circulating levels of lipids in the blood and/or lipid composition in tissues and organs is also part of the invention.

DETAILED DESCRIPTION OF THE INVENTION

Figure 1:
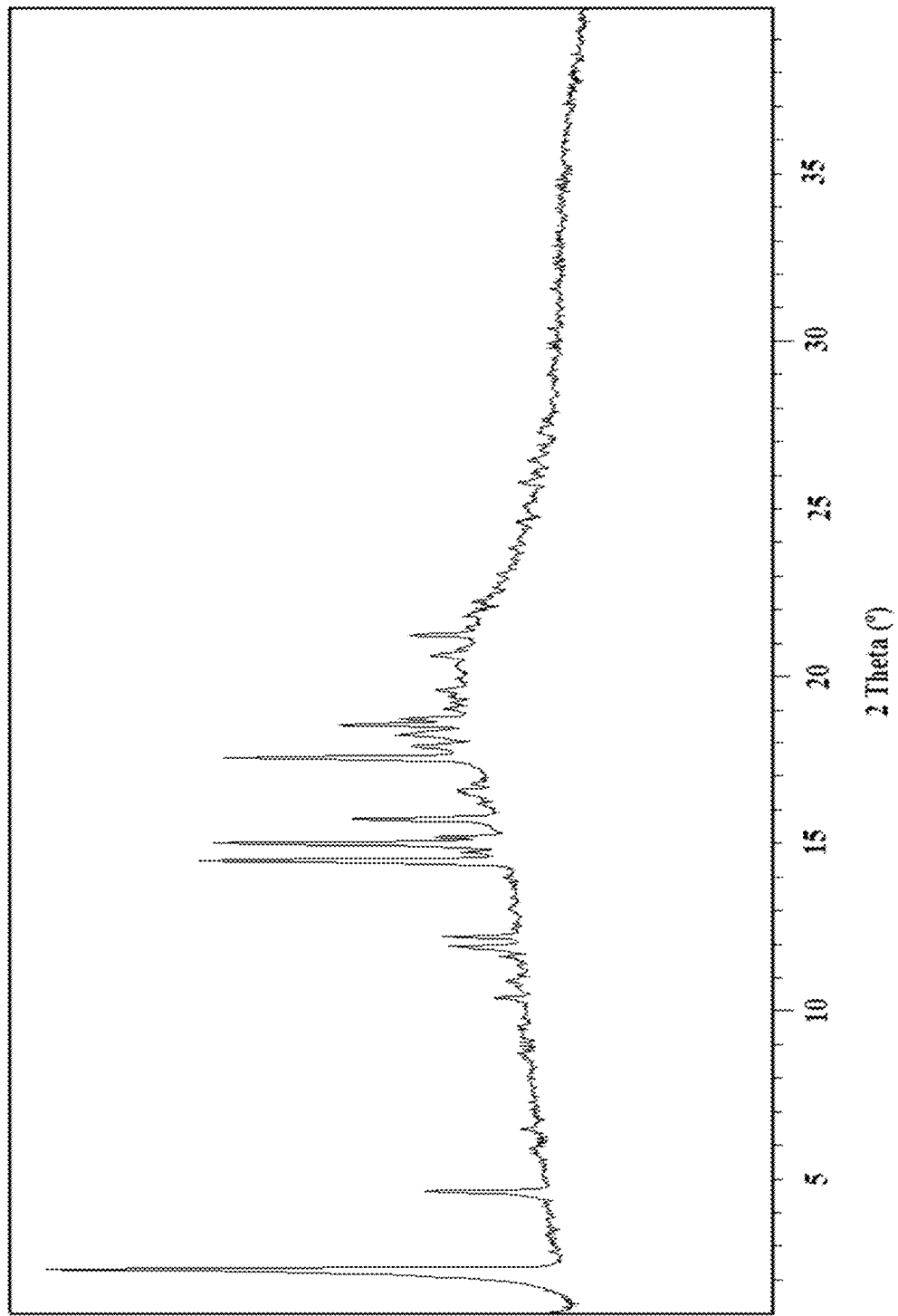
FIG. 1 shows the X-ray powder diffractogram (XRPD) of the cocrystal of beta-sitosterol and L-lactic acid of the present invention. The spectrum expresses intensity (I; counts) versus degrees 2 theta (°).

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper end-points of the range. Ranges given, such as temperatures, times, ratios of cocrystal components and the like, should be considered approximate, unless specifically stated.

For the purposes of the invention, the term "cocrystal" refers herein to a crystalline entity with at least two different components constituting the unit cell at room temperature (20-25° C.) and interacting by weak interactions. Thus, in a cocrystal, one component crystallizes with one or more neutral components. The cocrystals may include one or more solvent molecules in the crystal lattice. Thus, the term "cocrystal hydrate" or "hydrate cocrystal" have the same meaning and are used interchangeable. They refer to a cocrystal including water as a solvent in the crystal lattice.

The expression "cocrystal obtainable by" is used here to define each specific cocrystal of the invention by the process for obtaining it and refers to the product obtainable by any of the corresponding processes disclosed herein. For the purposes of the invention the expressions "obtainable", "obtained" and equivalent expressions are used interchangeably and, in any case, the expression "obtainable" encompasses the expression "obtained".

The terms "percentage (%) by volume" or "volume/volume %" or "v/v %" have the same meaning and are used interchangeable. They refer to the amount of a solute in relation to the total solution volume.

When values of characteristic peaks of an X-ray diffractogram are given it is said that these are "approximate" values. It should be understood that the values are the ones shown in the corresponding lists or tables ±0.3 degrees 2 theta measured in an X-ray diffractometer with Cu—K$_\alpha$ radiation λ=1.5406 Å.

When a ratio of components of the cocrystals of the invention is specified it refers to the molar ratio between the components that forms the cocrystal. The term "molar ratio" has been used to express the stoichiometric amount in mols of each of the components of a cocrystal. The molar ratio can be determined by $^1$H NMR (Proton nuclear magnetic resonance), thermogravimetric analysis (TGA) or single crystal X-ray diffraction (SCXRD). When values of molar ratio are given according to NMR or TGA it is said that these are "approximate" values due to the measurement error. It should be understood that when a molar ratio is mentioned, it corresponds to a molar ratio ±0.2%. The variability of the results is due to the inherent sensibility of the $^1$H NMR and the TGA equipment.

The term "slurring" as disclosed herein refers to any process, which employs a solvent to wash or disperse by stirring a suspension of a compound.

The term "room temperature" refers to a temperature of the environment, without heating or cooling, and it is generally comprised from 20° C. to 25° C.

The term "overnight" refers to a time interval comprised from 10 h to 20 h.

The term "one day" refers to a time interval comprised from 20 h to 28 h.

The term "miscible organic solvent" refers to an organic solvent that, when combined, form a single phase, which means that the mixture thus obtained is "monophasic" under specified conditions of component concentrations and temperature among others. Further, the term "water-miscible organic solvent" refers to an organic solvent that can form a monophasic solution with water at the temperature at which the reaction is carried out. As used herein, the term "monophasic" refers to a reaction medium that includes only one liquid phase, and also a method employing such a reaction medium. Some examples of monophasic mediums are water, aqueous solutions, and solutions containing aqueous and organic solvents that are miscible with each other.

The term "immiscible organic solvent" refers to an organic solvent that, when combined, form two phases, which means that the mixture thus obtained is "biphasic" under specified conditions of component concentrations and temperature among others. Further, the term "water-immiscible organic solvent" refers to an organic solvent that can form a biphasic phase with water at the temperature at which the reaction is carried out. As used herein, the term "biphasic" refers to a reaction medium that includes two immiscible liquid phases, for example, an aqueous phase and a water-immiscible organic solvent phase. The term "biphasic" can also be used to describe a method employing such a reaction medium.

The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl.

The term "($C_6$-$C_{12}$)aryl" refers to an aromatic known ring system comprising one or more rings and from 6 to 12 ring members, wherein all the ring members comprise carbon atoms. Examples of ($C_6$-$C_{12}$)aryl include phenyl and naphthalene. The term "known ring system" as used herein refers to a ring system which is chemically feasible and is known in the art and so intends to exclude those ring systems that are not chemically possible.

The groups ($C_1$-$C_8$)alkyl and ($C_6$-$C_{12}$)aryl as defined in the present invention may be unsubstituted or substituted as described herein, being the substituents placed on any available position.

The term "alkenyl" refers to a straight or branched hydrocarbon chain which contains the number of carbon atoms specified in the description or claims, and that also contains at least one double bond. Examples include, among others, the ethenyl, 2-propenyl, and 1-propenyl.

The term "alkinyl" refers to a straight or branched hydrocarbon chain which contains the number of carbon atoms specified in the description or claims, and that also contains at least one triple bond.

The term "edible" used herein means non-toxic and suitable for consumption.

As mentioned above, the first aspect of the invention is the provision of a cocrystal of beta-sitosterol or a pharmaceutically acceptable ester thereof or an edible acceptable ester thereof and a hydrogen bond donor coformer.

In an embodiment, the beta-sitosterol of the cocrystal of beta-sitosterol and a hydrogen bond donor coformer is in form of a pharmaceutically acceptable ester. The term "pharmaceutically acceptable ester" used herein encompasses an ester formed from pharmaceutically acceptable non-toxic acids including inorganic or organic acids. There is no limitation regarding the ester, except that if used for therapeutic purposes in medicine, they must be pharmaceutically acceptable.

In an embodiment, the beta-sitosterol of the cocrystal of beta-sitosterol and a hydrogen bond donor coformer is in form of an edible acceptable ester. The term "edible acceptable ester" used herein encompasses an ester formed from edible acceptable non-toxic acids including inorganic or organic acids.

Esters of beta-sitosterol may be prepared from pharmaceutically acceptable non-toxic acids and edible acids, including inorganic and organic acids. Such acids include among others acetic, butyric, propionic, benzene sulfonic, benzoic, camphor sulfonic, citric, ethansulfonic, fumaric, gluconic, glutamic, hydrobromic, hydrochloric, lactic, maleic, malic, mandelic, methane sulphuric, phosphoric, succinic, sulphuric, tartaric and p-toluene sulphuric acid. Such acids also include among others ($C_6$-$C_{22}$) alkyl fatty acids, ($C_6$-$C_{22}$) alkenyl fatty acids. The ($C_6$-$C_{22}$) alkyl fatty acids include medium-chain fatty acid containing aliphatic tails of ($C_6$-$C_{12}$) alkyl chains and long-chain fatty acids containing aliphatic tails of ($C_{13}$-$C_{22}$) alkyl chains. The ($C_6$-$C_{22}$) alkenyl fatty acids include medium-chain fatty acid containing aliphatic tails of ($C_6$-$C_{12}$) alkenyl chains and long-chain fatty acids containing aliphatic tails of ($C_{13}$-$C_{22}$) alkenyl chains. Examples of appropriate fatty acids include among others oleic acid, politic acid, stearic acid, eicosapentaenoic acid, docosahexaenoic acid, lauric acid and myristic acid.

In an embodiment, the cocrystal is a cocrystal of beta-sitosterol and a hydrogen bond donor coformer.

The term "hydrogen bond donor" refers to a compound having at least one electropositive hydrogen atom capable of interacting with an electronegative atom through a hydrogen bond.

In an embodiment, the cocrystal of beta-sitosterol is one wherein the hydrogen bond donor coformer is selected from the group consisting of organic carboxylic acid and organic alcohol.

In an embodiment, the cocrystal of beta-sitosterol is one which is a hydrate cocrystal of beta-sitosterol and a hydrogen bond donor coformer selected from the group consisting of organic carboxylic acid and organic alcohol; preferably which is a monohydrate cocrystal.

The term "organic carboxylic acid" refers to a pharmaceutically acceptable organic acid containing at least one —COOH group. In an embodiment, the cocrystal of beta-sitosterol is one wherein the hydrogen bond donor coformer is an organic carboxylic acid selected from a compound of $R_1$—$(COOH)_n$ and

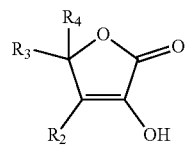

wherein: $R_1$ is selected from the group consisting of ($C_1$-$C_6$)alkyl, ($C_2$-$C_6$) alkenyl, and ($C_2$-$C_6$)alkinyl being optionally substituted by one or more hydroxyl groups; $R_2$ is selected from the group consisting of H and OH; $R_3$ is selected from the group consisting of H and —COOH; $R_4$ is a (c1-C6) alkyl; and n is an integer selected from 1 to 3.

In an embodiment, the cocrystal of beta-sitosterol is one wherein the hydrogen bond donor coformer is an organic carboxylic acid selected from the group consisting of L-lactic acid, propionic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid. In an embodiment, the cocrystal of beta-sitosterol is one wherein the hydrogen bond donor coformer is an organic carboxylic acid selected from the group consisting of L-lactic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid.

In an embodiment, the cocrystal of the invention is a cocrystal of beta-sitosterol and L-lactic acid named cocrystal Form 1. For the purposes of the invention, L-lactic acid is the International Nonproprietary Name (INN) of 2-(S) hydroxypropanoic acid, and has the CAS No. 79-33-4. The structure of L-lactic acid is the following:

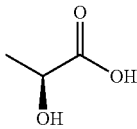

In an embodiment, the cocrystal of beta-sitosterol and L-lactic acid of the present invention is characterized by having an X-ray powder diffractogram that comprises characteristic peaks at approximately 2.3 and 4.6±0.3 degrees 2 theta (Cu—$K_\alpha$ radiation, $\lambda$=1.5406 Å). In an embodiment, the cocrystal of beta-sitosterol and L-lactic acid of the invention is characterized by having an X-ray powder diffractogram that comprises further characteristic peaks at 14.5, 15.7 and 17.5±0.3 degrees 2 theta (Cu—$K_\alpha$ radiation, $\lambda$=1.5406 Å).

More specifically, the cocrystal of beta-sitosterol and L-lactic acid of the invention is characterized by exhibiting in the X-ray powder diffractogram a pattern of peaks, expressed in 2 theta units in degrees, 2θ(°), which is shown in Table 1.

TABLE 1

List of selected peaks (only peaks with relative intensity greater than or equal to 1% are indicated):

| Pos. [°2Th.] | d-spacing [Å] | Rel. Int. [%] |
|---|---|---|
| 2.3039 | 38.3482 | 100 |
| 4.6282 | 19.09325 | 14.13 |
| 10.3849 | 8.51852 | 3.72 |
| 12.2217 | 7.24211 | 10.27 |
| 14.4808 | 6.11696 | 54.77 |
| 15.0061 | 5.90401 | 51.59 |
| 15.193 | 5.83179 | 11.73 |
| 15.7171 | 5.63846 | 25.11 |
| 17.5398 | 5.05644 | 50.35 |
| 17.8982 | 4.95597 | 15.12 |
| 18.2229 | 4.8684 | 17.6 |
| 18.5566 | 4.78159 | 27.17 |
| 18.7405 | 4.7351 | 17.26 |
| 19.5991 | 4.52954 | 12.14 |
| 20.6452 | 4.30233 | 12.83 |
| 21.2497 | 4.18129 | 16.11 |
| 21.8698 | 4.06412 | 8.15 |
| 22.2605 | 3.99366 | 7.72 |
| 23.861 | 3.72929 | 3.51 |
| 25.7711 | 3.45705 | 2.96 |

The cocrystal of beta-sitosterol and L-lactic acid of the invention may be further characterized by an X-ray diffractogram as in FIG. 1.

In an embodiment, the cocrystal of the invention is a cocrystal of beta-sitosterol and propionic acid named cocrystal Form 2. For the purposes of the invention, propionic acid is the International Nonproprietary Name (INN) of propanoic acid, and has the CAS No. 79-09-4. The structure of propionic acid is the following:

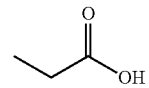

In an embodiment, the cocrystal of beta-sitosterol and propionic acid of the present invention is characterized by having an X-ray powder diffractogram that comprises characteristic peaks at approximately 2.2 and 4.4±0.3 degrees 2 theta (Cu—$K_\alpha$ radiation, $\lambda$=1.5406 Å). In an embodiment, the cocrystal of beta-sitosterol and propionic acid of the invention is characterized by having an X-ray powder diffractogram that comprises further characteristic peaks at 11.8, 12.4 and 14.8±0.3 degrees 2 theta (Cu—$K_\alpha$ radiation, $\lambda$=1.5406 Å).

More specifically, the cocrystal of beta-sitosterol and propionic acid of the invention is characterized by exhibiting in the X-ray powder diffractogram a pattern of peaks, expressed in 2 theta units in degrees, 2θ(°), which is shown in Table 2.

TABLE 2

List of selected peaks (only peaks with relative intensity greater than or equal to 0.5% are indicated):

| Pos. [°2Th.] | d-spacing [Å] | Rel. Int. [%] |
|---|---|---|
| 2.2079 | 40.0142 | 17.92 |
| 4.432 | 19.93772 | 10.96 |
| 9.7397 | 9.08136 | 1.23 |
| 10.7032 | 8.2659 | 0.52 |
| 11.1144 | 7.96096 | 0.85 |
| 11.7902 | 7.50615 | 6.75 |

TABLE 2-continued

List of selected peaks (only peaks with relative intensity greater than or equal to 0.5% are indicated):

| Pos. [°2Th.] | d-spacing [Å] | Rel. Int. [%] |
|---|---|---|
| 12.4054 | 7.13523 | 3.53 |
| 13.3717 | 6.6217 | 0.75 |
| 14.8243 | 5.976 | 100 |
| 15.1539 | 5.84674 | 9.72 |
| 15.8013 | 5.60862 | 4.23 |
| 16.7233 | 5.30142 | 1.52 |
| 18.3456 | 4.8361 | 7.84 |
| 18.5087 | 4.79387 | 25.49 |
| 18.9057 | 4.69409 | 11.93 |
| 19.2421 | 4.61278 | 1.84 |
| 19.5639 | 4.53762 | 8.45 |
| 21.751 | 4.08604 | 2.11 |
| 21.8875 | 4.06087 | 3.11 |
| 22.2214 | 4.0006 | 5.6 |
| 23.3824 | 3.80453 | 2.34 |
| 25.0867 | 3.54979 | 2.07 |
| 25.2893 | 3.5218 | 1.93 |
| 27.7141 | 3.21894 | 1.97 |

Figure 2:
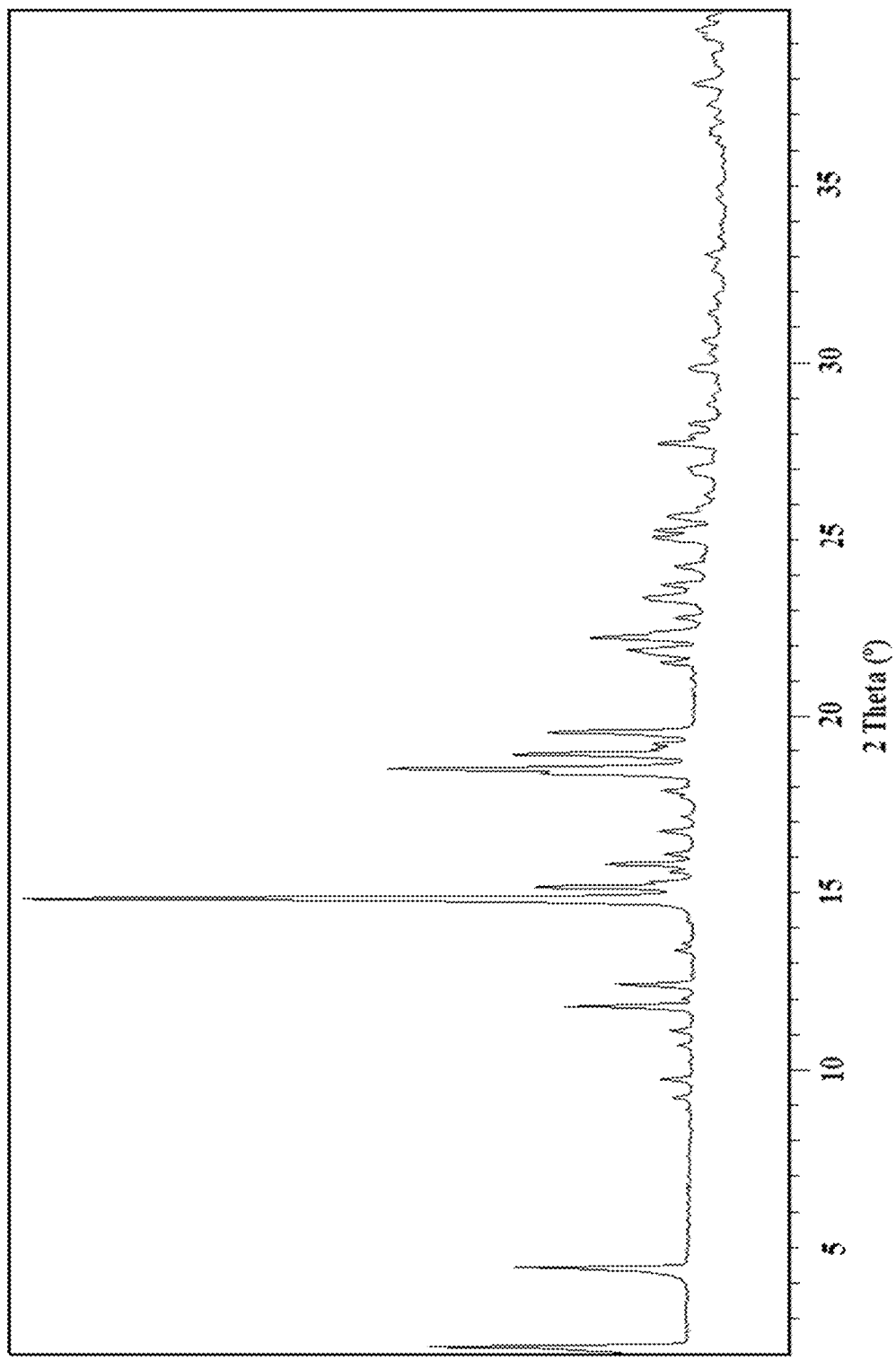
FIG. 2 shows the X-ray powder diffractogram (XRPD) of the cocrystal of beta-sitosterol and propionic acid of the present invention. The spectrum expresses intensity (I; counts) versus degrees 2 theta (°).

The cocrystal of beta-sitosterol and propionic acid of the invention may be further characterized by an X-ray diffractogram as in FIG. 2.

Figure 3:
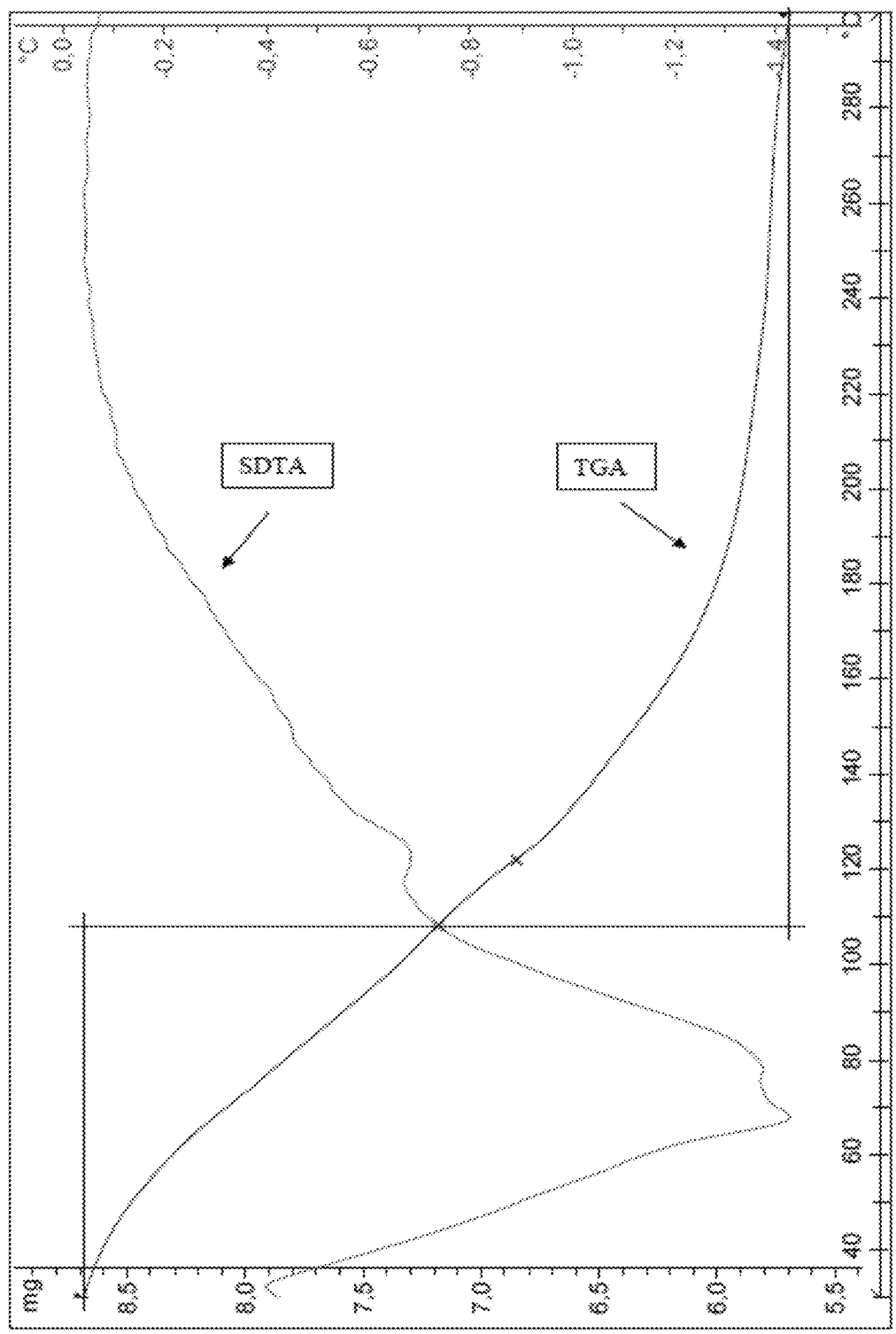
FIG. 3 shows the TGA of cocrystal of beta-sitosterol and propionic acid of the present invention. The thermogram expresses loss weight (% w/w) versus temperature (° C.).

The thermogravimetric (TG) analysis of the cocrystal of beta-sitosterol and propionic acid of the invention may also be further characterized by a first weight loss of 35.0% from 30° C. to 300° C. (cf. FIG. 3).

Figure 4:
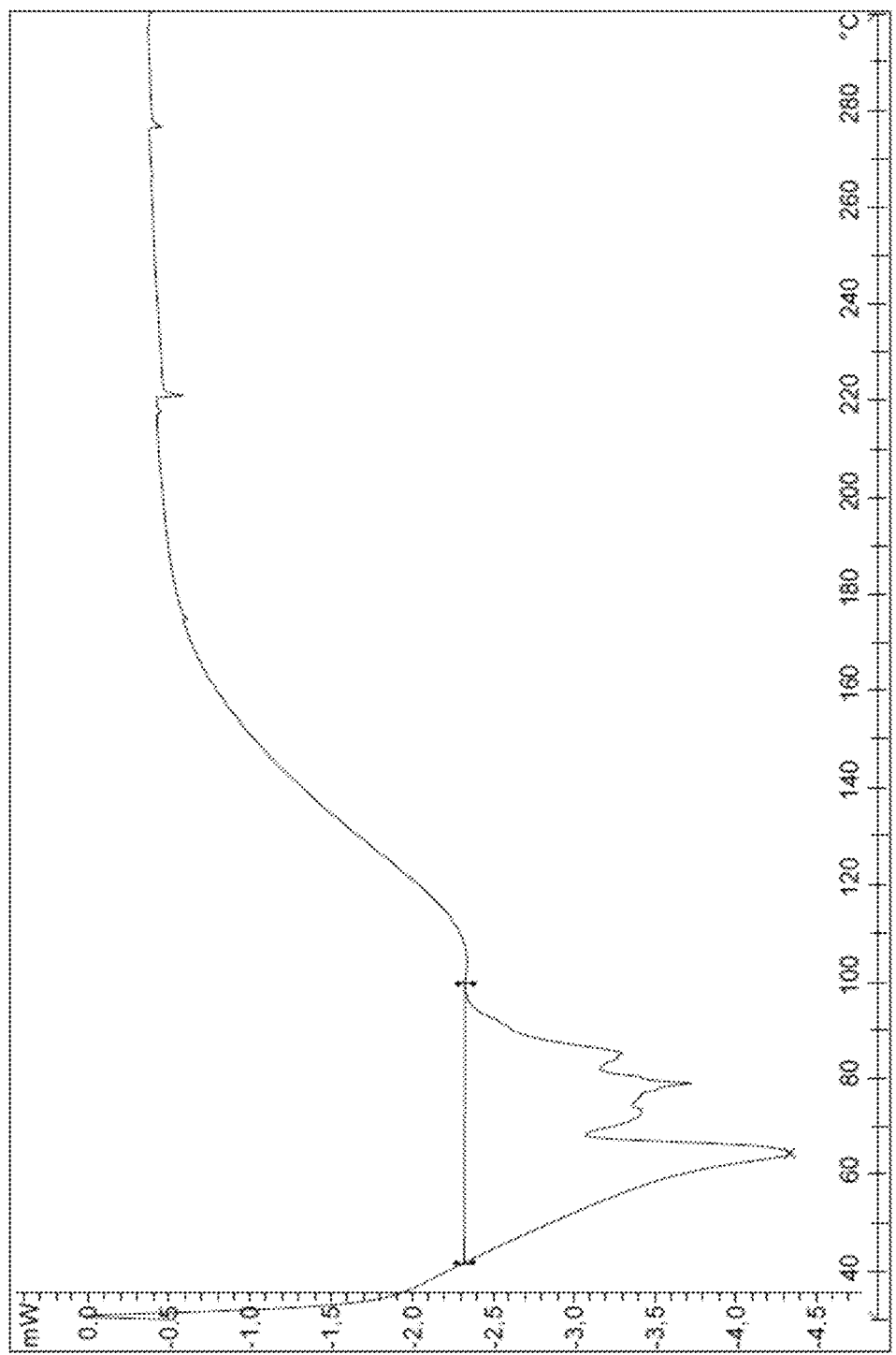
FIG. 4 shows the DSC of cocrystal of beta-sitosterol and propionic acid of the present invention. The DSC thermal curve expresses the heat flow (m/W) versus temperature (° C.).

The cocrystal of beta-sitosterol and propionic acid of the invention may also be further characterized by a wide endothermic phenomenon (overlapping four phenomena) at 44° C. with an associated heat of 79.2 J/g by DSC (Differential scanning calorimetry) analysis (cf. FIG. 4).

In an embodiment, the cocrystal of beta-sitosterol and propionic acid of the formula below is in a molar ratio 2:1.

In an embodiment, the cocrystal beta-sitosterol and propionic acid is a hydrate cocrystal; preferably the cocrystal of beta-sitosterol and propionic acid is a monohydrate cocrystal having a molar ratio beta-sitosterol:propionic acid of 2:1.

The data of the structure of the cocrystal beta-sitosterol:propionic acid defined above obtained by single crystal X-ray diffraction correspond to a monohydrate cocrystal and are shown below:

| Structure | cocrystal beta-sitosterol:propionic acid Form I |
|---|---|
| Temperature (K) | 293(2) |
| Wavelength (Å) | 0.71073 |
| Crystal system | Monoclinic |
| space group | P 2 1 |
| a, b, c (Å) | 9.439(2), 7.5391(16), 39.635(8) |
| α, β, γ (°) | 90, 95.216(6), 90 |
| Volume (Å³) | 2808.8(10) |
| Z, Density (calc.) (Mg/m³) | 2, 1.090 |
| Final R indices [I > 2σ(I)] | R1 = 0.0446, wR2 = 0.0582 |

In an embodiment, the cocrystal of the invention is a cocrystal of beta-sitosterol and zymonic acid named cocrystal Form 3. For the purposes of the invention, zymonic acid is the International Nonproprietary Name (INN) of 4-hydroxy-2-methyl-5-oxo-2,5-dihydrofuran-2-carboxylic acid, and has the CAS No. 24891-71-2. The structure of zymonic acid is the following:

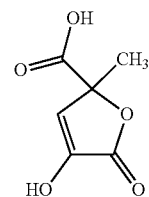

In an embodiment, the cocrystal of beta-sitosterol and zymonic acid of the present invention is characterized by having an X-ray powder diffractogram that comprises characteristic peaks at approximately 2.2 and 4.5±0.3 degrees 2 theta (Cu—K$_\alpha$ radiation, λ=1.5406 Å). In an embodiment, the cocrystal of beta-sitosterol and zymonic acid of the invention is characterized by having an X-ray powder diffractogram that comprises further characteristic peaks at 6.7, 15.4 and 18.0±0.3 degrees 2 theta (Cu—K$_\alpha$ radiation, λ=1.5406 Å).

More specifically, the cocrystal of beta-sitosterol and zymonic acid of the invention is characterized by exhibiting in the X-ray powder diffractogram a pattern of peaks, expressed in 2 theta units in degrees, 2θ (°), which is shown in Table 3.

TABLE 3

List of selected peaks (only peaks with relative intensity greater than or equal to 1% are indicated):

| Pos. [°2Th.] | d-spacing [Å] | Rel. Int. [%] |
|---|---|---|
| 2.2279 | 39.65595 | 84.14 |
| 4.4615 | 19.80623 | 4.78 |
| 6.6933 | 13.20612 | 3.53 |
| 8.95 | 9.88076 | 6.07 |
| 11.5712 | 7.6477 | 22.78 |
| 11.9936 | 7.37932 | 15 |
| 14.5198 | 6.1006 | 86.32 |
| 14.8098 | 5.98181 | 100 |
| 15.4391 | 5.73937 | 68.23 |
| 15.6534 | 5.66129 | 16.24 |
| 16.3512 | 5.42123 | 15.36 |
| 16.6202 | 5.33407 | 9.86 |
| 17.5522 | 5.05288 | 16 |
| 17.7766 | 4.9896 | 18.05 |
| 17.9991 | 4.92844 | 99.3 |
| 18.8578 | 4.70589 | 9.12 |
| 19.4917 | 4.55427 | 43.8 |
| 21.0624 | 4.21805 | 13.83 |
| 23.2457 | 3.82659 | 6.77 |
| 23.59 | 3.7715 | 7.21 |
| 25.1481 | 3.54127 | 5.5 |
| 27.135 | 3.2863 | 9.89 |
| 36.5331 | 2.45961 | 2.84 |

Figure 5:
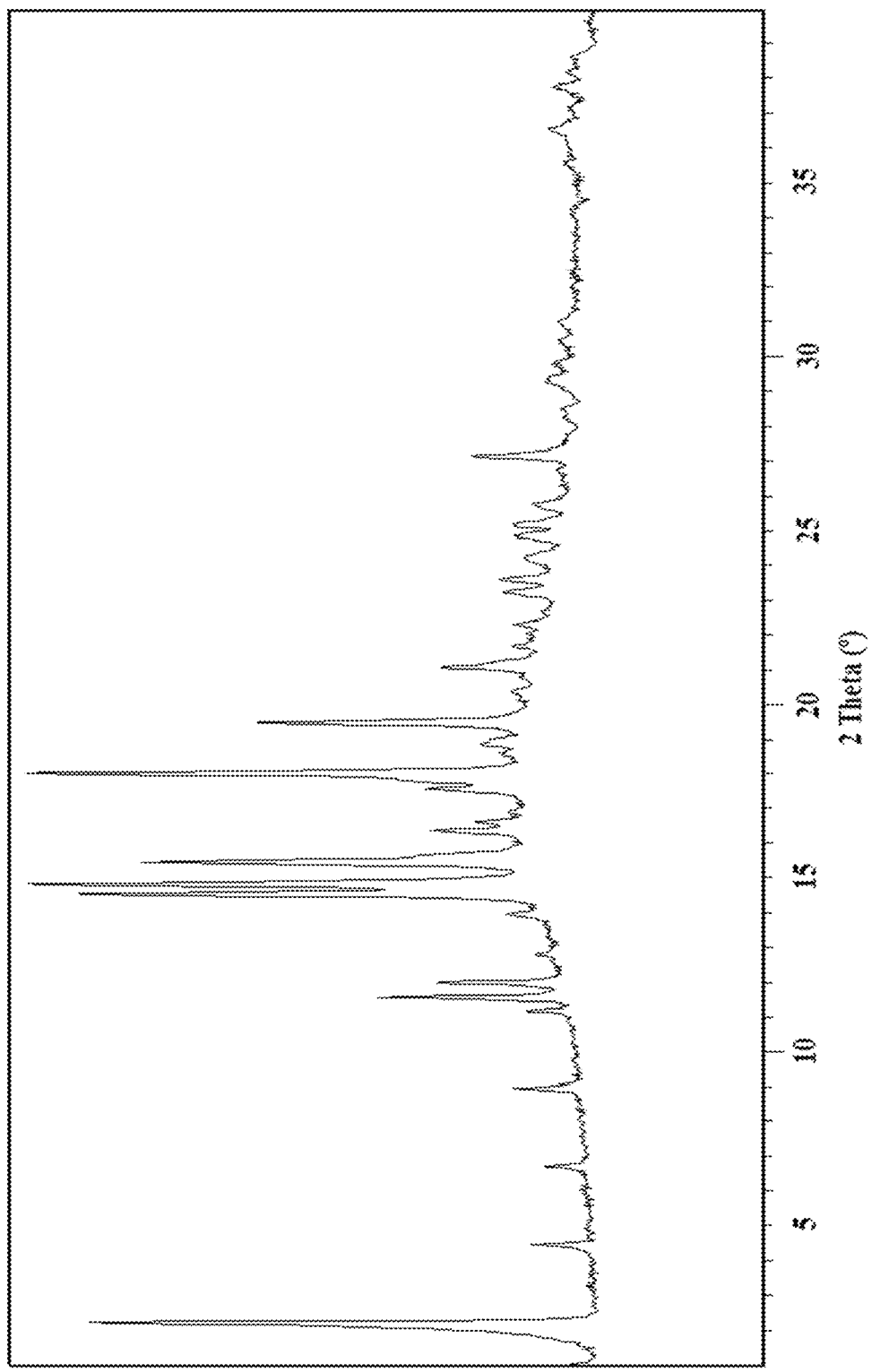
FIG. 5 shows the X-ray powder diffractogram (XRPD) of the cocrystal of beta-sitosterol and zymonic acid of the present invention. The spectrum expresses intensity (I; counts) versus degrees 2 theta (°).

The cocrystal of beta-sitosterol and zymonic acid of the invention may be further characterized by an X-ray diffractogram as in FIG. 5.

Figure 6:
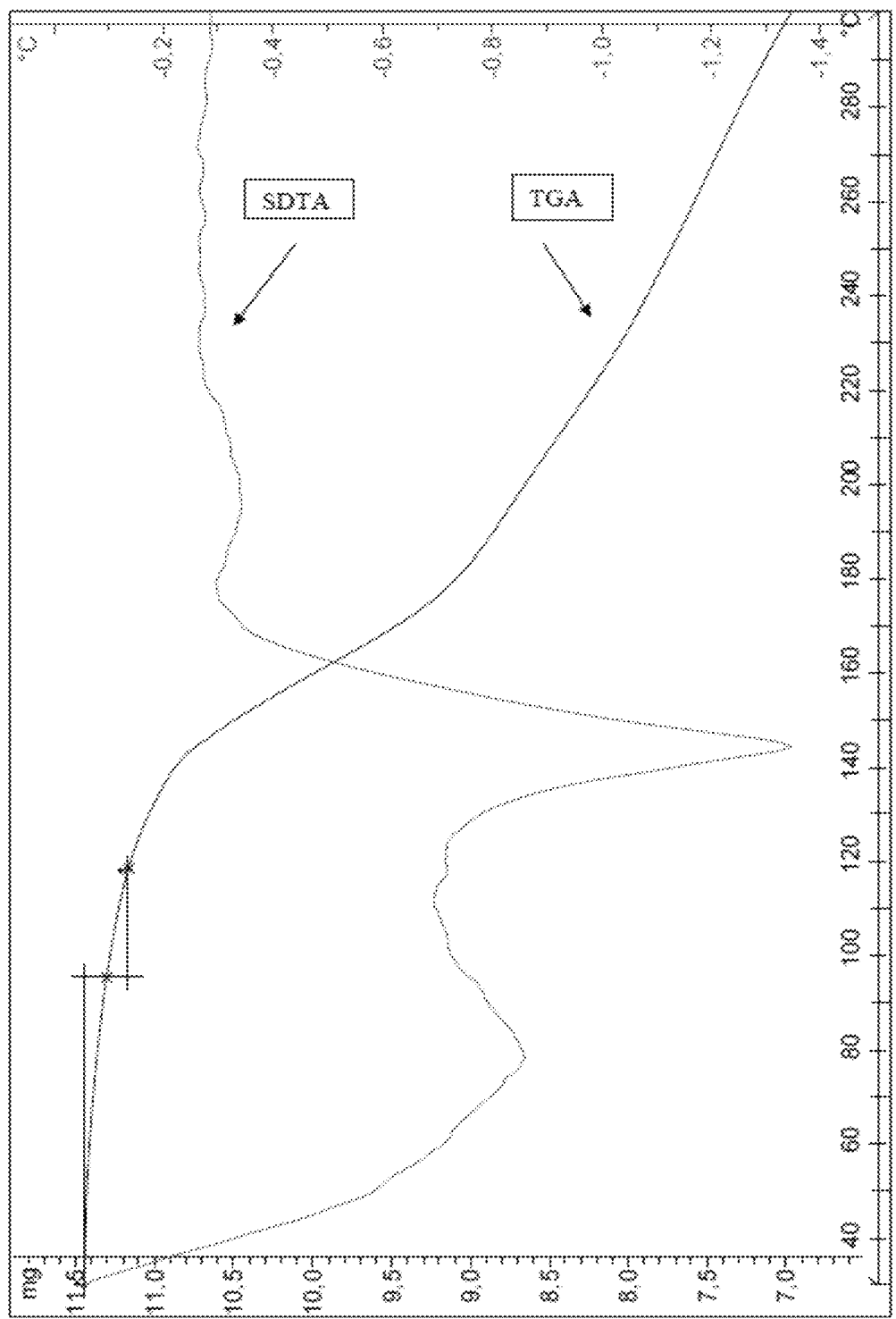
FIG. 6 shows the TGA of cocrystal of beta-sitosterol and zymonic acid of the present invention. The thermogram expresses loss weight (% w/w) versus temperature (° C.).

The thermogravimetric (TG) analysis of the cocrystal of beta-sitosterol and zymonic acid of the invention may also be further characterized by a first weight loss of 2.4% from 30° C. to 118° C. and a second weight loss of 36.6% from 118° C. to 300° C. (cf. FIG. 6).

Figure 7:
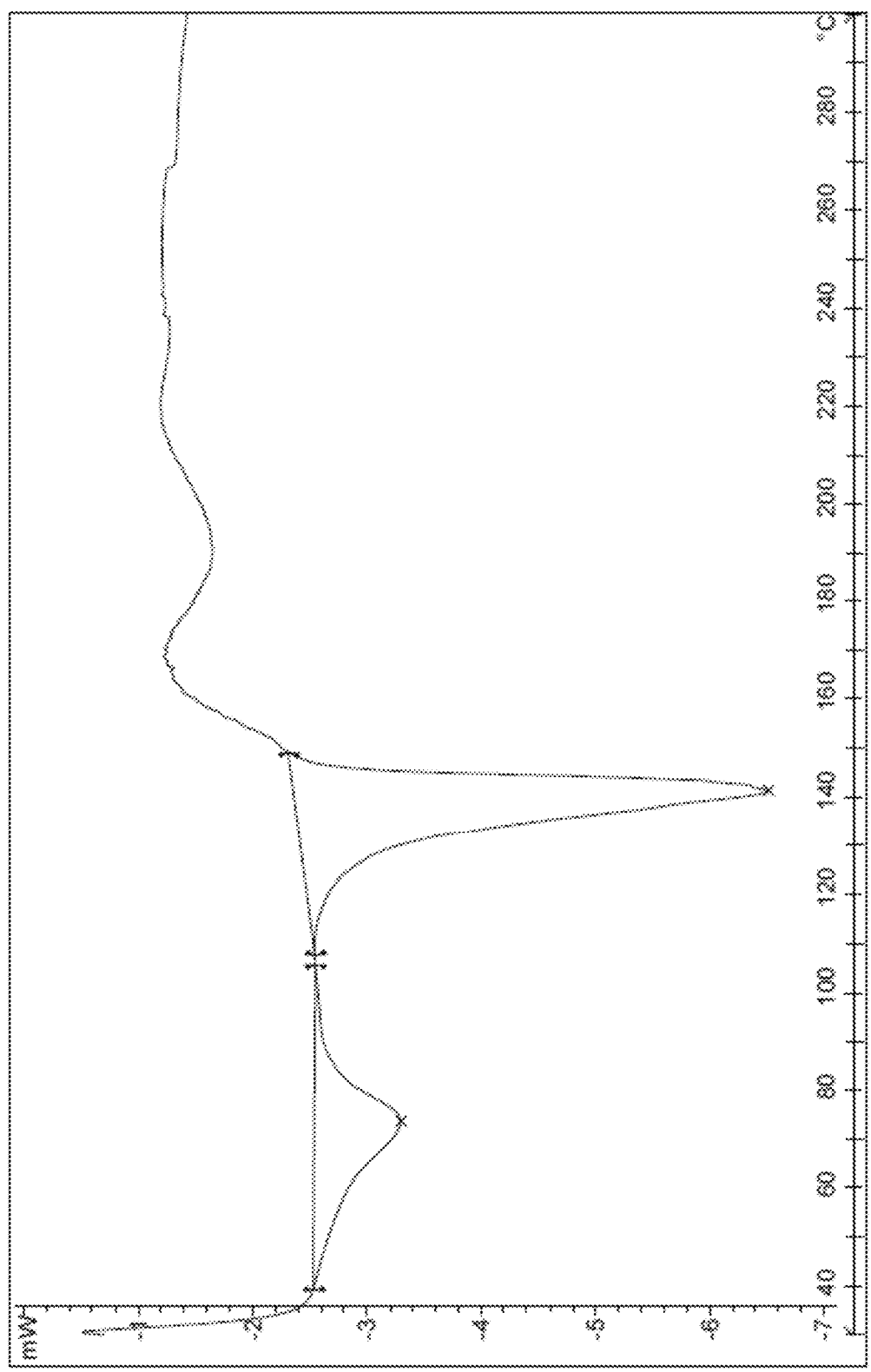
FIG. 7 shows the DSC of cocrystal of beta-sitosterol and zymonic acid of the present invention. The DSC thermal curve expresses the heat flow (m/W) versus temperature (° C.).

The cocrystal of beta-sitosterol and zymonic acid of the invention may also be further characterized by a first wide endothermic phenomenon at 59° C. with an associated heat of 15.9 J/g and a second endothermic phenomenon at 125° C. with an associated heat of 42.1 J/g by DSC (Differential scanning calorimetry) analysis (cf. FIG. 7).

In an embodiment, the cocrystal of beta-sitosterol and zymonic acid of the formula below is in a molar ratio 2:1.

In an embodiment, the cocrystal beta-sitosterol and zymonic acid is a hydrate cocrystal; preferably the cocrystal of beta-sitosterol and zymonic acid is a monohydrate cocrystal having a molar ratio beta-sitosterol:zymonic acid 2:1.

In an embodiment, the cocrystal of the invention is a cocrystal of beta-sitosterol and gallic acid named cocrystal Form 5. For the purposes of the invention, gallic acid is the International Nonproprietary Name (INN) of 3,4,5-trihydroxybenzoic acid, and has the CAS No. 149-91-7. The structure of gallic acid is the following:

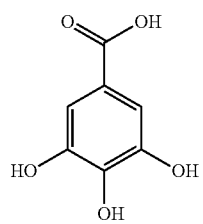

In an embodiment, the cocrystal of beta-sitosterol and gallic acid of the present invention is characterized by having an X-ray powder diffractogram that comprises characteristic peaks at approximately 7.9 and 16.3±0.3 degrees 2 theta (Cu—K$_\alpha$ radiation, λ=1.5406 Å). In an embodiment, the cocrystal of beta-sitosterol and gallic acid of the invention is characterized by having an X-ray powder diffractogram that comprises further characteristic peaks at 2.3, 13.0 and 15.9±0.3 degrees 2 theta (Cu—K$_\alpha$ radiation, λ=1.5406 Å).

More specifically, the cocrystal of beta-sitosterol and gallic acid of the invention is characterized by exhibiting in the X-ray powder diffractogram a pattern of peaks, expressed in 2 theta units in degrees, 2θ (°), which is shown in Table 6.

TABLE 6

List of selected peaks (only peaks with relative intensity greater than or equal to 1% are indicated):

| Pos. [°2Th.] | d-spacing [Å] | Rel. Int. [%] |
|---|---|---|
| 2.2758 | 38.82139 | 90.67 |
| 7.8535 | 11.25762 | 3.3 |
| 10.3241 | 8.56856 | 3.29 |
| 10.5109 | 8.41672 | 3.11 |
| 12.7844 | 6.92455 | 6.48 |
| 12.9943 | 6.81319 | 7.65 |
| 13.5933 | 6.51428 | 3.14 |
| 15.1627 | 5.84338 | 100 |
| 15.3938 | 5.75617 | 18.29 |
| 15.7428 | 5.62932 | 6.51 |
| 15.9463 | 5.55795 | 20.56 |
| 16.2769 | 5.44579 | 35.84 |
| 16.5323 | 5.36224 | 34.68 |
| 16.8022 | 5.27672 | 4.88 |
| 17.0895 | 5.18864 | 6.01 |
| 17.5447 | 5.05502 | 14.92 |
| 17.9266 | 4.9482 | 7.74 |
| 18.2674 | 4.85664 | 5.38 |
| 19.3777 | 4.5808 | 5.06 |
| 20.7919 | 4.27232 | 6.82 |
| 20.9522 | 4.23998 | 9.22 |
| 21.4177 | 4.14887 | 4.16 |
| 21.9304 | 4.05303 | 2.47 |
| 22.4417 | 3.96183 | 1.7 |
| 24.5058 | 3.6326 | 1.28 |
| 25.3571 | 3.51254 | 2.47 |

TABLE 6-continued

List of selected peaks (only peaks with relative intensity greater than or equal to 1% are indicated):

| Pos. [°2Th.] | d-spacing [Å] | Rel. Int. [%] |
|---|---|---|
| 26.0004 | 3.42709 | 1.37 |
| 26.7109 | 3.33752 | 1.63 |
| 28.2615 | 3.15782 | 1.06 |

Figure 17:
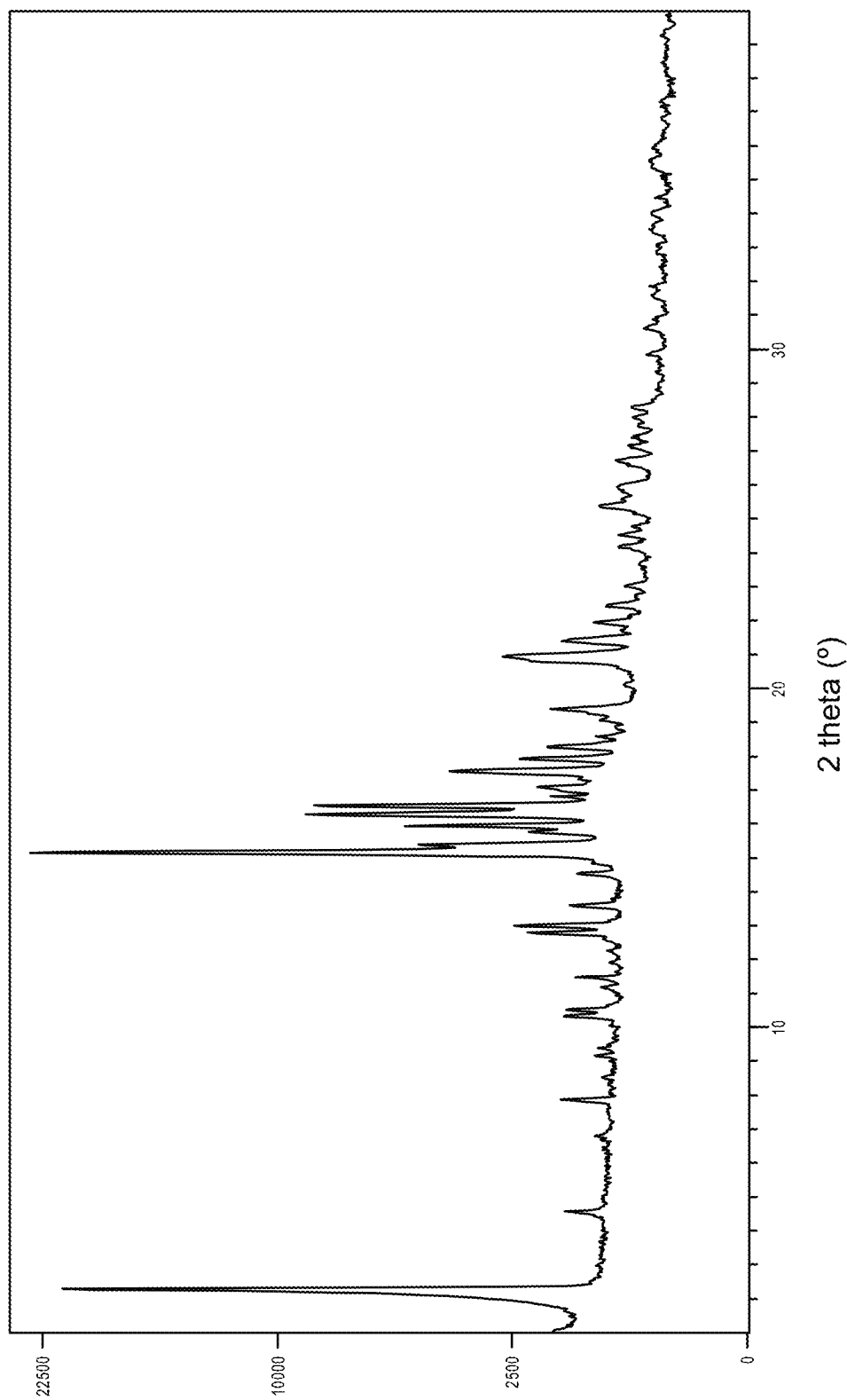
FIG. 17 shows the X-ray powder diffractogram (XRPD) of the cocrystal of beta-sitosterol and gallic acid of the present invention. The spectrum expresses intensity (I; counts) versus degrees 2 theta (°).

The cocrystal of beta-sitosterol and gallic acid of the invention may be further characterized by an X-ray diffractogram as in FIG. 17.

Figure 18:
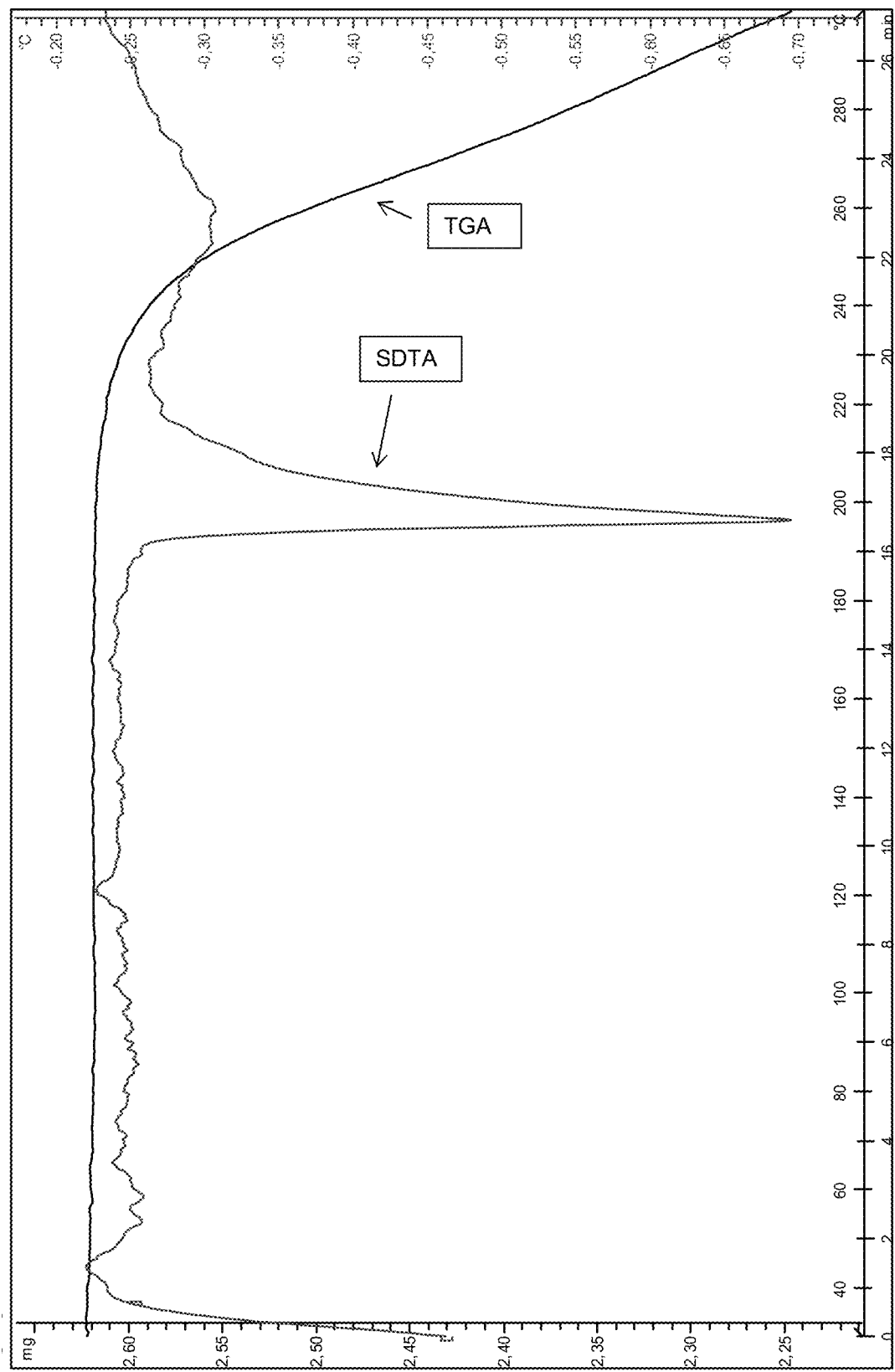
FIG. 18 shows the TGA of cocrystal of beta-sitosterol and gallic acid of the present invention. The thermogram expresses loss weight (% w/w) versus temperature (° C.).

The thermogravimetric (TG) analysis of the cocrystal of beta-sitosterol and gallic acid of the invention may also be further characterized by a thermal melting/decomposition phenomenon starting at 194° C. (cf. FIG. 18).

Figure 19:
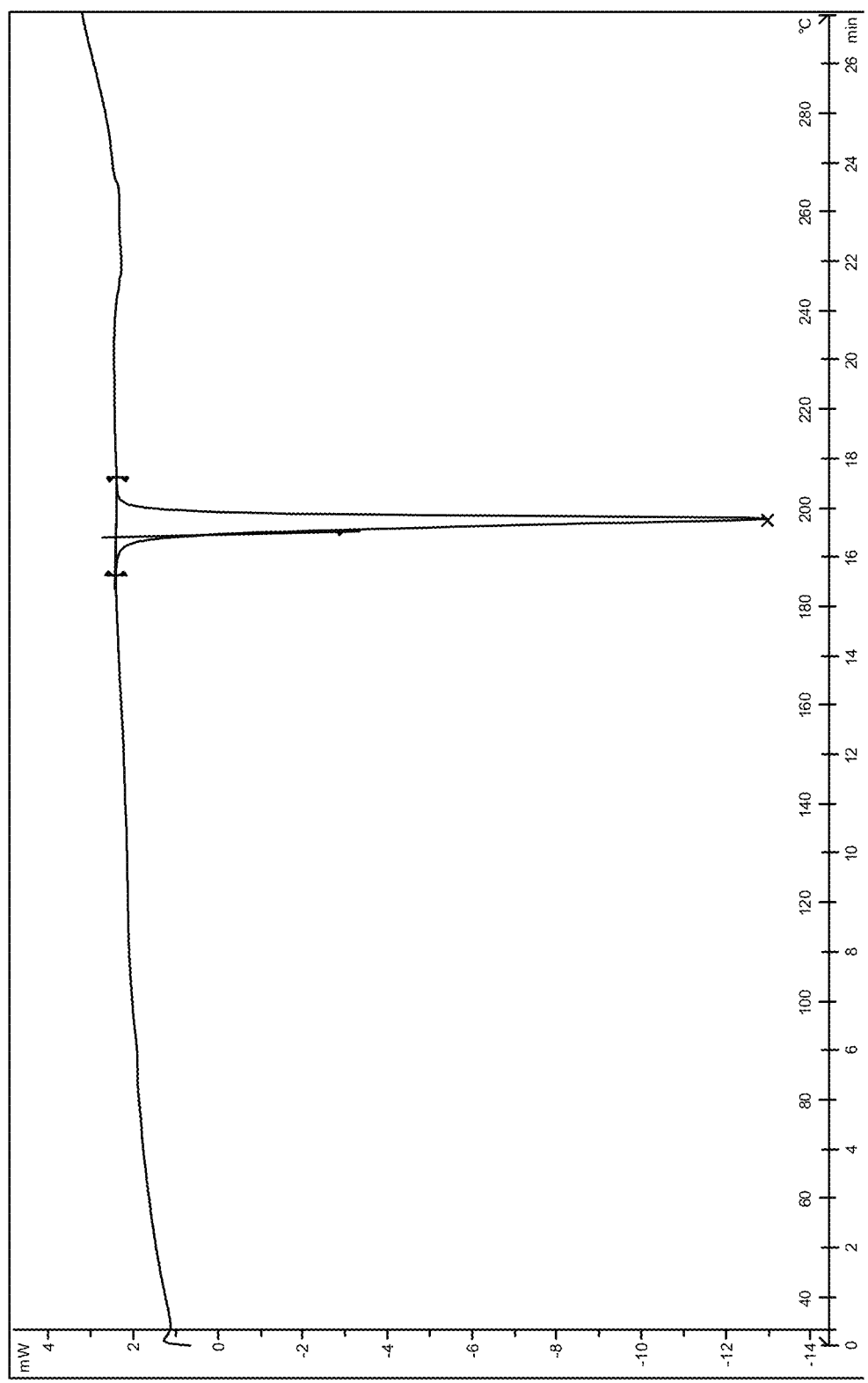
FIG. 19 shows the DSC of cocrystal of beta-sitosterol and gallic acid of the present invention. The DSC thermal curve expresses the heat flow (m/W) versus temperature (° C.).

The cocrystal of beta-sitosterol and gallic acid of the invention may also be further characterized by an endothermic phenomenon at 194° C. with an associated heat of 63.8 J/g by DSC (Differential scanning calorimetry) analysis (cf. FIG. 19).

In an embodiment, the cocrystal of beta-sitosterol and 2,4-dihydroxybenzoic acid of the formula below is in a molar ratio 2:1.

In an embodiment, the cocrystal of the invention is a cocrystal of beta-sitosterol and 2,4-dihydroxybenzoic acid named cocrystal Form 6. For the purposes of the invention, 2,4-dihydroxybenzoic acid has the CAS No. 89-86-1. The structure of 2,4-dihydroxybenzoic acid is the following:

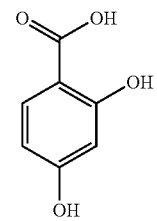 [SMILES: O=C(O)c1ccc(O)cc1O]

In an embodiment, the cocrystal of beta-sitosterol and 2,4-dihydroxybenzoic acid of the present invention is characterized by having an X-ray powder diffractogram that comprises characteristic peaks at approximately 11.4 and 16.2±0.3 degrees 2 theta (Cu—K$_\alpha$ radiation, λ=1.5406 Å). In an embodiment, the cocrystal of beta-sitosterol and 2,4-dihydroxybenzoic acid of the invention is characterized by having an X-ray powder diffractogram that comprises further characteristic peaks at 4.6, 15.8 and 17.9±0.3 degrees 2 theta (Cu—K$_\alpha$ radiation, λ=1.5406 Å).

More specifically, the cocrystal of beta-sitosterol and 2,4-dihydroxybenzoic acid of the invention is characterized by exhibiting in the X-ray powder diffractogram a pattern of peaks, expressed in 2 theta units in degrees, 2θ(°), which is shown in Table 7.

TABLE 7

List of selected peaks (only peaks with relative intensity greater than or equal to 1% are indicated):

| Pos. [°2Th.] | d-spacing [Å] | Rel. Int. [%] |
|---|---|---|
| 2.0736 | 42.60629 | 21.01 |
| 2.2781 | 38.7817 | 100 |
| 4.5653 | 19.35603 | 6.62 |

TABLE 7-continued

List of selected peaks (only peaks with relative intensity greater than or equal to 1% are indicated):

| Pos. [°2Th.] | d-spacing [Å] | Rel. Int. [%] |
|---|---|---|
| 6.2751 | 14.08535 | 2.31 |
| 7.7677 | 11.3818 | 2.92 |
| 9.1446 | 9.67088 | 2.65 |
| 10.4987 | 8.42645 | 2.95 |
| 11.4334 | 7.73954 | 3.92 |
| 12.6312 | 7.00819 | 4.48 |
| 12.7968 | 6.91788 | 3.3 |
| 14.3408 | 6.17635 | 2.36 |
| 15.1249 | 5.85787 | 44.87 |
| 15.5038 | 5.71556 | 6.69 |
| 15.7965 | 5.61032 | 6.27 |
| 16.1677 | 5.48233 | 6.1 |
| 16.7136 | 5.30447 | 25.43 |
| 17.059 | 5.19785 | 6.99 |
| 17.303 | 5.1251 | 7.78 |
| 17.6865 | 5.01482 | 4.2 |
| 17.8706 | 4.96357 | 7.8 |
| 18.2027 | 4.87376 | 2.92 |
| 19.0683 | 4.65442 | 3.89 |
| 20.7108 | 4.28885 | 3.12 |
| 20.9897 | 4.23249 | 3.09 |
| 22.1159 | 4.01945 | 1.67 |
| 24.787 | 3.59203 | 1.67 |

Figure 20:
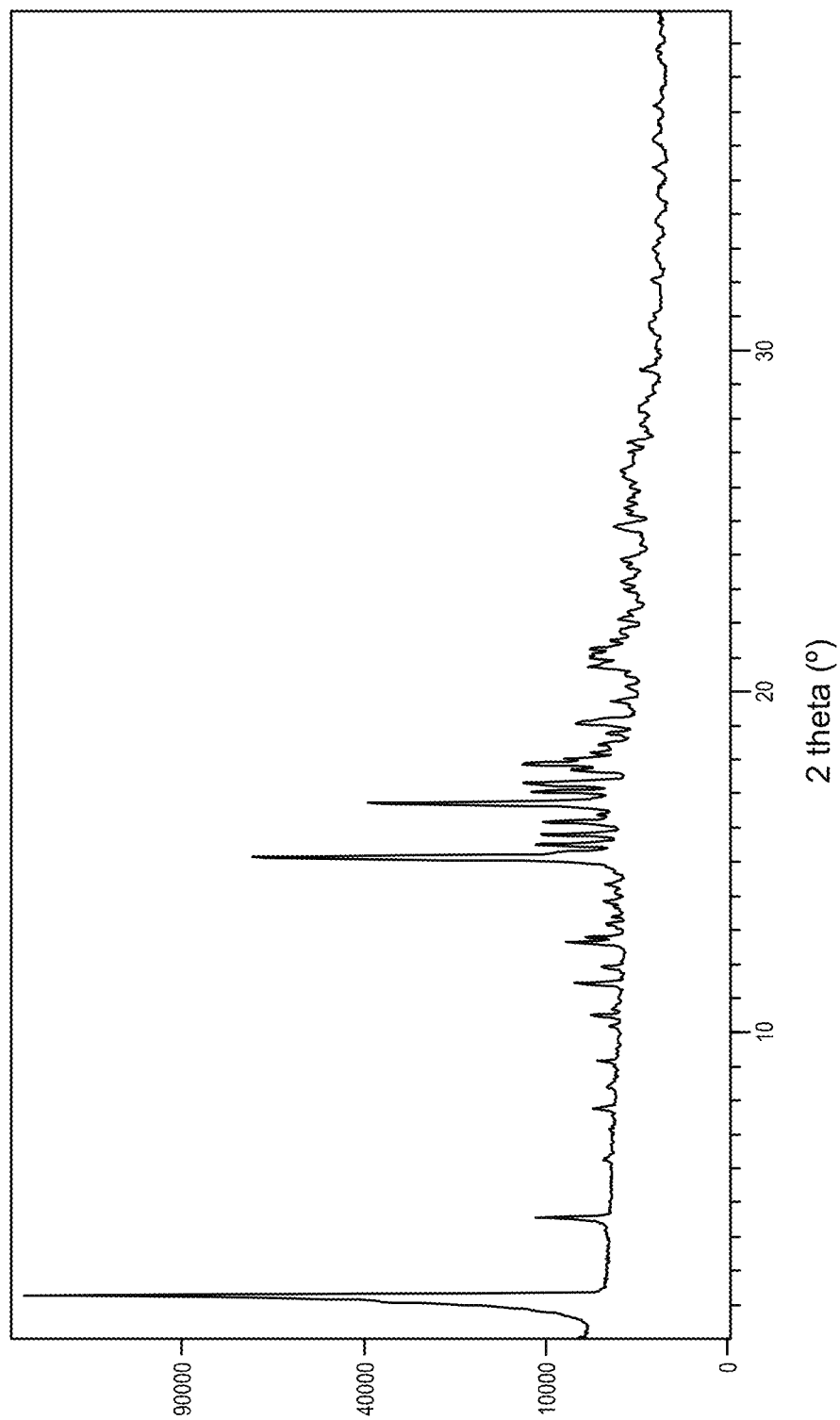
FIG. 20 shows the X-ray powder diffractogram (XRPD) of the cocrystal of beta-sitosterol and 2,4-dihydroxybenzoic acid of the present invention. The spectrum expresses intensity (I; counts) versus degrees 2 theta (°).

The cocrystal of beta-sitosterol and 2,4-dihydroxybenzoic acid of the invention may be further characterized by an X-ray diffractogram as in FIG. 20.

Figure 21:
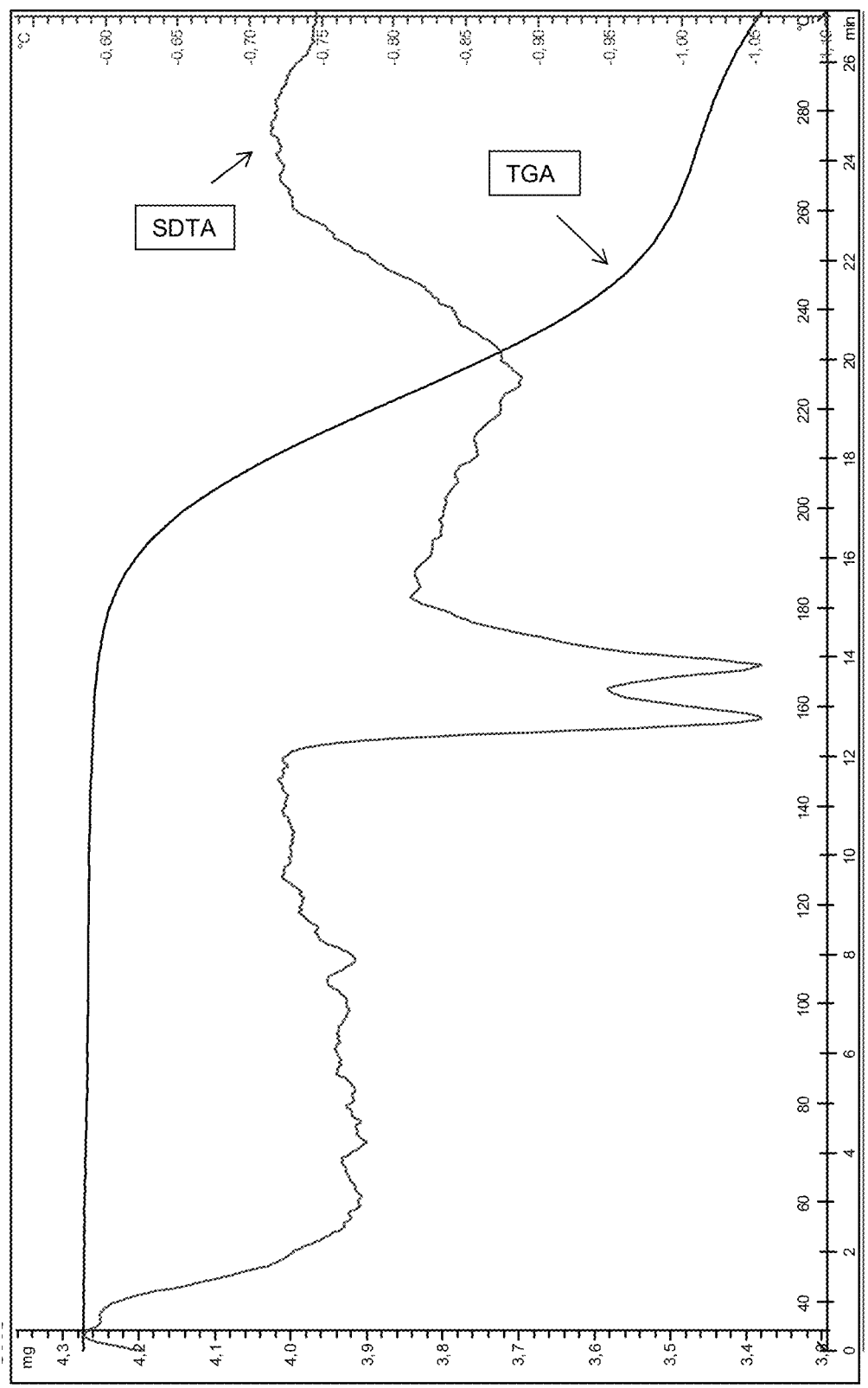
FIG. 21 shows the TGA of cocrystal of beta-sitosterol and 2,4-dihydroxybenzoic acid of the present invention. The thermogram expresses loss weight (% w/w) versus temperature (° C.).

The thermogravimetric (TG) analysis of the cocrystal of beta-sitosterol and 2,4-dihydroxybenzoic acid of the invention may also be further characterized by a thermal melting/decomposition phenomenon starting at 151° C. (cf. FIG. 21).

Figure 22:
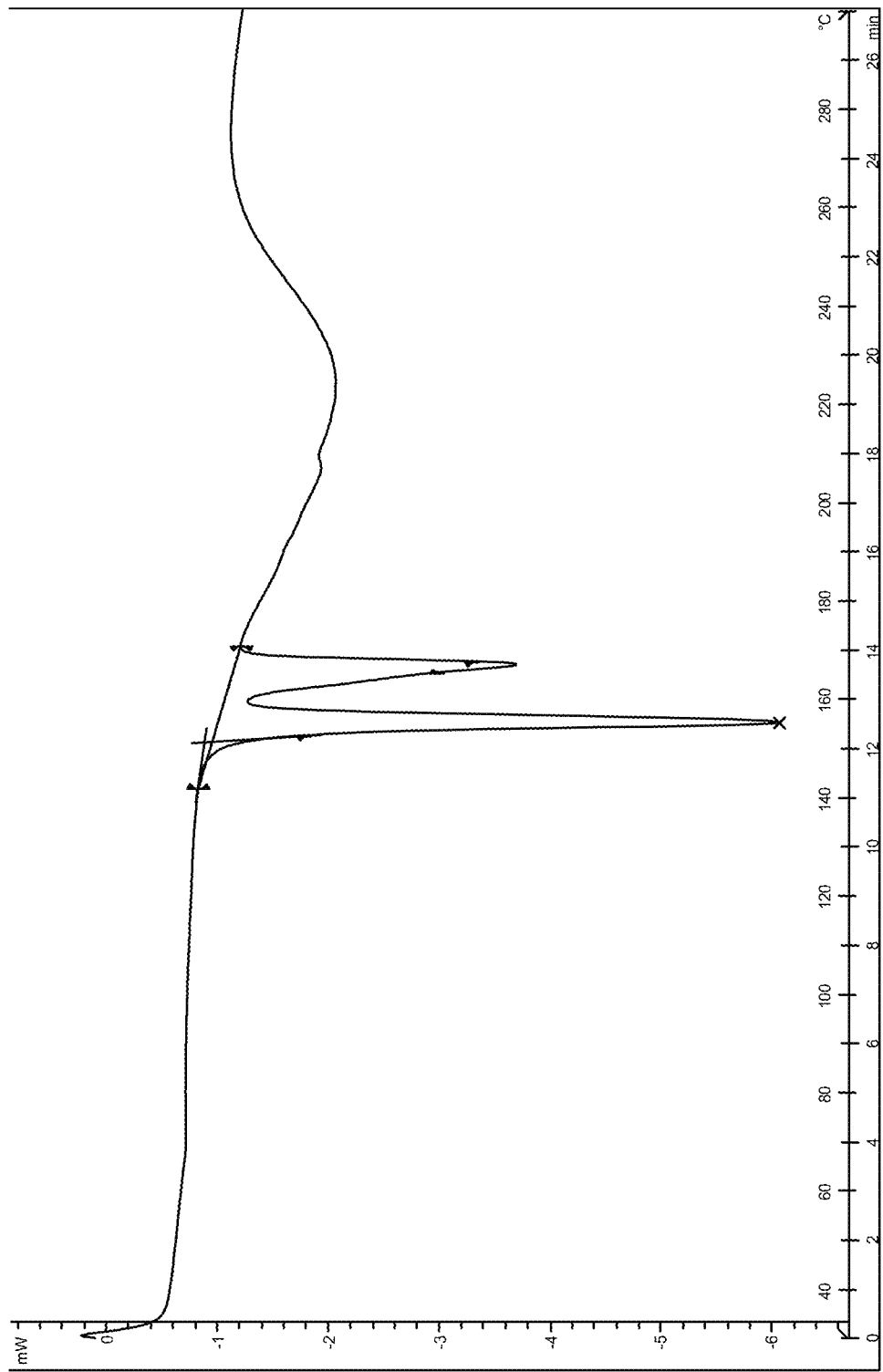
FIG. 22 shows the DSC of cocrystal of beta-sitosterol and 2,4-dihydroxybenzoic acid of the present invention. The DSC thermal curve expresses the heat flow (m/W) versus temperature (° C.).

The cocrystal of beta-sitosterol and 2,4-dihydroxybenzoic acid of the invention may also be further characterized by two superimposed phenomena with a total associated heat of 51.7 J/g: a first wide endothermic phenomenon at 151° C. and a second endothermic phenomenon with a peak at 167° C. by DSC (Differential scanning calorimetry) analysis (cf. FIG. 22).

In an embodiment, the cocrystal of beta-sitosterol and 2,4-dihydroxybenzoic acid of the formula below is in a molar ratio 1:1.

In an embodiment, the cocrystal of the invention is a cocrystal of beta-sitosterol and 3,4-dihydroxybenzoic acid named cocrystal Form 7. For the purposes of the invention, 3,4-dihydroxybenzoic acid has the CAS No. 99-50-3. The structure of 3,4-dihydroxybenzoic acid is the following:

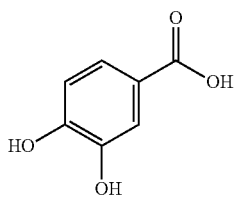

In an embodiment, the cocrystal of beta-sitosterol and 3,4-dihydroxybenzoic acid of the present invention is characterized by having an X-ray powder diffractogram that comprises characteristic peaks at 2.3 and 15.9±0.3 degrees 2 theta (Cu—$K_\alpha$ radiation, $\lambda$=1.5406 Å). In an embodiment, the cocrystal of beta-sitosterol and 3,4-dihydroxybenzoic acid of the invention is characterized by having an X-ray powder diffractogram that comprises further characteristic peaks at 4.6, 15.1 and 16.6±0.3 degrees 2 theta (Cu—$K_\alpha$ radiation, $\lambda$=1.5406 Å).

More specifically, the cocrystal of beta-sitosterol and 3,4-dihydroxybenzoic acid of the invention is characterized by exhibiting in the X-ray powder diffractogram a pattern of peaks, expressed in 2 theta units in degrees, 2θ(°), which is shown in Table 8.

TABLE 8

List of selected peaks (only peaks with relative intensity greater than or equal to 1% are indicated):

| Pos. [°2Th.] | d-spacing [Å] | Rel. Int. [%] |
|---|---|---|
| 2.275 | 38.83383 | 100 |
| 4.5724 | 19.32593 | 4.71 |
| 7.7822 | 11.36059 | 1.54 |
| 10.4054 | 8.50176 | 2.91 |
| 11.4866 | 7.70385 | 2.65 |
| 12.6094 | 7.02025 | 2.76 |
| 12.8185 | 6.90621 | 3.14 |
| 15.0479 | 5.8877 | 26.01 |
| 15.3265 | 5.78129 | 10.77 |
| 15.8782 | 5.58163 | 8.13 |
| 16.5602 | 5.35327 | 21.14 |
| 16.8087 | 5.27468 | 10.12 |
| 17.0399 | 5.20361 | 2.63 |
| 17.3535 | 5.11031 | 3.91 |
| 17.718 | 5.00599 | 6.2 |
| 17.8524 | 4.9686 | 5.1 |
| 18.1796 | 4.87989 | 1.11 |
| 18.476 | 4.80228 | 1.53 |
| 19.1125 | 4.64375 | 2.12 |
| 19.2552 | 4.60966 | 1.64 |
| 20.7989 | 4.27089 | 3.26 |
| 21.7087 | 4.09391 | 1.43 |
| 24.9792 | 3.56482 | 3.64 |
| 26.8238 | 3.32372 | 5.04 |
| 28.9457 | 3.08472 | 2.29 |

Figure 23:
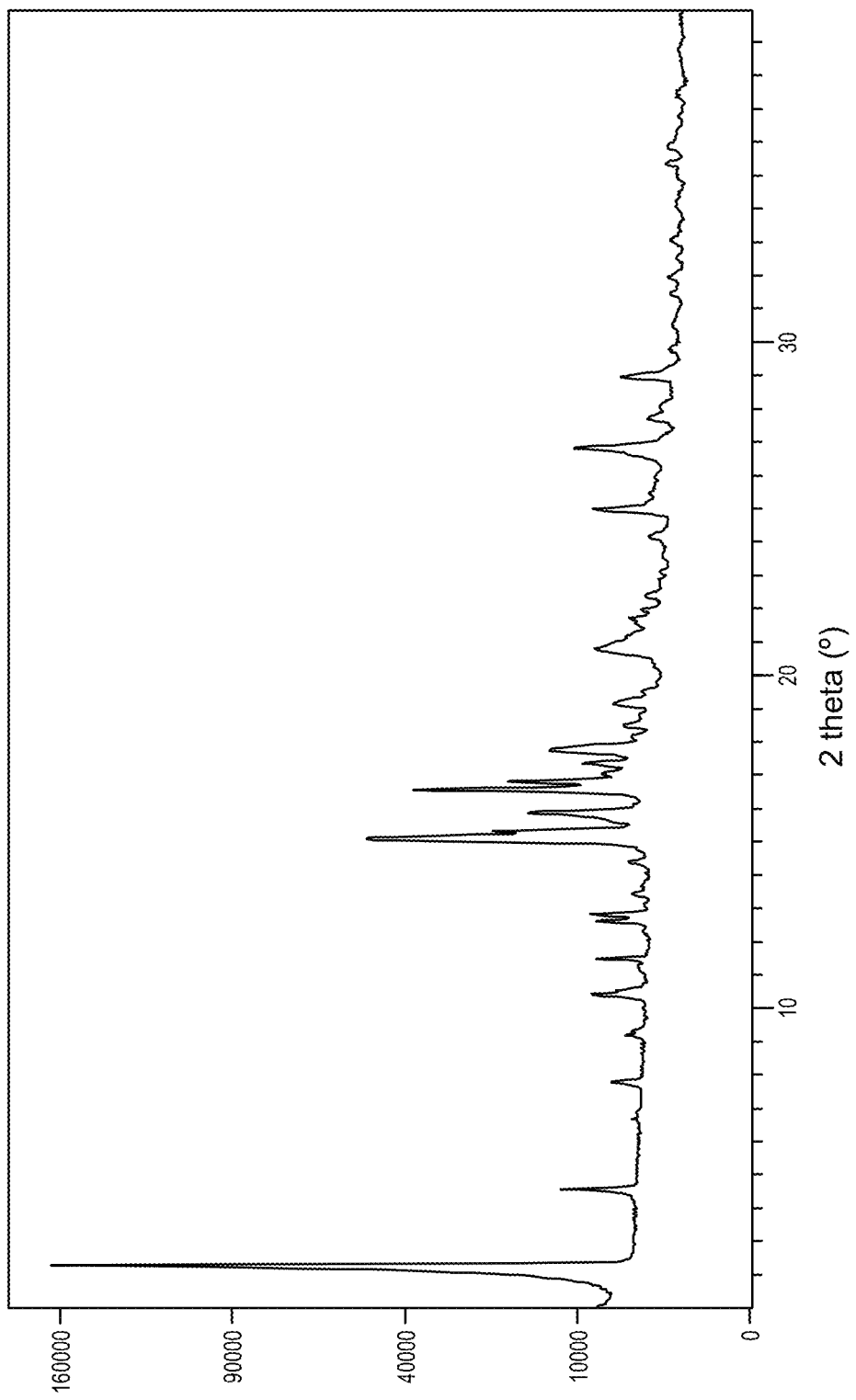
FIG. 23 shows the X-ray powder diffractogram (XRPD) of the cocrystal of beta-sitosterol and 3,4-dihydroxybenzoic acid of the present invention. The spectrum expresses intensity (I; counts) versus degrees 2 theta (°).

The cocrystal of beta-sitosterol and 3,4-dihydroxybenzoic acid of the invention may be further characterized by an X-ray diffractogram as in FIG. 23.

Figure 24:
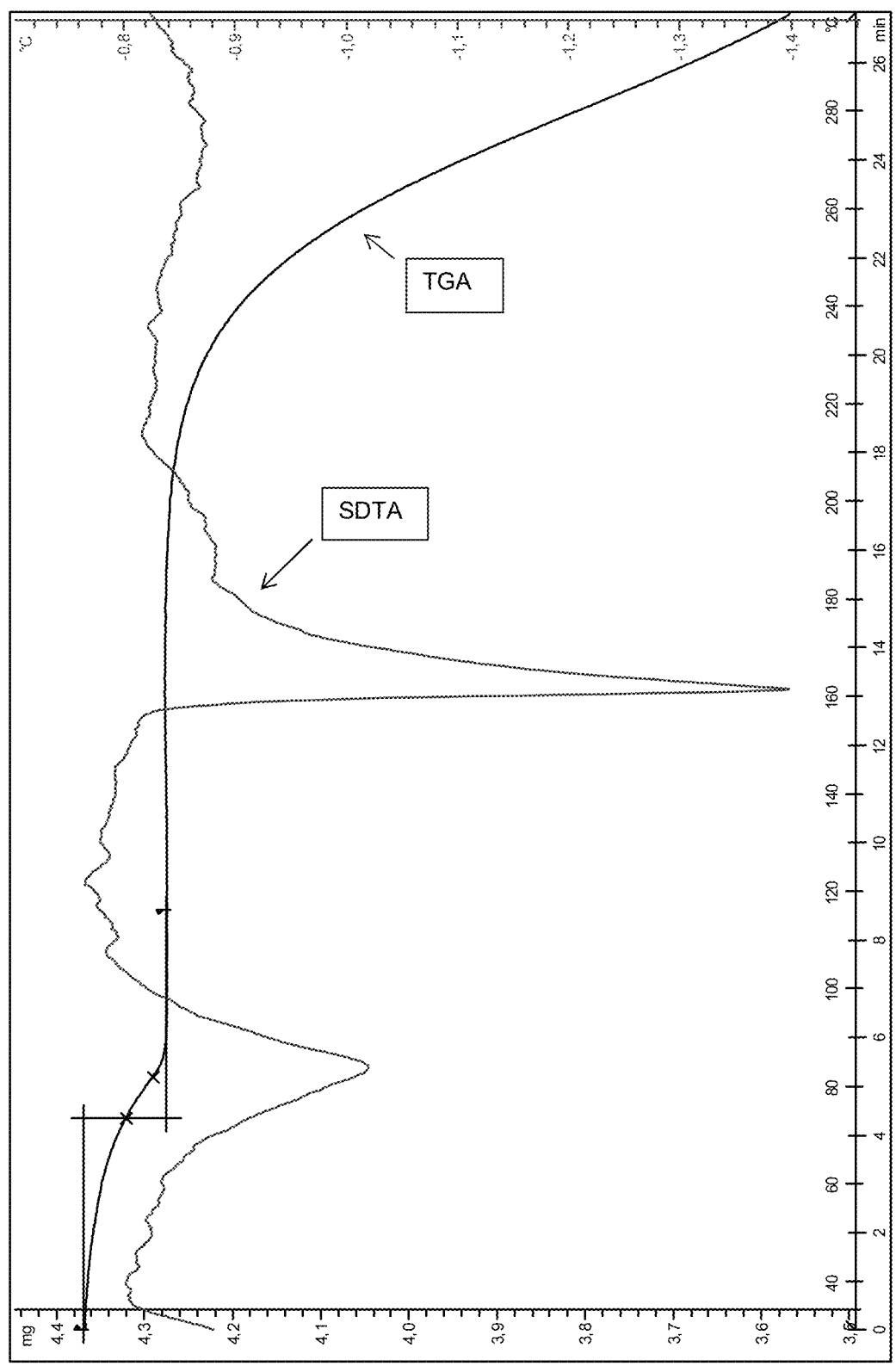
FIG. 24 shows the TGA of cocrystal of beta-sitosterol and 3,4-dihydroxybenzoic acid of the present invention. The thermogram expresses loss weight (% w/w) versus temperature (° C.).

The thermogravimetric (TG) analysis of the cocrystal of beta-sitosterol and 3,4-dihydroxybenzoic acid of the invention may also be further characterized by a weight loss of 2.1% from 29° C. to 116° C. (cf. FIG. 24).

Figure 25:
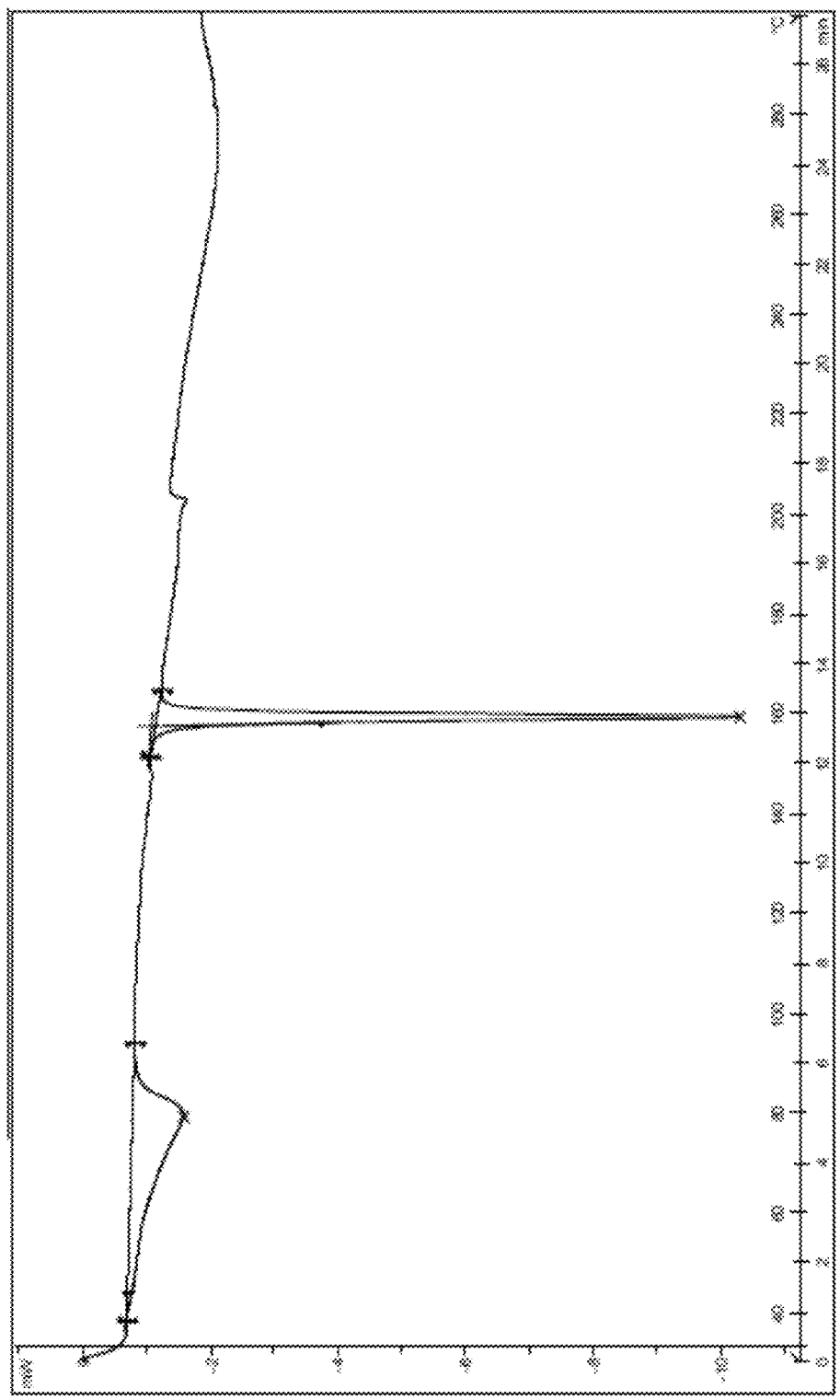
FIG. 25 shows the DSC of cocrystal of beta-sitosterol and 3,4-dihydroxybenzoic acid of the present invention. The DSC thermal curve expresses the heat flow (m/W) versus temperature (° C.).

The cocrystal of beta-sitosterol and 3,4-dihydroxybenzoic acid of the invention may also be further characterized by a first wide endothermic phenomenon at 38° C. with an associated heat of 45.4 J/g and a second endothermic phenomenon at 157° C. with an associated heat of 46.4 J/g by DSC (Differential scanning calorimetry) analysis (cf. FIG. 25).

In an embodiment, the cocrystal of beta-sitosterol and 3,4-dihydroxybenzoic acid of the formula below is in a molar ratio 1:2.

In an embodiment, the cocrystal beta-sitosterol and 3,4-dihydroxybenzoic acid is a hydrate cocrystal; preferably the cocrystal of beta-sitosterol and 3,4-dihydroxybenzoic acid is a monohydrate cocrystal having a molar ratio of beta-sitosterol: 3,4-dihydroxybenzoic acid of 1:2.

In an embodiment, the cocrystal of the invention is a cocrystal of beta-sitosterol and 3,5-dihydroxybenzoic acid. For the purposes of the invention, 3,5-dihydroxybenzoic acid has the CAS No. 99-10-5. The structure of 3,5-dihydroxybenzoic acid is the following:

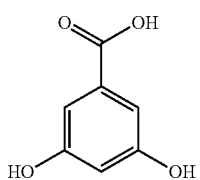

In an embodiment, the cocrystal of the invention is Form A of a cocrystal of beta-sitosterol and 3,5-dihydroxybenzoic acid named Form 8.

In an embodiment, Form A of the cocrystal of beta-sitosterol and 3,5-dihydroxybenzoic acid of the present invention is characterized by having an X-ray powder diffractogram that comprises characteristic peaks at 10.7 and 15.9±0.3 degrees 2 theta (Cu—$K_\alpha$ radiation, λ=1.5406 Å). In an embodiment, Form A of the cocrystal of beta-sitosterol and 3,5-dihydroxybenzoic acid of the invention is characterized by having an X-ray powder diffractogram that comprises further characteristic peaks at 13.4, 16.3 and 17.9±0.3 degrees 2 theta (Cu—$K_\alpha$ radiation, λ=1.5406 Å).

More specifically, Form A of the cocrystal of beta-sitosterol and 3,5-dihydroxybenzoic acid of the invention is characterized by exhibiting in the X-ray powder diffractogram a pattern of peaks, expressed in 2 theta units in degrees, 2θ(°), which is shown in Table 9.

TABLE 9

List of selected peaks (only peaks with relative intensity greater than or equal to 1% are indicated):

| Pos. [°2Th.] | d-spacing [Å] | Rel. Int. [%] |
|---|---|---|
| 2.4308 | 36.34605 | 100 |
| 4.8689 | 18.14986 | 5.99 |
| 9.2358 | 9.57563 | 4.27 |
| 10.7473 | 8.23203 | 5.59 |
| 11.8836 | 7.44735 | 9.44 |
| 12.1934 | 7.25884 | 3.17 |
| 13.3661 | 6.62449 | 3.47 |
| 13.6044 | 6.50897 | 2.05 |
| 14.3623 | 6.16716 | 58.1 |
| 14.6719 | 6.0377 | 3.59 |
| 15.0239 | 5.89705 | 9.8 |
| 15.2552 | 5.80813 | 9.43 |
| 15.8923 | 5.57672 | 16.09 |
| 16.2695 | 5.44826 | 2.97 |
| 16.8475 | 5.26263 | 14.2 |
| 17.1121 | 5.18183 | 7.52 |
| 17.3355 | 5.11556 | 23.46 |
| 17.8852 | 4.95954 | 17.75 |
| 18.7429 | 4.73449 | 8.81 |
| 20.1313 | 4.41098 | 3.07 |
| 20.2892 | 4.37701 | 5.67 |
| 21.8469 | 4.06833 | 2.63 |
| 22.0329 | 4.0344 | 2.6 |
| 22.5655 | 3.94036 | 2.42 |
| 23.7947 | 3.73953 | 2.63 |
| 24.8309 | 3.58577 | 2.48 |
| 24.9856 | 3.56393 | 2.51 |
| 27.3408 | 3.26203 | 4.06 |

Figure 26:
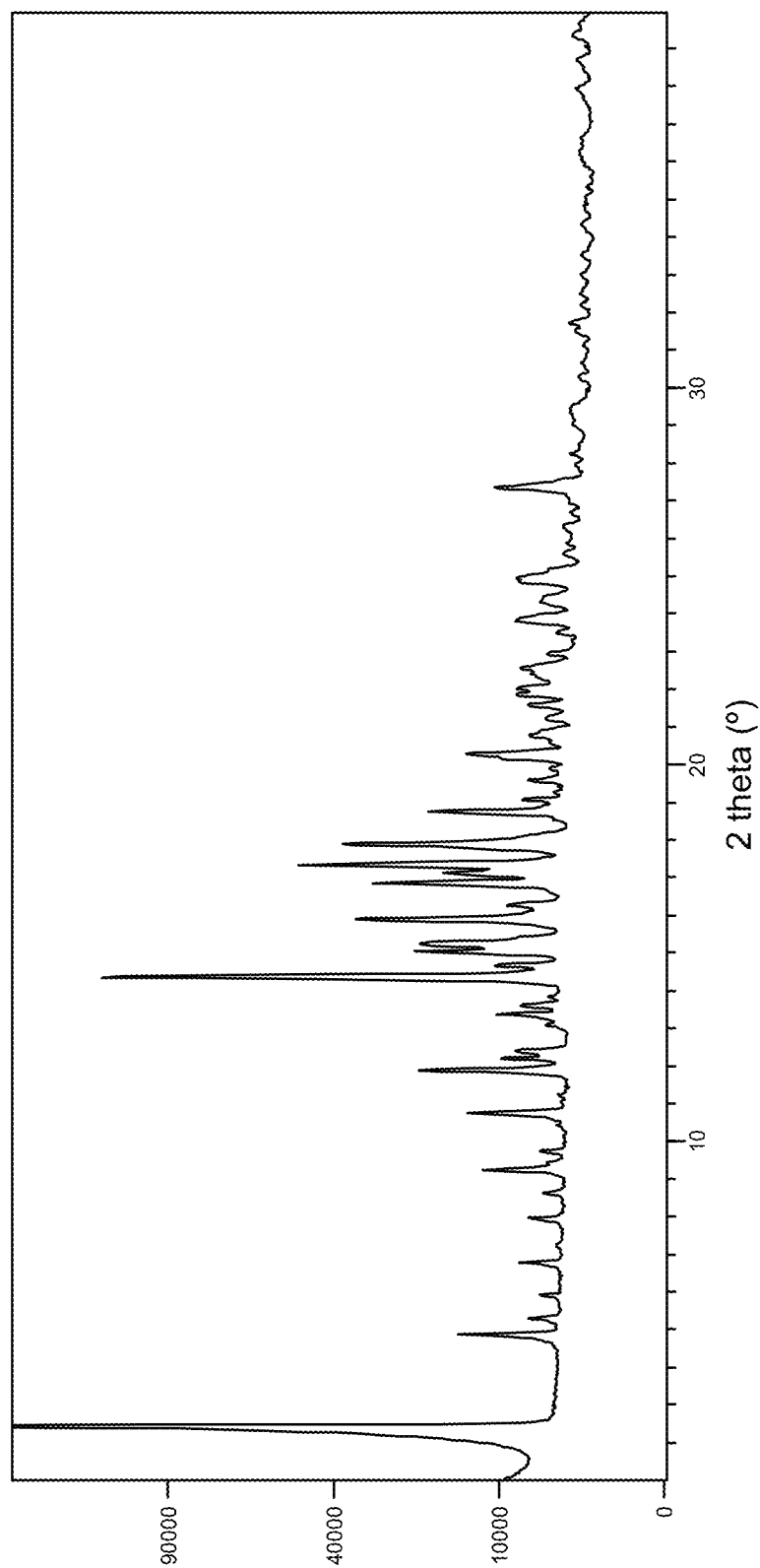
FIG. 26 shows the X-ray powder diffractogram (XRPD) of the Form A of cocrystal of beta-sitosterol and 3,5-dihydroxybenzoic acid of the present invention. The spectrum expresses intensity (I; counts) versus degrees 2 theta (°).

The Form A of the cocrystal of beta-sitosterol and 3,5-dihydroxybenzoic acid of the invention may be further characterized by an X-ray diffractogram as in FIG. 26.

Figure 27:
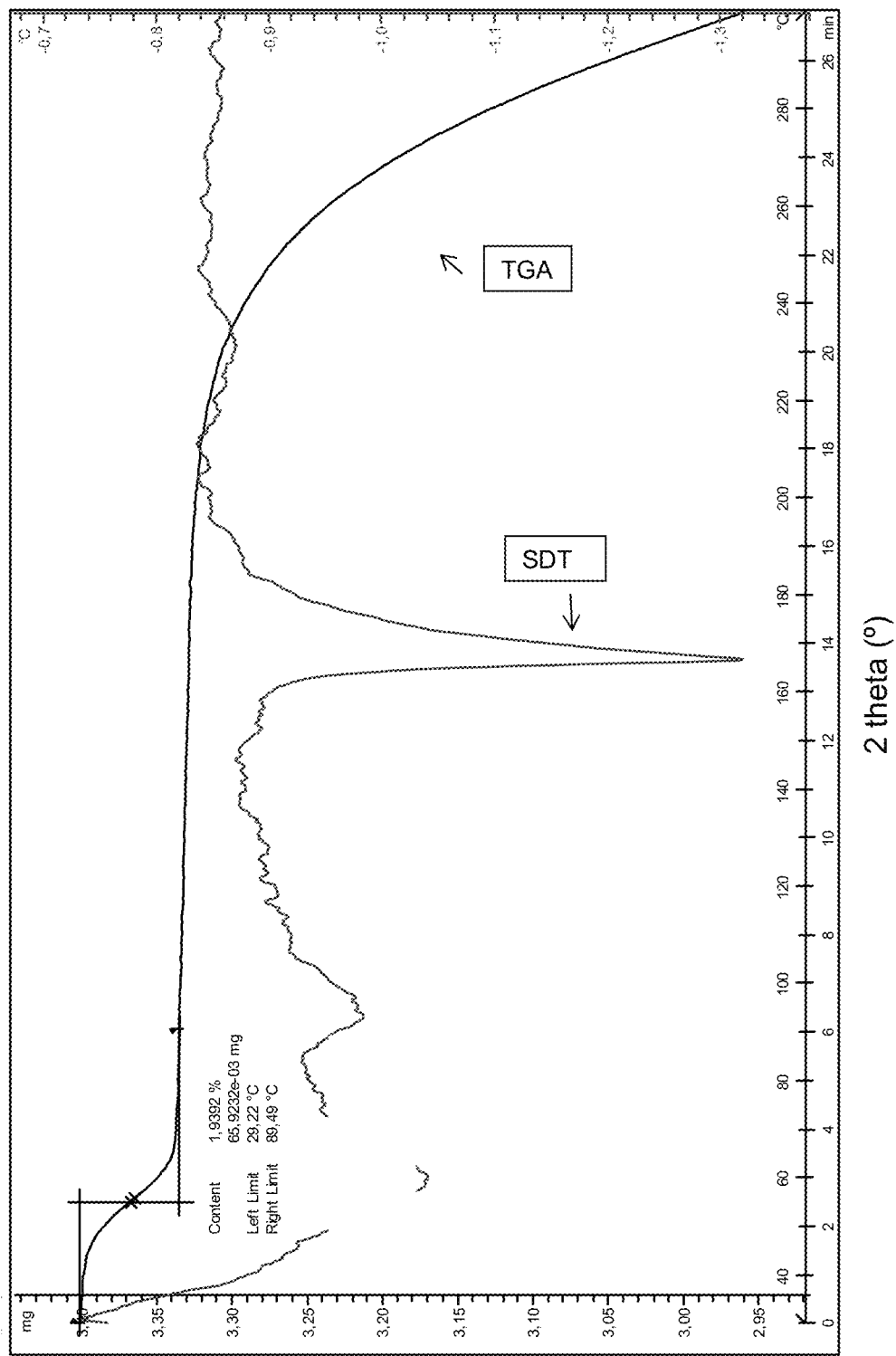
FIG. 27 shows the TGA of the Form A of cocrystal of beta-sitosterol and 3,5-dihydroxybenzoic acid of the present invention. The thermogram expresses loss weight (% w/w) versus temperature (° C.).

The thermogravimetric (TG) analysis of Form A of the cocrystal of beta-sitosterol and 3,5-dihydroxybenzoic acid of the invention may also be further characterized by a weight loss of 1.9% from 29° C. to 89° C. (cf. FIG. 27).

Figure 28:
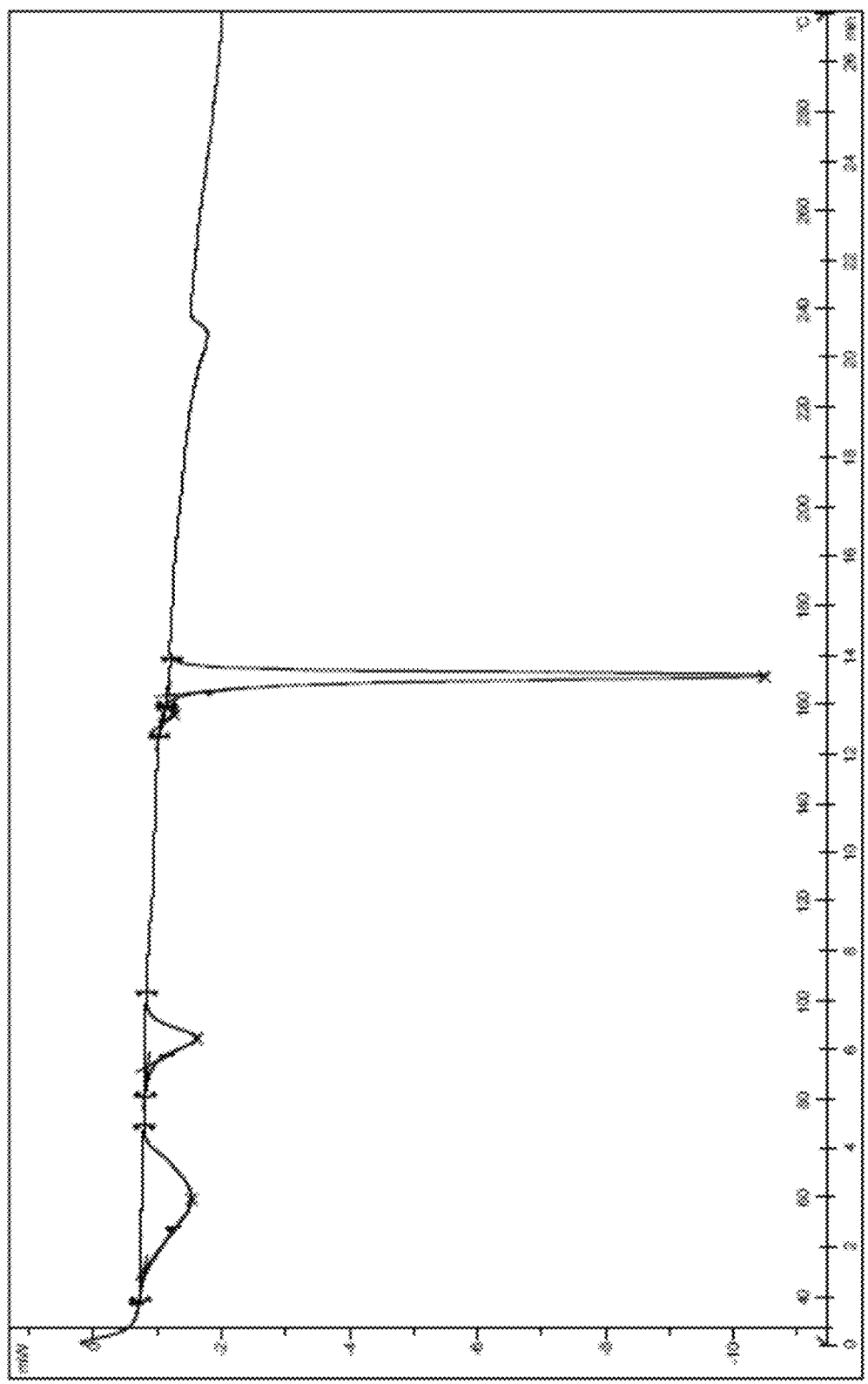
FIG. 28 shows the DSC of the Form A of cocrystal of beta-sitosterol and 3,5-dihydroxybenzoic acid Form 7 of the present invention. The DSC thermal curve expresses the heat flow (m/W) versus temperature (° C.).

The Form A of the cocrystal of beta-sitosterol and 3,5-dihydroxybenzoic acid of the invention may also be further characterized by a first wide endothermic phenomenon at 45° C. with an associated heat of 24.8 J/g, a second endothermic phenomenon at 87° C. with an associated heat of 9.6 J/g and a third endothermic phenomenon at 162° C. with an associated heat of 43.0 J/g by DSC (Differential scanning calorimetry) analysis (cf. FIG. 28).

In an embodiment, the Form A of the cocrystal of beta-sitosterol and 3,5-dihydroxybenzoic acid of the formula below is in a molar ratio 2:1.

In an embodiment, the Form A of the cocrystal beta-sitosterol and 3,5-dihydroxybenzoic acid is a hydrate cocrystal; preferably the form A of the cocrystal of beta-sitosterol and 3,5-dihydroxybenzoic acid is a monohydrate cocrystal having a molar ratio of beta-sitosterol: 3,5-dihydroxybenzoic acid of 1:1.

In an embodiment, the cocrystal of the invention is Form B of a cocrystal of beta-sitosterol and 3,5-dihydroxybenzoic acid named Form 9.

In an embodiment, Form B of the cocrystal of beta-sitosterol and 3,5-dihydroxybenzoic acid of the present invention is characterized by having an X-ray powder diffractogram that comprises characteristic peaks at 2.3 and 4.6±0.3 degrees 2 theta (Cu—$K_\alpha$ radiation, λ=1.5406 Å). In an embodiment, Form B of the cocrystal of beta-sitosterol and 3,5-dihydroxybenzoic acid of the invention is characterized by having an X-ray powder diffractogram that comprises further characteristic peaks at 10.7, 12.9 and 15.3±0.3 degrees 2 theta (Cu—$K_\alpha$ radiation, λ=1.5406 Å).

More specifically, Form B of the cocrystal of beta-sitosterol and 3,5-dihydroxybenzoic acid of the invention is characterized by exhibiting in the X-ray powder diffractogram a pattern of peaks, expressed in 2 theta units in degrees, 2θ(°), which is shown in Table 10.

TABLE 10

List of selected peaks (only peaks with relative intensity greater than or equal to 1% are indicated):

| Pos. [°2Th.] | d-spacing [Å] | Rel. Int. [%] |
|---|---|---|
| 2.2991 | 38.42698 | 100 |
| 2.8069 | 31.47683 | 1.75 |
| 4.6113 | 19.1632 | 9.97 |
| 4.8859 | 18.08678 | 1.14 |
| 5.353 | 16.50941 | 1.04 |
| 5.9147 | 14.94276 | 1.44 |
| 10.7452 | 8.2337 | 7.44 |
| 12.9175 | 6.85353 | 4.78 |
| 13.1276 | 6.74429 | 4.21 |
| 13.641 | 6.49159 | 1.85 |
| 15.2606 | 5.80611 | 50.97 |
| 15.9099 | 5.57059 | 10.29 |
| 16.2102 | 5.46806 | 21.53 |
| 16.3535 | 5.42047 | 15.54 |
| 16.5177 | 5.36695 | 10.01 |
| 16.819 | 5.27147 | 13.59 |
| 18.1284 | 4.89357 | 3.93 |
| 18.6588 | 4.75565 | 3.01 |
| 18.9165 | 4.69142 | 2.18 |
| 20.9296 | 4.24452 | 3.85 |
| 21.2383 | 4.18352 | 2.61 |
| 21.5985 | 4.11454 | 3.29 |
| 21.9679 | 4.04618 | 1.05 |
| 25.7884 | 3.45478 | 1.12 |

Figure 29:
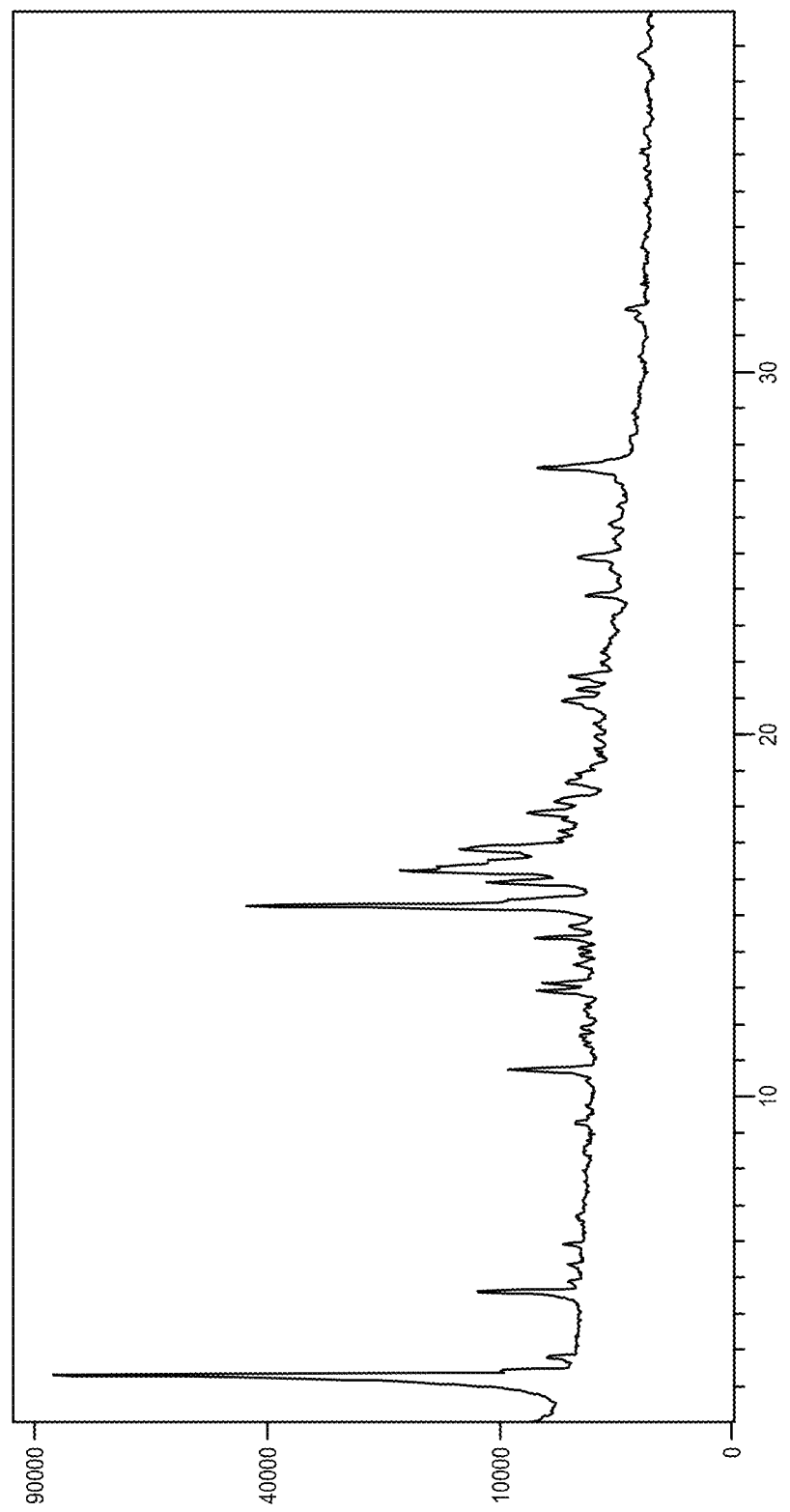
FIG. 29 shows the X-ray powder diffractogram (XRPD) of the Form B of cocrystal of beta-sitosterol and 3,5-dihydroxybenzoic acid of the present invention. The spectrum expresses intensity (I; counts) versus degrees 2 theta (°).

The Form B of the cocrystal of beta-sitosterol and 3,5-dihydroxybenzoic acid of the invention may be further characterized by an X-ray diffractogram as in FIG. 29.

Figure 30:
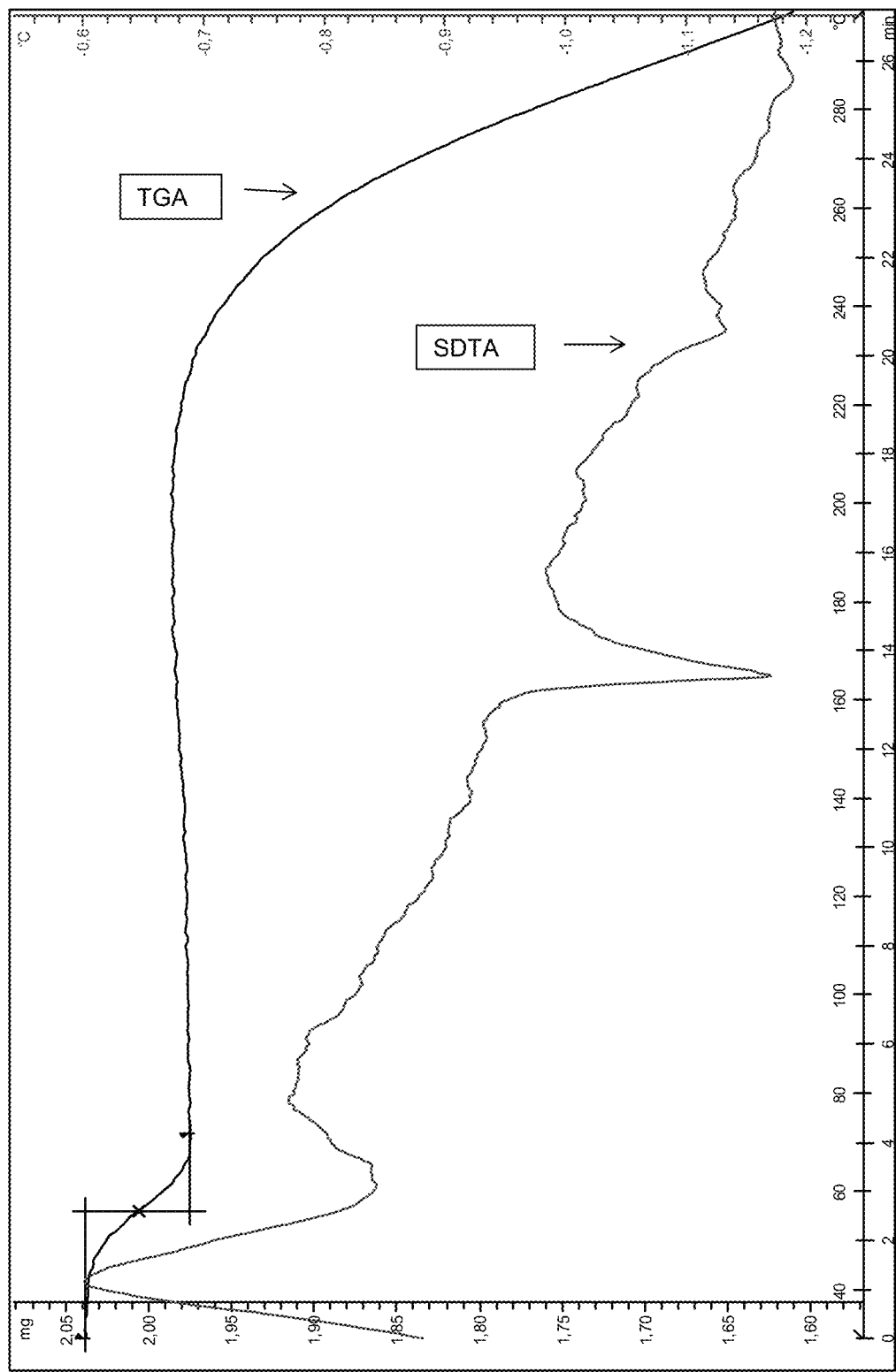
FIG. 30 shows the TGA of the Form B of cocrystal of beta-sitosterol and 3,5-dihydroxybenzoic acid of the present invention. The thermogram expresses loss weight (% w/w) versus temperature (° C.).

The thermogravimetric (TG) analysis of Form B of the cocrystal of beta-sitosterol and 3,5-dihydroxybenzoic acid of the invention may also be further characterized by a weight loss of 3.1% from 29° C. to 71° C. (cf. FIG. 30).

Figure 31:
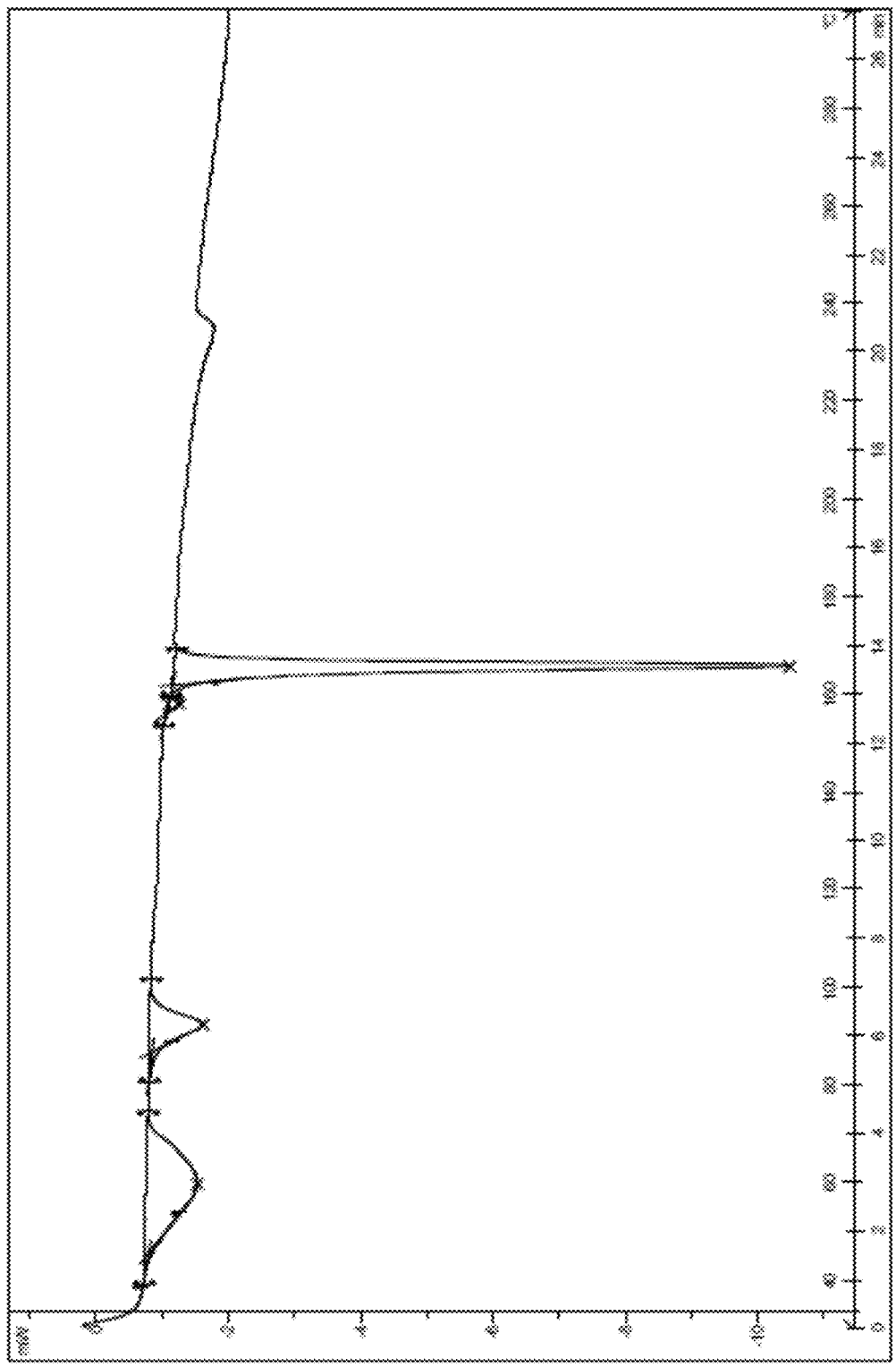
FIG. 31 shows the DSC of the Form B of cocrystal of beta-sitosterol and 3,5-dihydroxybenzoic acid of the present invention. The DSC thermal curve expresses the heat flow (m/W) versus temperature (° C.).

The Form B of the cocrystal of beta-sitosterol and 3,5-dihydroxybenzoic acid of the invention may also be further characterized by a first wide endothermic phenomenon at 48° C. with an associated heat of 40.7 J/g, a second endothermic phenomenon at 162° C. with an associated heat of 39.7 J/g and a third endothermic phenomenon at 231° C. with an associated heat of 17.2 J/g by DSC (Differential scanning calorimetry) analysis (cf. FIG. 31).

In an embodiment, the Form B of the cocrystal of beta-sitosterol and 3,5-dihydroxybenzoic acid of the formula below is in a molar ratio 1:1.

In an embodiment, the Form B of the cocrystal beta-sitosterol and 3,5-dihydroxybenzoic acid is a hydrate cocrystal; preferably the form B of the cocrystal of beta-sitosterol and 3,5-dihydroxybenzoic acid is a monohydrate cocrystal having a molar ratio of beta-sitosterol: 3,5-dihydroxybenzoic acid of 1:1.

In an embodiment, the cocrystal of the invention is a cocrystal of beta-sitosterol and 3-hydroxybenzoic acid named cocrystal Form 10. For the purposes of the invention, 3-hydroxybenzoic acid has the CAS No. 99-06-9. The structure of 3-hydroxybenzoic acid is the following:

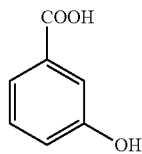

In an embodiment, the cocrystal of beta-sitosterol and 3-hydroxybenzoic acid of the present invention is characterized by having an X-ray powder diffractogram that comprises characteristic peaks at 4.6 and 12.9±0.3 degrees 2 theta (Cu—K$_\alpha$ radiation, λ=1.5406 Å). In an embodiment, the cocrystal of beta-sitosterol and 3-hydroxybenzoic acid of the invention is characterized by having an X-ray powder diffractogram that comprises further characteristic peaks at 11.6, 13.3 and 15.2±0.3 degrees 2 theta (Cu—K$_\alpha$ radiation, λ=1.5406 Å).

More specifically, the cocrystal of beta-sitosterol and 3-hydroxybenzoic acid of the invention is characterized by exhibiting in the X-ray powder diffractogram a pattern of peaks, expressed in 2 theta units in degrees, 2θ) (°, which is shown in Table 11.

TABLE 11

List of selected peaks (only peaks with relative intensity greater than or equal to 1% are indicated):

| Pos. [°2Th.] | d-spacing [Å] | Rel. Int. [%] |
|---|---|---|
| 2.3162 | 38.14342 | 99.91 |
| 4.6441 | 19.02791 | 36.34 |
| 6.5117 | 13.57403 | 1.55 |
| 9.1386 | 9.67721 | 5.2 |
| 9.4314 | 9.37746 | 3.44 |
| 11.6312 | 7.6084 | 16.85 |
| 12.4987 | 7.08222 | 7.24 |
| 12.6689 | 6.98746 | 4.12 |
| 12.9364 | 6.84353 | 22.1 |
| 13.2956 | 6.65946 | 5.93 |
| 14.798 | 5.98653 | 100 |
| 15.1793 | 5.83701 | 48.34 |
| 15.4926 | 5.71966 | 9.73 |
| 15.8563 | 5.58928 | 4.21 |

TABLE 11-continued

List of selected peaks (only peaks with relative intensity greater than or equal to 1% are indicated):

| Pos. [°2Th.] | d-spacing [Å] | Rel. Int. [%] |
|---|---|---|
| 16.953 | 5.2301 | 4.42 |
| 18.3723 | 4.82913 | 75.83 |
| 18.6756 | 4.75139 | 27.47 |
| 18.9335 | 4.68726 | 5.9 |
| 19.6404 | 4.52011 | 3.53 |
| 20.5015 | 4.33217 | 4.56 |
| 21.5293 | 4.12762 | 3.03 |
| 21.8628 | 4.0654 | 6.65 |
| 23.247 | 3.82637 | 4.36 |
| 23.6073 | 3.76879 | 3.3 |
| 24.3827 | 3.65067 | 2.47 |
| 25.1001 | 3.54793 | 2.59 |
| 27.6787 | 3.22298 | 2.84 |
| 27.8874 | 3.19933 | 3.44 |

Figure 32:
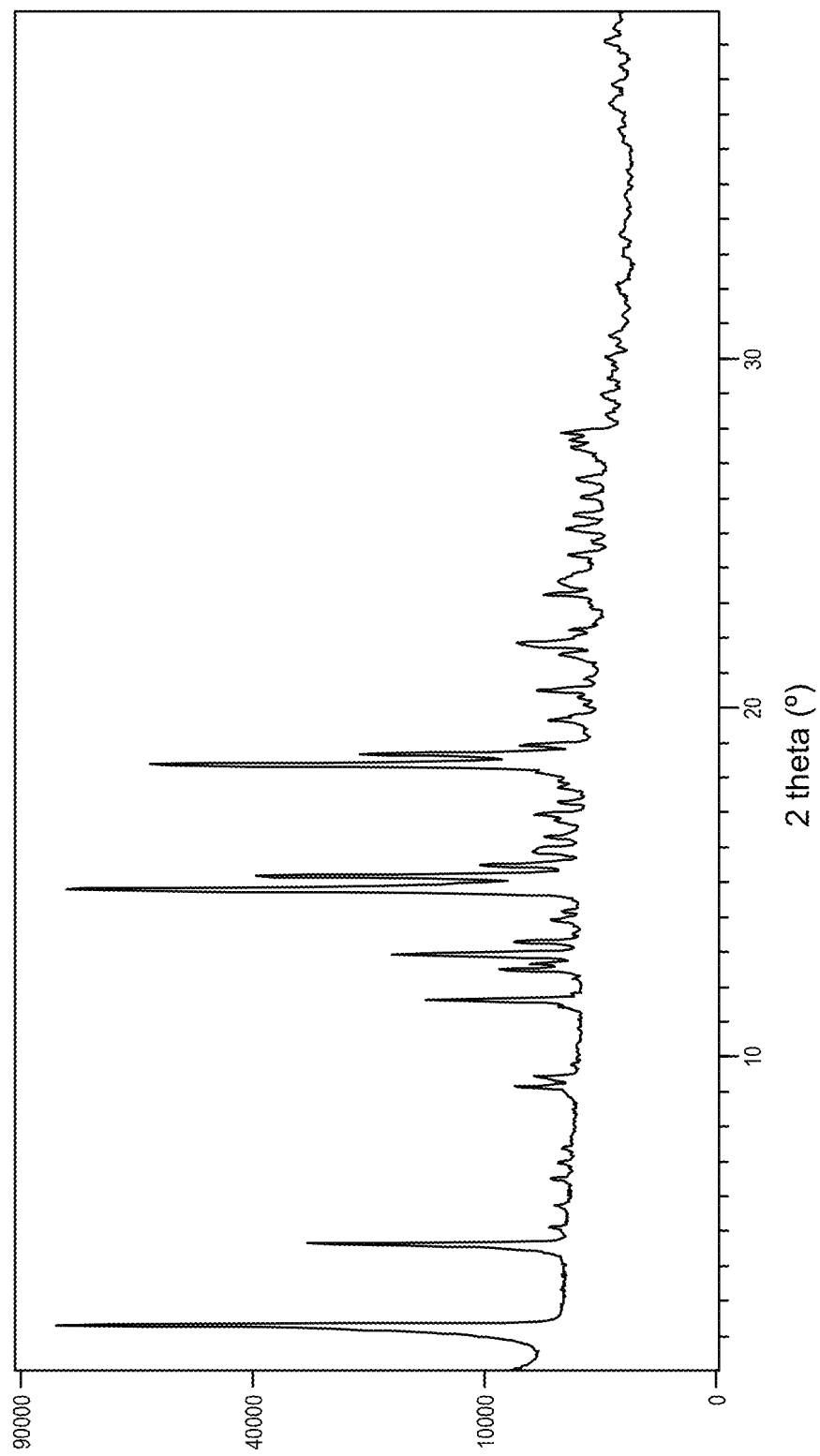
FIG. 32 shows the X-ray powder diffractogram (XRPD) of the cocrystal of beta-sitosterol and 3-hydroxybenzoic acid of the present invention. The spectrum expresses intensity (I; counts) versus degrees 2 theta (°).

The cocrystal of beta-sitosterol and 3-hydroxybenzoic acid of the invention may be further characterized by an X-ray diffractogram as in FIG. 32.

Figure 33:
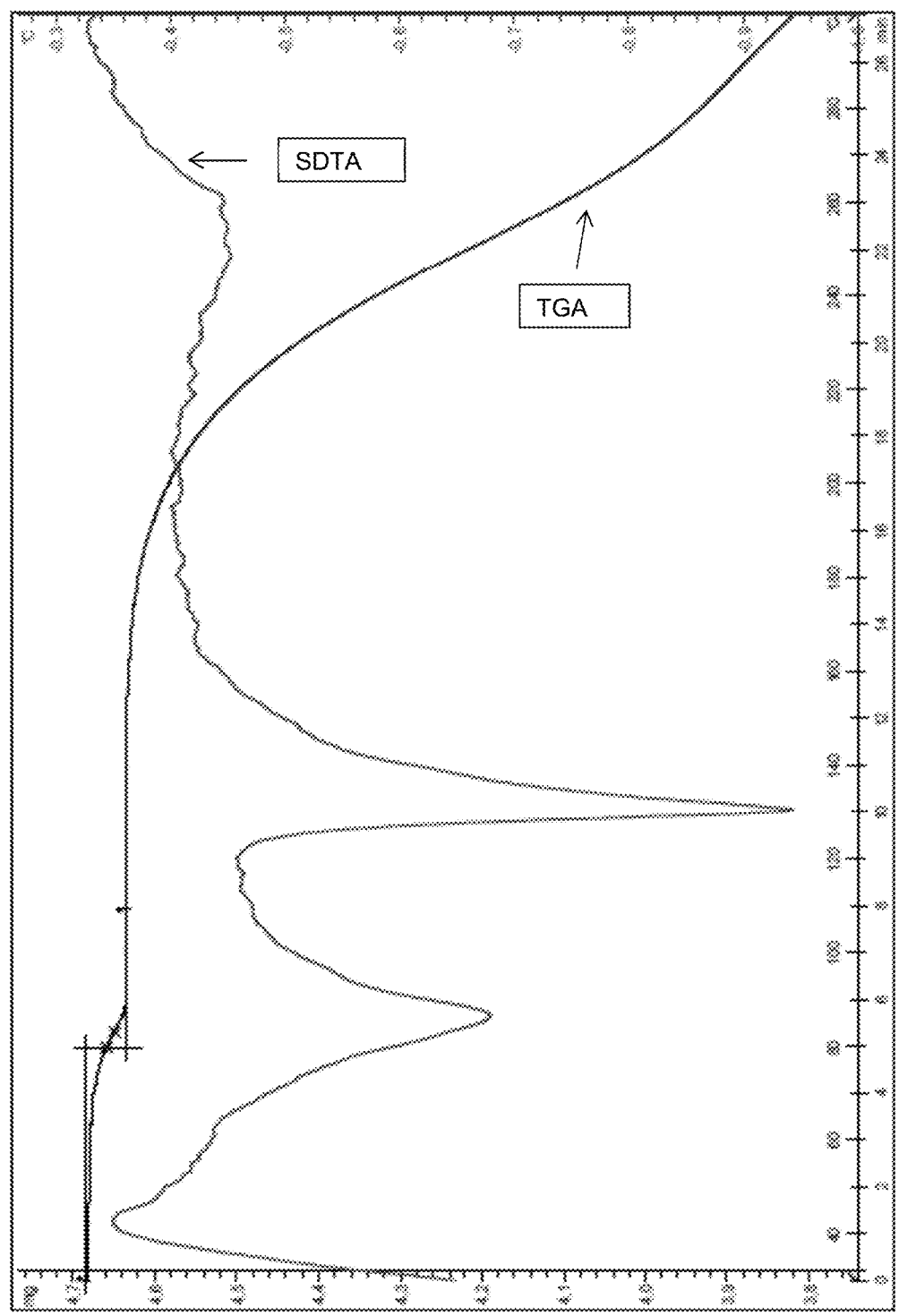
FIG. 33 shows the TGA of the cocrystal of beta-sitosterol and 3-hydroxybenzoic acid of the present invention. The thermogram expresses loss weight (% w/w) versus temperature (° C.).

The thermogravimetric (TG) analysis of the cocrystal of beta-sitosterol and 3-hydroxybenzoic acid of the invention may also be further characterized by a weight loss of 1.0% from 29° C. to 109° C. (cf. FIG. 33).

Figure 34:
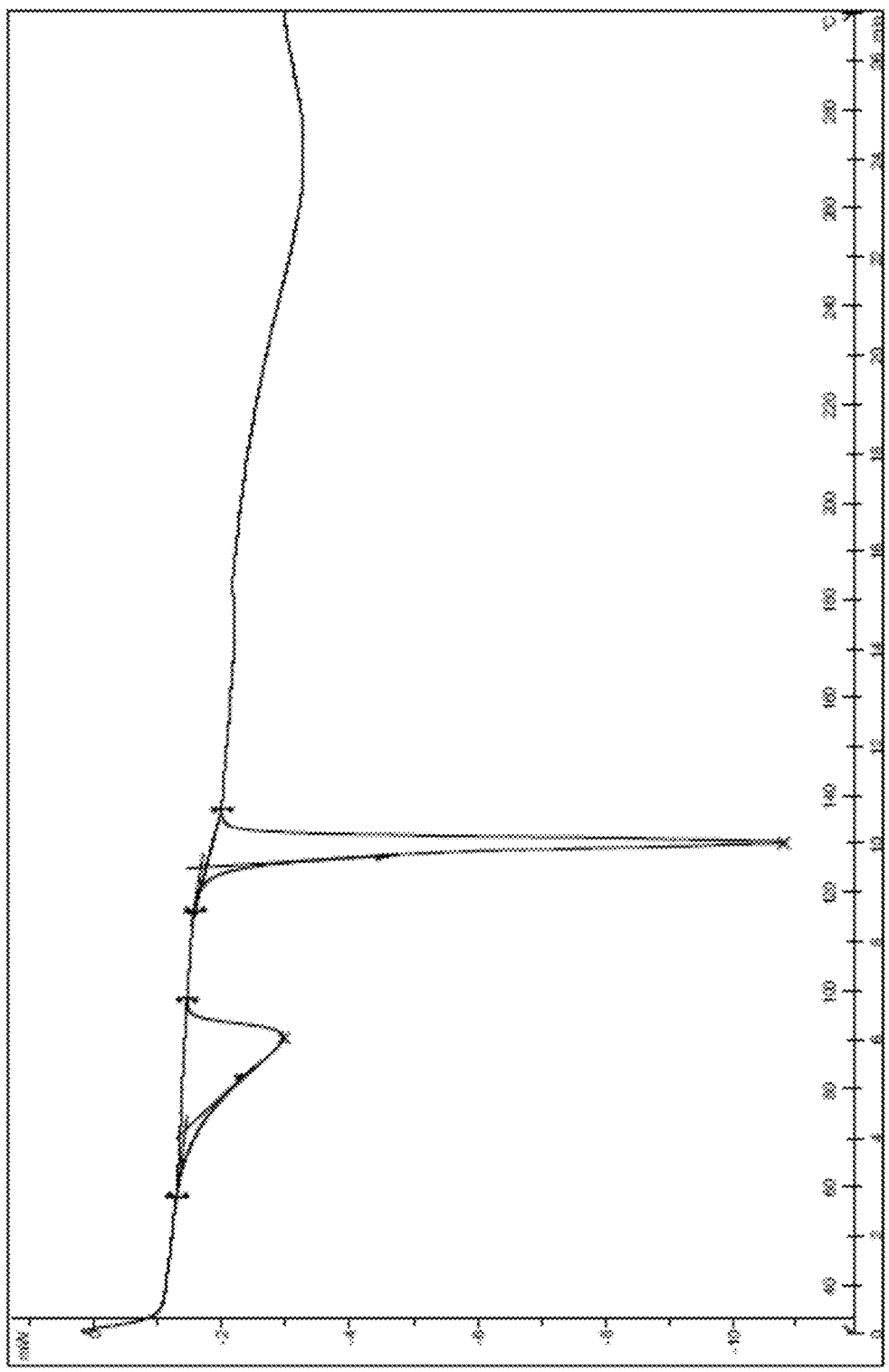
FIG. 34 shows the DSC of the cocrystal of beta-sitosterol and 3-hydroxybenzoic acid of the present invention. The DSC thermal curve expresses the heat flow (m/W) versus temperature (° C.).

The cocrystal of beta-sitosterol and 3-hydroxybenzoic acid of the invention may also be further characterized by a first wide endothermic phenomenon at 72° C. with an associated heat of 29.3 J/g and a second endothermic phenomenon at 125° C. with an associated heat of 40.1 J/g by DSC (Differential scanning calorimetry) analysis (cf. FIG. 34).

In an embodiment, the cocrystal of beta-sitosterol and 3-hydroxybenzoic acid of the formula below is in a molar ratio 2:1.

In an embodiment, the cocrystal beta-sitosterol and 3-hydroxybenzoic acid is a hydrate cocrystal; preferably the cocrystal of beta-sitosterol and 3-hydroxybenzoic acid is a monohydrate cocrystal having a molar ratio of beta-sitosterol: 3-hydroxybenzoic acid of 2:1.

In an embodiment, the cocrystal of the invention is a cocrystal of beta-sitosterol and 4-hydroxybenzoic acid. For the purposes of the invention, 4-hydroxybenzoic acid has the CAS No. 99-96-7. The structure of 4-hydroxybenzoic acid is the following:

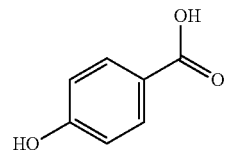

In an embodiment, the cocrystal of the invention is Form A of a cocrystal of beta-sitosterol and 4-hydroxybenzoic acid named Form 11.

In an embodiment, Form A of the cocrystal of beta-sitosterol and 4-hydroxybenzoic acid of the present invention is characterized by having an X-ray powder diffractogram that comprises characteristic peaks at 6.6 and 13.5±0.3 degrees 2 theta (Cu—K$_\alpha$ radiation, λ=1.5406 Å). In an embodiment, Form A of the cocrystal of beta-sitosterol and 4-hydroxybenzoic acid of the invention is characterized by having an X-ray powder diffractogram that comprises further characteristic peaks at 2.2, 13.1 and 14.2±0.3 degrees 2 theta (Cu—K$_\alpha$ radiation, λ=1.5406 Å).

More specifically, Form A of the cocrystal of beta-sitosterol and 4-hydroxybenzoic acid of the invention is characterized by exhibiting in the X-ray powder diffractogram a pattern of peaks, expressed in 2 theta units in degrees, 2θ(°), which is shown in Table 12.

TABLE 12

List of selected peaks (only peaks with relative intensity greater than or equal to 1% are indicated):

| Pos. [°2Th.] | d-spacing [Å] | Rel. Int. [%] |
|---|---|---|
| 2.1673 | 40.76358 | 100 |
| 4.3565 | 20.28341 | 2.66 |
| 6.5522 | 13.49029 | 6.15 |
| 8.7483 | 10.10816 | 3.31 |
| 13.1619 | 6.72678 | 4.06 |
| 13.5096 | 6.55443 | 4.71 |
| 13.8054 | 6.41468 | 2.69 |
| 14.1798 | 6.24614 | 11.71 |
| 14.4091 | 6.14723 | 15.42 |
| 14.66 | 6.04259 | 7.55 |
| 15.1652 | 5.84241 | 8.19 |
| 15.6166 | 5.67453 | 8.03 |
| 16.0751 | 5.5137 | 8.34 |
| 16.3695 | 5.4152 | 8.43 |
| 16.6052 | 5.33887 | 7.23 |
| 17.1995 | 5.1557 | 4.6 |
| 17.805 | 4.98171 | 3.27 |
| 18.4662 | 4.80481 | 3.32 |
| 19.5944 | 4.53062 | 4.77 |
| 20.4327 | 4.3466 | 3.17 |
| 20.7733 | 4.2761 | 2.6 |
| 21.2036 | 4.19028 | 2.13 |
| 22.1342 | 4.01616 | 2.11 |
| 23.7113 | 3.75249 | 2.03 |
| 26.6047 | 3.3506 | 2.91 |
| 26.8275 | 3.32327 | 2.07 |
| 27.8005 | 3.20914 | 2 |
| 28.5752 | 3.12386 | 1.16 |

Figure 35:
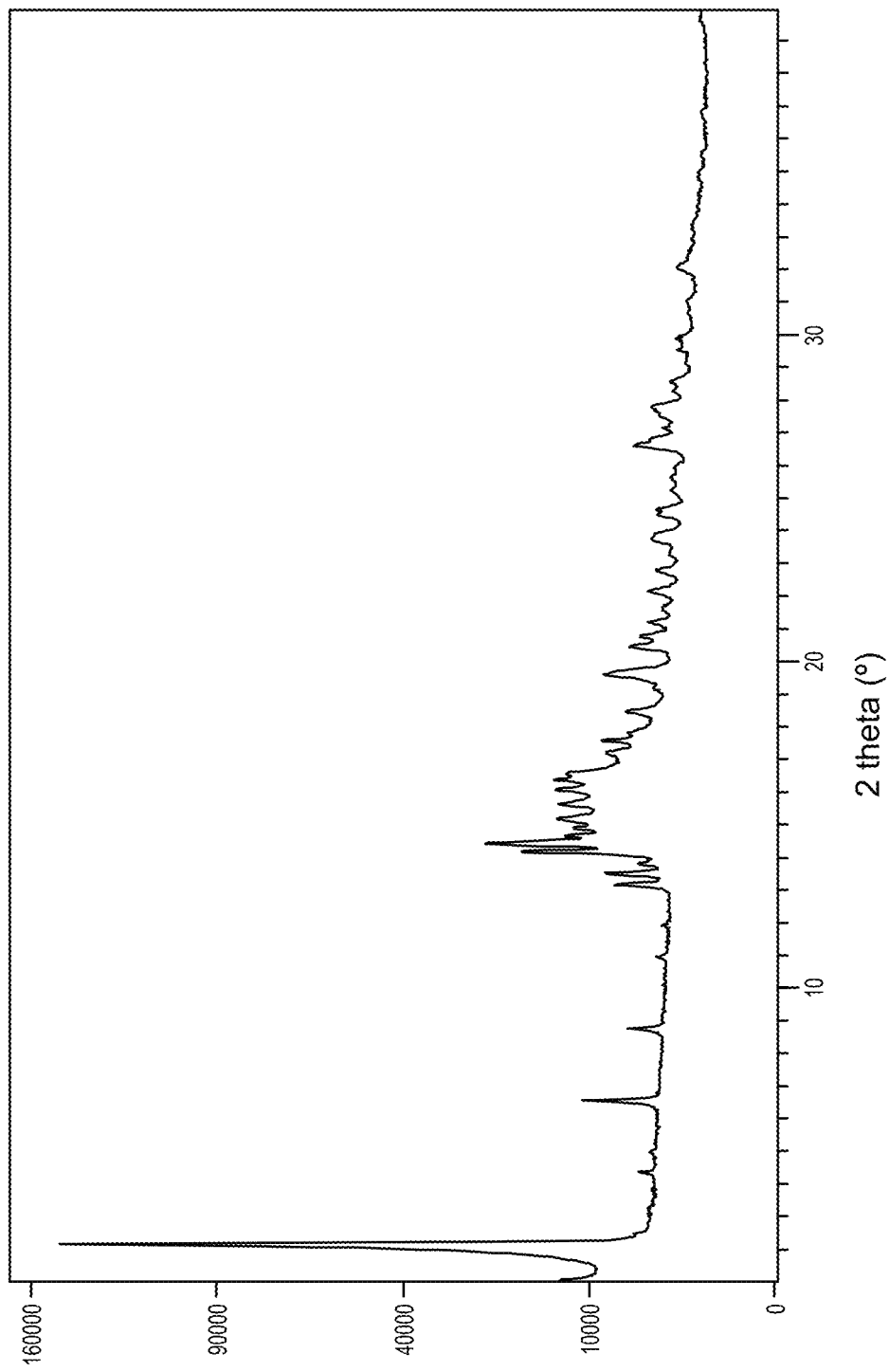
FIG. 35 shows the X-ray powder diffractogram (XRPD) of the Form A of cocrystal of beta-sitosterol and 4-hydroxybenzoic acid of the present invention. The spectrum expresses intensity (I; counts) versus degrees 2 theta (°).

The Form A of the cocrystal of beta-sitosterol and 4-hydroxybenzoic acid of the invention may be further characterized by an X-ray diffractogram as in FIG. 35.

Figure 36:
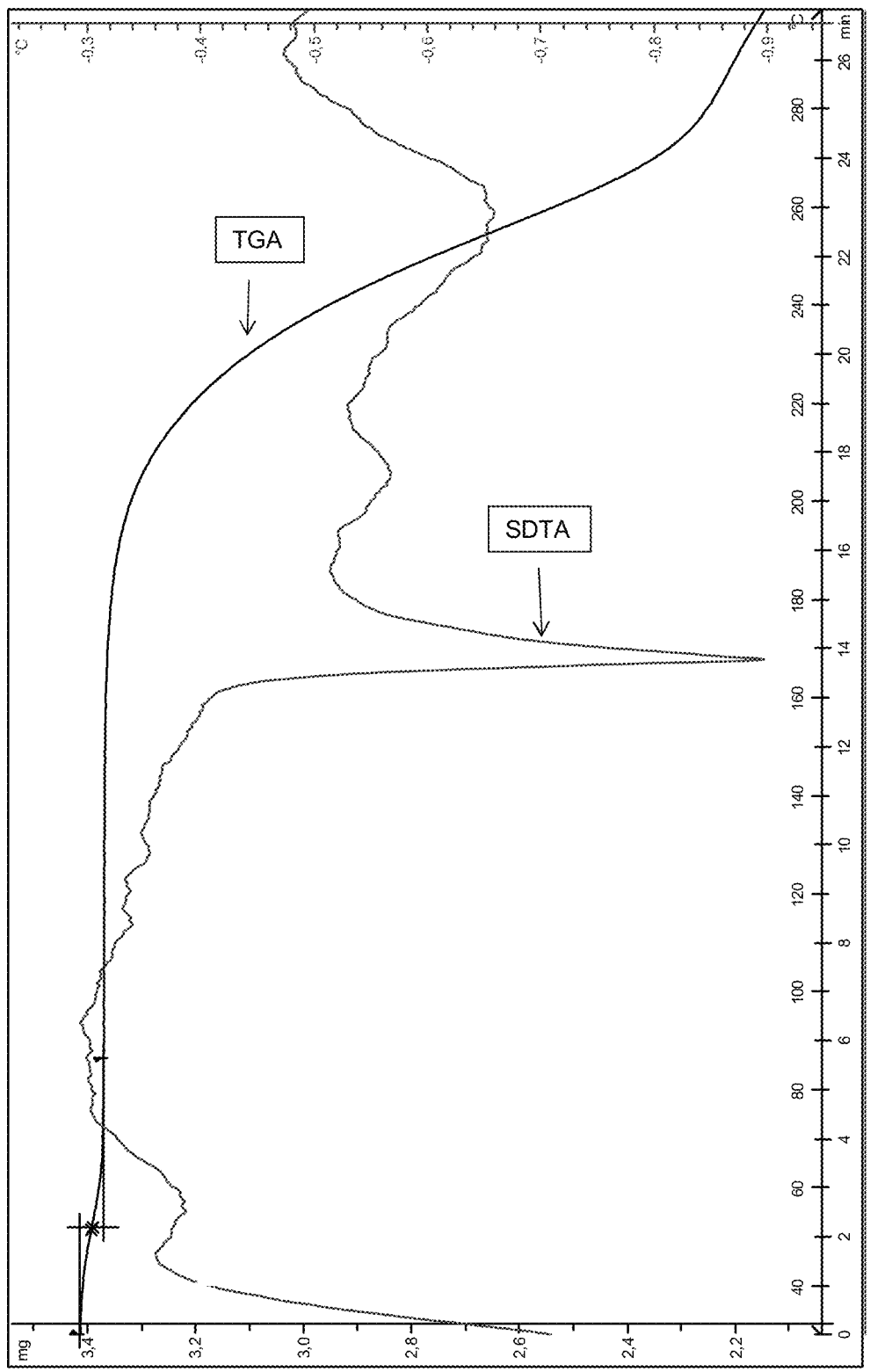
FIG. 36 shows the TGA of the Form A of cocrystal of beta-sitosterol and 4-hydroxybenzoic acid of the present invention. The thermogram expresses loss weight (% w/w) versus temperature (° C.).

The thermogravimetric (TG) analysis of Form A of the cocrystal of beta-sitosterol and 4-hydroxybenzoic acid of the invention may also be further characterized by a weight loss of 1.3% from 29° C. to 86° C. (cf. FIG. 36).

Figure 37:
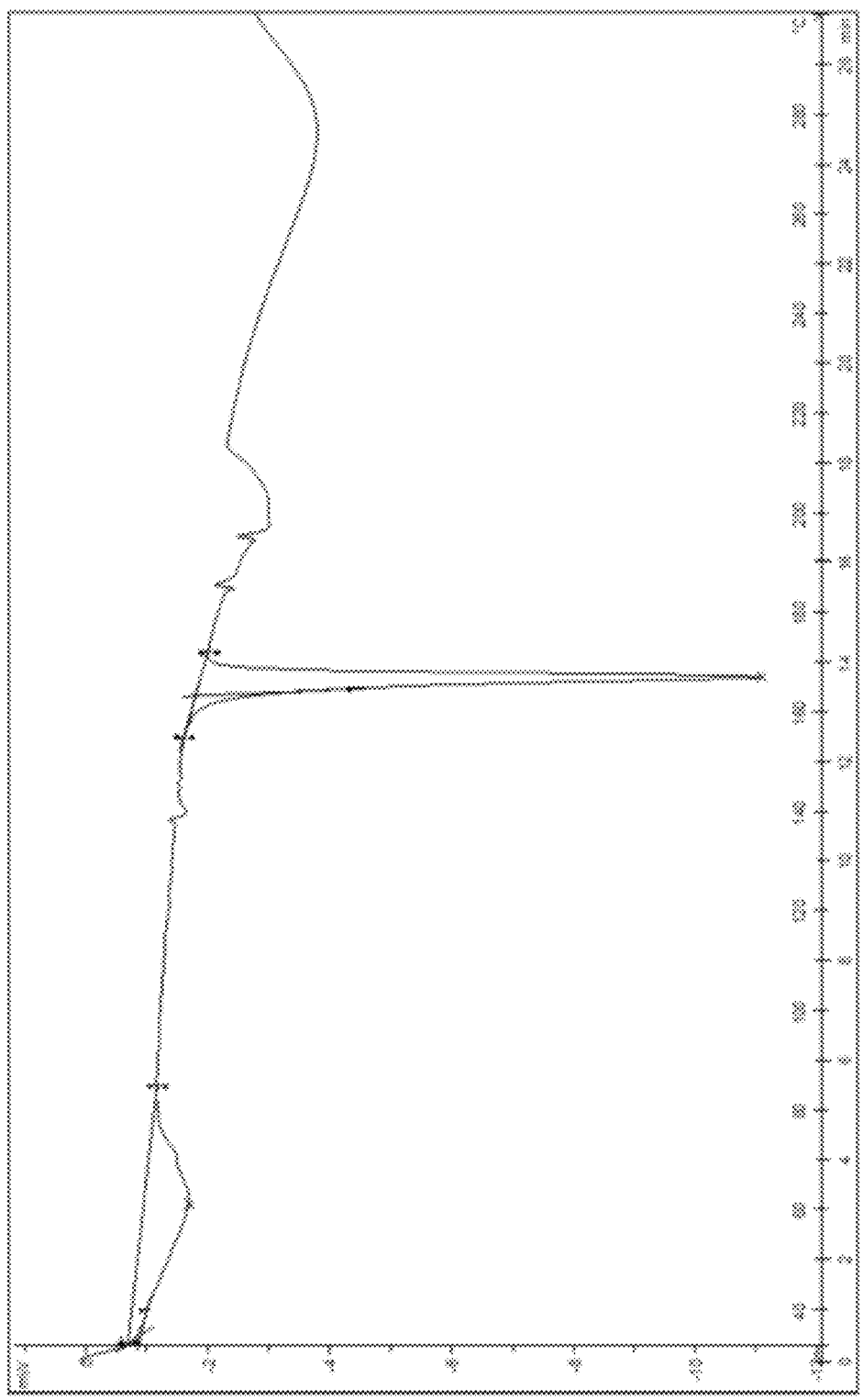
FIG. 37 shows the DSC of the Form A of cocrystal of beta-sitosterol and 4-hydroxybenzoic acid of the present invention. The DSC thermal curve expresses the heat flow (m/W) versus temperature (° C.).

The Form A of the cocrystal of beta-sitosterol and 4-hydroxybenzoic acid of the invention may also be further characterized by a first wide endothermic phenomenon at 35° C. with an associated heat of 35.1 J/g and a second endothermic phenomenon at 163° C. with an associated heat of 46.8 J/g by DSC (Differential scanning calorimetry) analysis (cf. FIG. 37).

In an embodiment, the Form A of the cocrystal of beta-sitosterol and 4-hydroxybenzoic acid of the formula below is in a molar ratio 1:1.

In an embodiment, the Form A of the cocrystal beta-sitosterol and 4-hydroxybenzoic acid is a hemi-hydrate cocrystal; preferably the form A of the cocrystal of beta-sitosterol and 4-hydroxybenzoic acid is a hemi-hydrate cocrystal having a molar ratio of beta-sitosterol: 4-hydroxybenzoic acid of 1:1.

In an embodiment, the cocrystal of the invention is Form B of a cocrystal of beta-sitosterol and 4-hydroxybenzoic acid named Form 12.

In an embodiment, Form B of the cocrystal of beta-sitosterol and 4-hydroxybenzoic acid of the present invention is characterized by having an X-ray powder diffractogram that comprises characteristic peaks at 15.8 and 17.9±0.3 degrees 2 theta (Cu—K$_\alpha$ radiation, λ=1.5406 Å).

In an embodiment, Form B of the cocrystal of beta-sitosterol and 4-hydroxybenzoic acid of the invention is characterized by having an X-ray powder diffractogram that comprises further characteristic peaks at 2.3, 12.4 and 16.8±0.3 degrees 2 theta (Cu—K$_\alpha$ radiation, λ=1.5406 Å).

More specifically, Form B of the cocrystal of beta-sitosterol and 4-hydroxybenzoic acid of the invention is characterized by exhibiting in the X-ray powder diffractogram a pattern of peaks, expressed in 2 theta units in degrees, 2θ(°), which is shown in Table 13.

TABLE 13

List of selected peaks (only peaks with relative intensity greater than or equal to 1% are indicated):

| Pos. [°2Th.] | d-spacing [Å] | Rel. Int. [%] |
|---|---|---|
| 2.3056 | 38.31897 | 100 |
| 4.6199 | 19.12744 | 5.33 |
| 7.7414 | 11.42043 | 1.68 |
| 10.4255 | 8.48546 | 1.89 |
| 11.2895 | 7.83793 | 1.02 |
| 11.5747 | 7.64538 | 2.24 |
| 12.4323 | 7.11987 | 3.2 |
| 12.6538 | 6.99574 | 5.29 |
| 14.2549 | 6.2134 | 1.65 |
| 15.0057 | 5.90414 | 68.78 |
| 15.2396 | 5.81405 | 6.93 |
| 15.617 | 5.67438 | 4.85 |
| 15.8021 | 5.60834 | 11.19 |
| 16.7797 | 5.28372 | 29.57 |
| 17.0234 | 5.20863 | 11.88 |
| 17.3974 | 5.09748 | 3.29 |
| 17.5695 | 5.04795 | 3.55 |
| 17.9296 | 4.94737 | 10.31 |
| 18.3507 | 4.83479 | 2.32 |
| 18.6592 | 4.75553 | 2.09 |
| 18.8465 | 4.70869 | 3.11 |
| 20.5099 | 4.33041 | 4.78 |
| 20.9887 | 4.2327 | 6.05 |
| 21.5872 | 4.11667 | 2.38 |
| 22.4091 | 3.96752 | 1.18 |
| 25.2733 | 3.52401 | 1.88 |
| 25.544 | 3.48727 | 0.97 |
| 26.4803 | 3.36605 | 1.77 |

Figure 38:
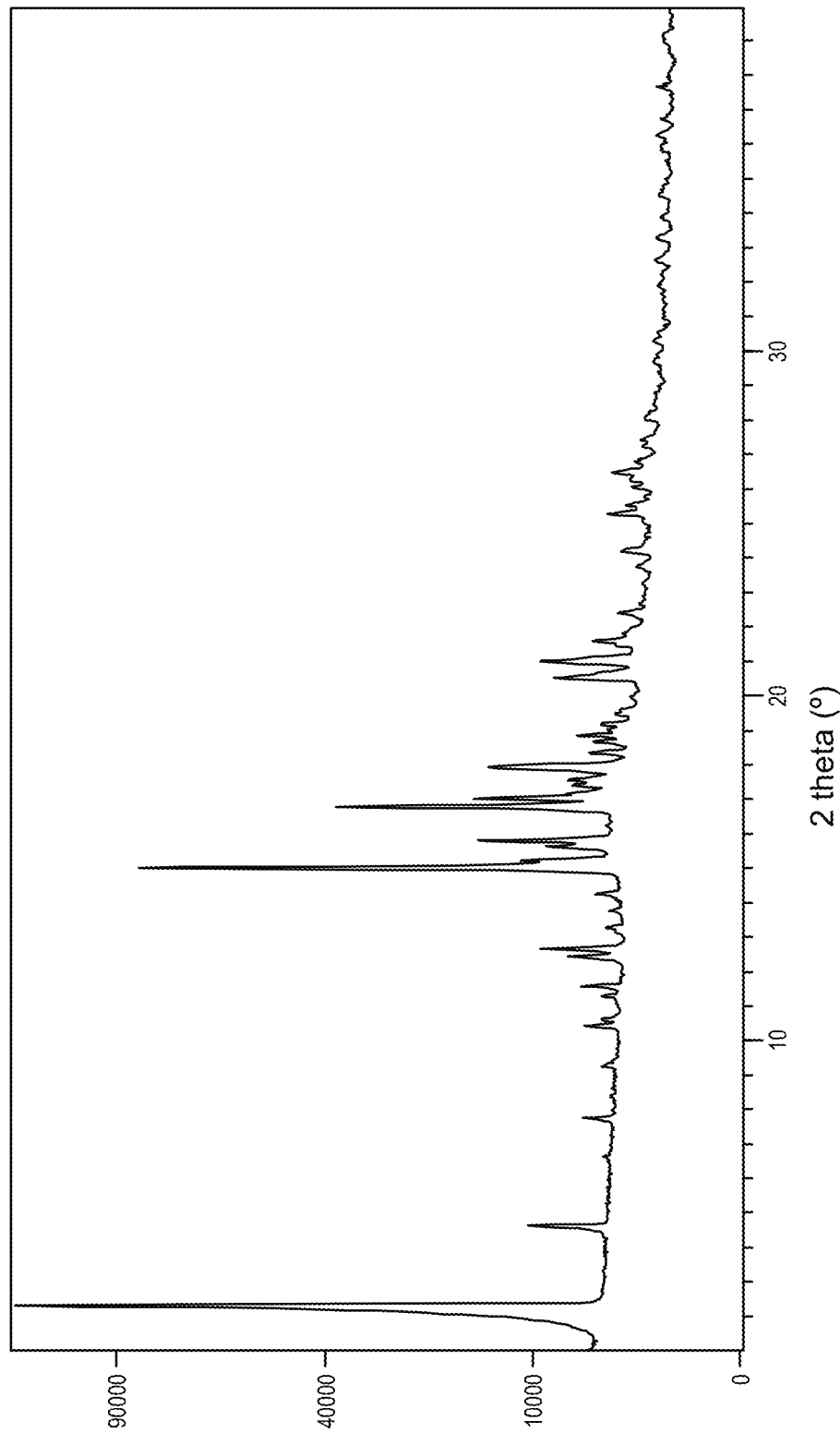
FIG. 38 shows the X-ray powder diffractogram (XRPD) of the Form B of cocrystal of beta-sitosterol and 4-hydroxybenzoic acid of the present invention. The spectrum expresses intensity (I; counts) versus degrees 2 theta (°).

The Form B of the cocrystal of beta-sitosterol and 4-hydroxybenzoic acid of the invention may be further characterized by an X-ray diffractogram as in FIG. 38.

Figure 39:
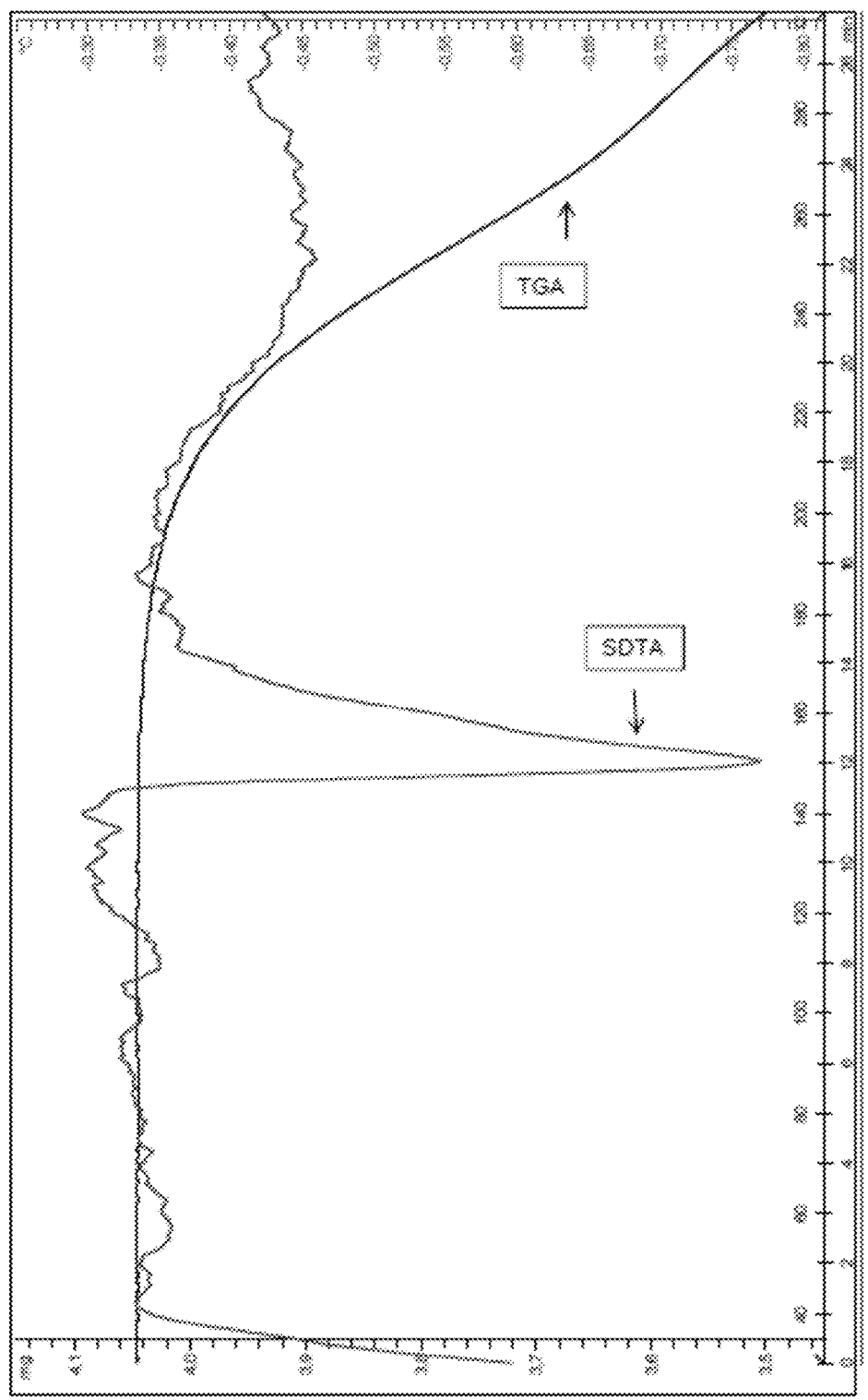
FIG. 39 shows the TGA of the Form B of cocrystal of beta-sitosterol and 4-hydroxybenzoic acid of the present invention. The thermogram expresses loss weight (% w/w) versus temperature (° C.).

The thermogravimetric (TG) analysis of Form B of the cocrystal of beta-sitosterol and 4-hydroxybenzoic acid of the invention may also be further characterized by a by a thermal melting/decomposition phenomenon starting at 145° C. (cf. FIG. 39).

Figure 40:
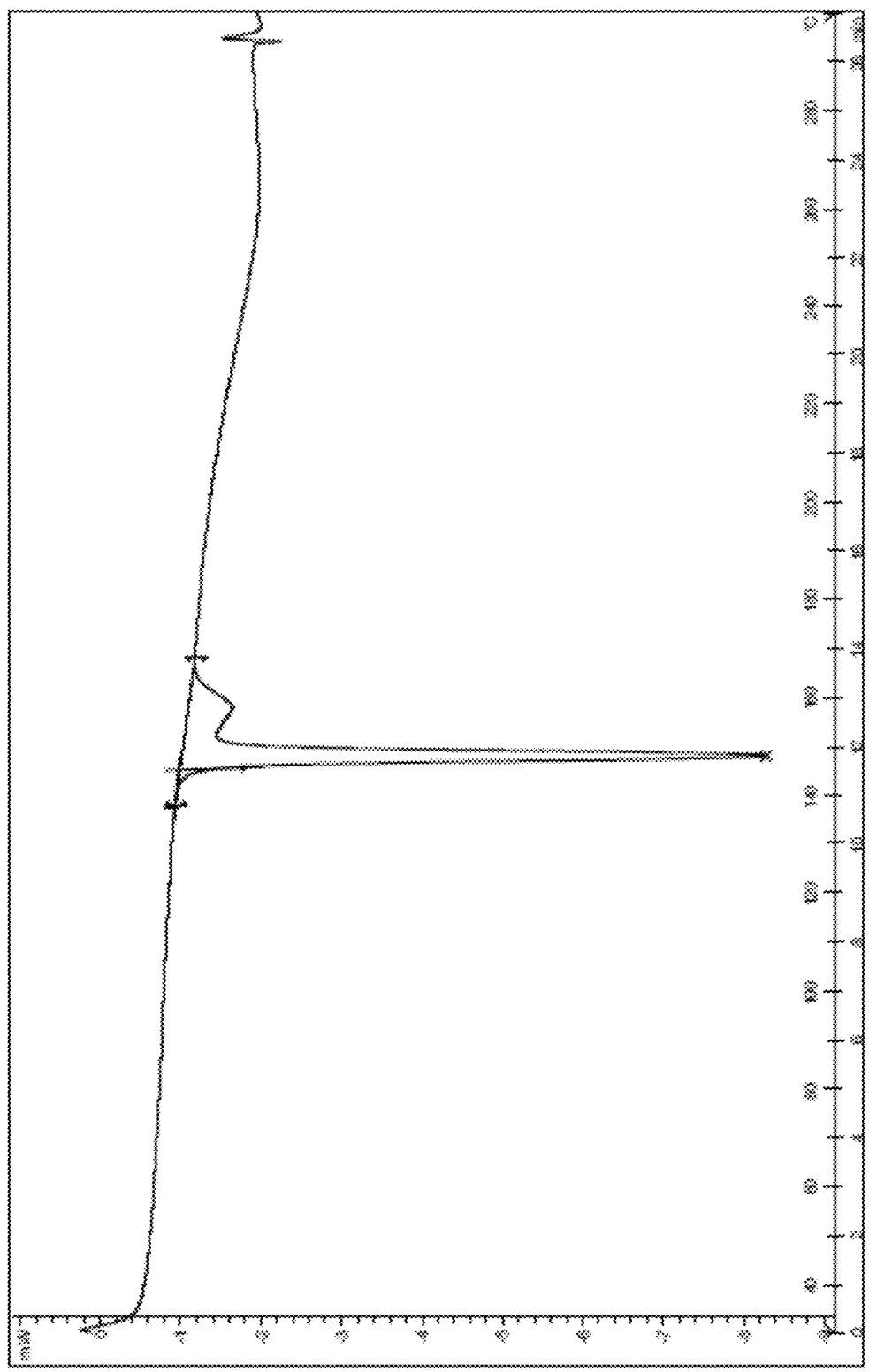
FIG. 40 shows the DSC of the Form B of cocrystal of beta-sitosterol and 4-hydroxybenzoic acid of the present invention. The DSC thermal curve expresses the heat flow (m/W) versus temperature (° C.).

The Form B of the cocrystal of beta-sitosterol and 4-hydroxybenzoic acid of the invention may also be further characterized by a wide endothermic phenomenon at 145° C. with an associated heat of 60.7 J/gby DSC (Differential scanning calorimetry) analysis (cf. FIG. 40).

In an embodiment, the Form B of the cocrystal of beta-sitosterol and 4-hydroxybenzoic acid of the formula below is in a molar ratio 1:1.

As mentioned above, the first aspect of the invention is the provision of a cocrystal of beta-sitosterol and a hydrogen bond donor coformer. In an embodiment, the cocrystal of beta-sitosterol and a hydrogen bond donor coformer is one wherein the hydrogen bond donor coformer is an organic alcohol. The term "organic alcohol" refers to an organic compound with one or more hydroxyl group. In an embodiment, the cocrystal of beta-sitosterol is one wherein the hydrogen bond donor coformer is an organic alcohol of formula $R_5CH_2OH$, wherein $R_5$ is selected from the group consisting of $(C_1-C_8)$alkyl, $(C_6-C_{12})$aryl and $(C_6-C_{12})$aryl-$(C_1-C_8)$alkyl.

In an embodiment, the cocrystal of beta-sitosterol is one wherein the hydrogen bond donor coformer is an organic alcohol selected from the group consisting of benzyl alcohol, ethanol and isopropanol.

In an embodiment, the cocrystal of the invention is a cocrystal of beta-sitosterol and benzyl alcohol named cocrystal Form 4. For the purposes of the invention, benzyl alcohol is the International Nonproprietary Name (INN) of phenyl methanol, and has the CAS No. 100-51-6. The structure of benzyl alcohol is the following:

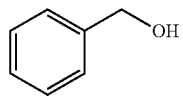

In an embodiment, the cocrystal of beta-sitosterol and benzyl alcohol of the present invention is characterized by having an X-ray powder diffractogram that comprises characteristic peaks at approximately 2.3 and 4.7±0.3 degrees 2 theta (Cu—K$_\alpha$ radiation, $\lambda$=1.5406 Å). In an embodiment, the cocrystal of beta-sitosterol and benzyl alcohol of the invention is characterized by having an X-ray powder diffractogram that comprises further characteristic peaks at 9.0, 11.7 and 15.0±0.3 degrees 2 theta (Cu—K$_\alpha$ radiation, $\lambda$=1.5406 Å).

More specifically, the cocrystal of beta-sitosterol and benzyl alcohol of the invention is characterized by exhibiting in the X-ray powder diffractogram a pattern of peaks, expressed in 2 theta units in degrees, 2θ(°), which is shown in Table 4.

TABLE 4

List of selected peaks (only peaks with relative intensity greater than or equal to 0.5% are indicated):

| Pos. [°2Th.] | d-spacing [Å] | Rel. Int. [%] |
| --- | --- | --- |
| 2.3215 | 38.05686 | 20.27 |
| 4.6563 | 18.97794 | 5.79 |
| 8.9844 | 9.84302 | 8.68 |
| 9.6372 | 9.1777 | 0.7 |
| 11.7163 | 7.55335 | 18.23 |
| 11.9733 | 7.39175 | 3.92 |
| 12.2661 | 7.21598 | 7.42 |
| 12.7622 | 6.93657 | 4.29 |
| 14.7588 | 6.00234 | 14.04 |
| 14.9572 | 5.92318 | 100 |
| 15.4167 | 5.74767 | 18.08 |
| 16.3798 | 5.4118 | 4.8 |
| 17.8551 | 4.96784 | 17.19 |
| 18.0654 | 4.91048 | 73.36 |
| 18.369 | 4.83001 | 7.37 |
| 18.5667 | 4.77903 | 9.26 |
| 19.3441 | 4.58867 | 19.64 |
| 21.1793 | 4.19502 | 5.24 |
| 21.6381 | 4.1071 | 16.28 |
| 21.8741 | 4.06333 | 7.82 |
| 26.9763 | 3.30254 | 5.12 |
| 27.2336 | 3.27192 | 3.47 |
| 38.4168 | 2.3413 | 1.19 |
| 38.9206 | 2.31214 | 1.26 |

Figure 8:
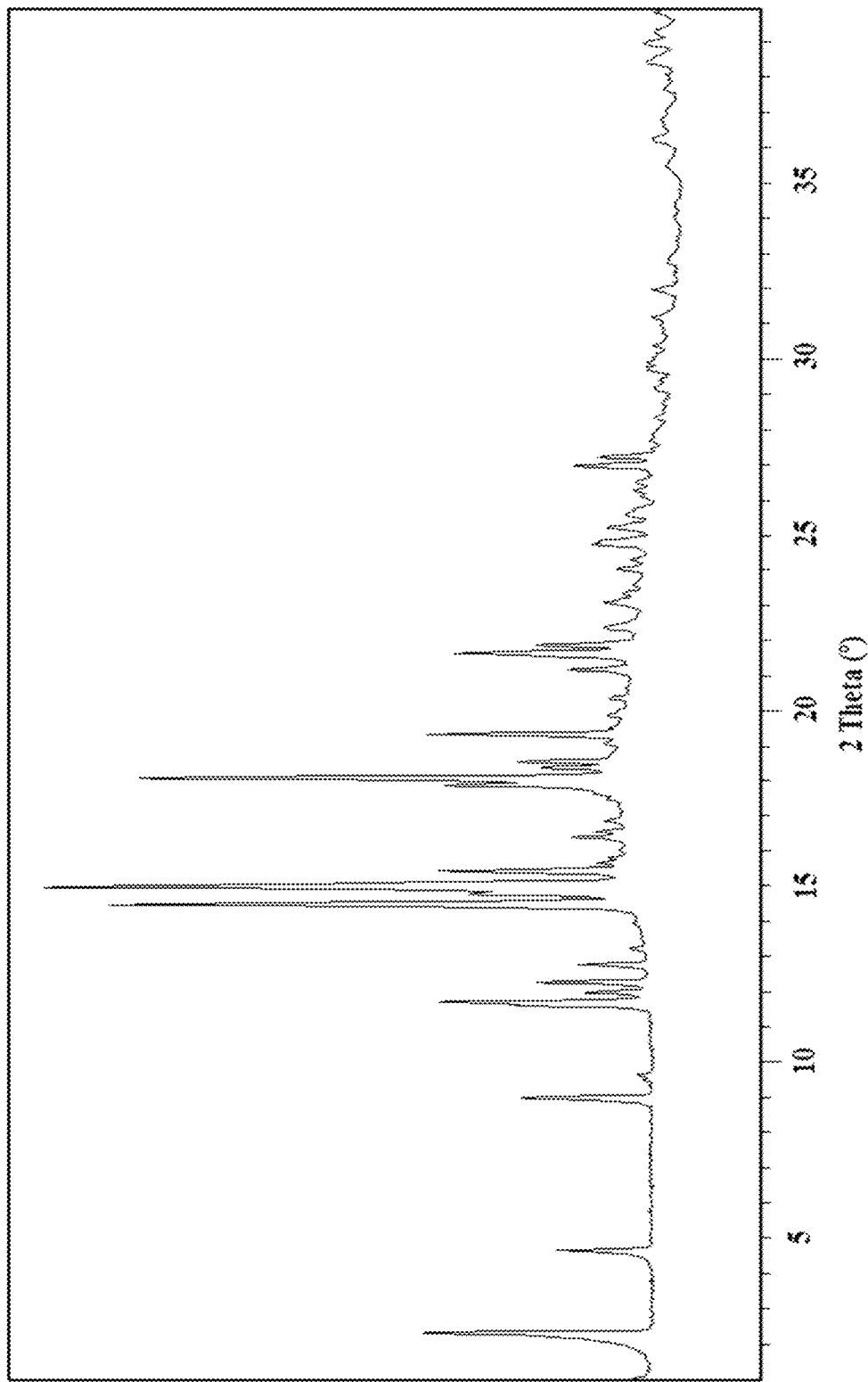
FIG. 8 shows the X-ray powder diffractogram (XRPD) of the cocrystal of beta-sitosterol and benzyl alcohol of the present invention. The spectrum expresses intensity (I; counts) versus degrees 2 theta (°).

The cocrystal of beta-sitosterol and benzyl alcohol of the invention may be further characterized by an X-ray diffractogram as in FIG. 8.

Figure 9:
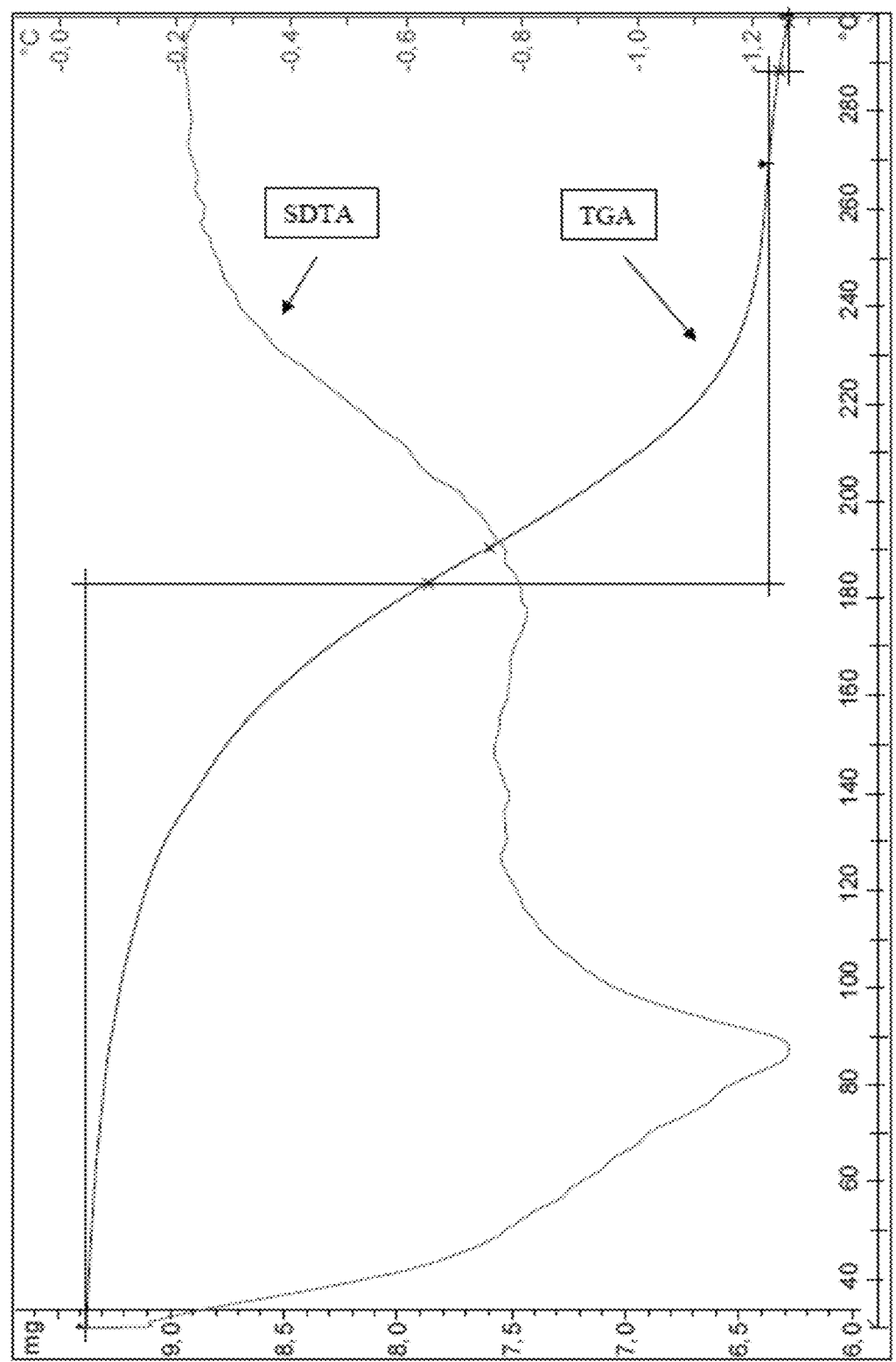
FIG. 9 shows the TGA of cocrystal of beta-sitosterol and benzyl alcohol of the present invention. The thermogram expresses loss weight (% w/w) versus temperature (° C.).

The thermogravimetric (TG) analysis of the cocrystal of beta-sitosterol and benzyl alcohol of the invention may also be further characterized by beta-sitosterol and benzyl alcohol a first weight loss of 31.9% from 30° C. to 260° C. and a second weight loss of 1.2% from 260° C. to 300° C. (cf. FIG. 9).

Figure 10:
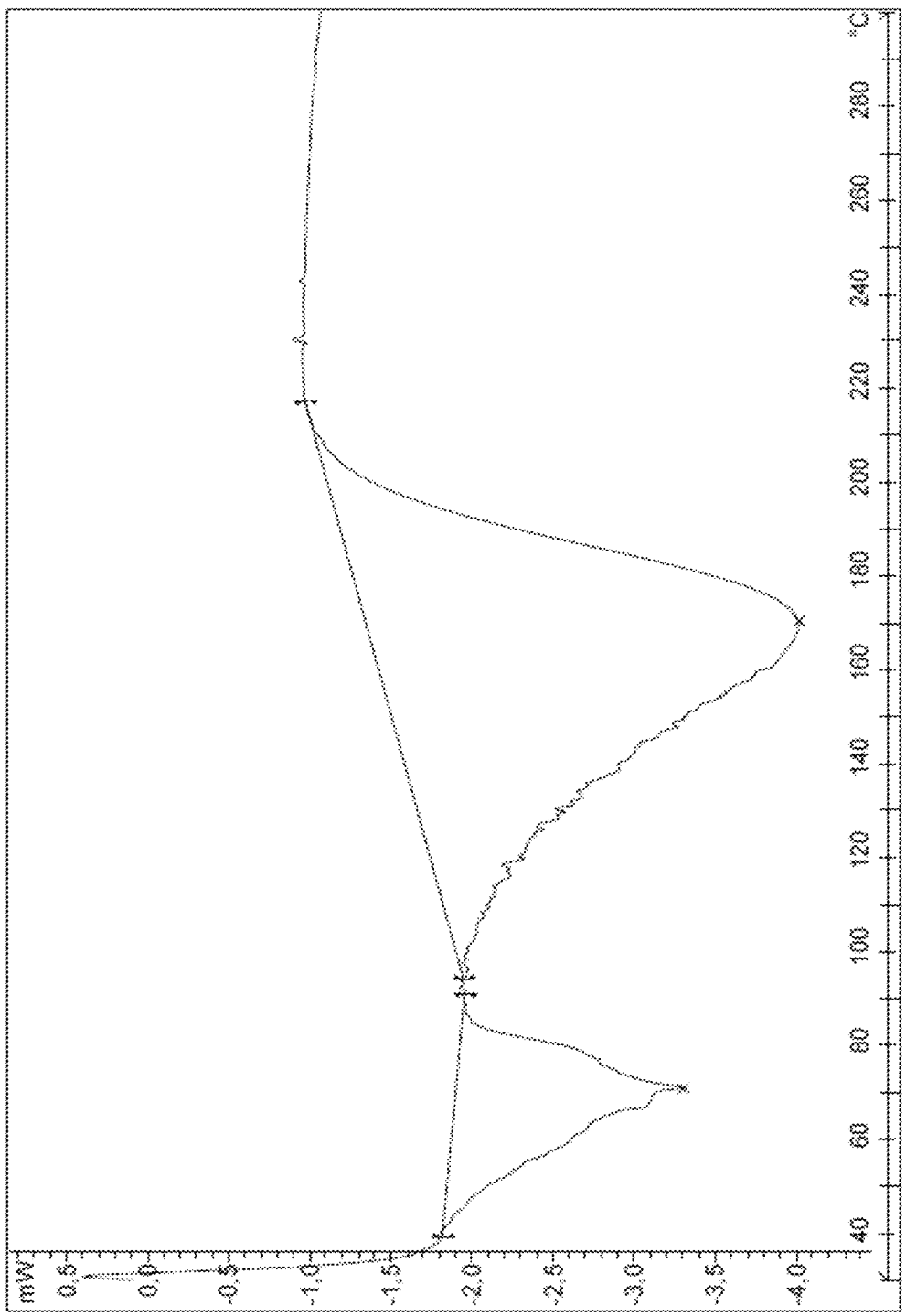
FIG. 10 shows the DSC of cocrystal of beta-sitosterol and benzyl alcohol of the present invention. The DSC thermal curve expresses the heat flow (m/W) versus temperature (° C.).

The cocrystal of beta-sitosterol and benzyl alcohol of the invention may also be further characterized by a first wide endothermic phenomenon at 45° C. with an associated heat of 42.9 J/g and a second wide endothermic phenomenon at 125° C. and an associated heat of 206.2 J/by DSC (Differential scanning calorimetry) analysis (cf. FIG. 10).

In an embodiment, the cocrystal of beta-sitosterol and benzyl alcohol of the formula below is in a molar ratio 4:1.

In an embodiment, the cocrystal beta-sitosterol and benzyl alcohol is a hydrate cocrystal; preferably the cocrystal of beta-sitosterol and benzyl alcohol is a monohydrate cocrystal having a molar ratio of beta-sitosterol:benzyl alcohol of 4:1.

The data of the structure of the cocrystal beta-sitosterol:benzyl alcohol defined above obtained by single crystal X-ray diffraction correspond to a monohydrate cocrystal and are shown below:

| Structure | cocrystal beta-sitosterol:benzyl alcohol Form III |
| --- | --- |
| Temperature (K) | 293(2) |
| Wavelength (Å) | 0.71073 |
| Crystal system | Triclinic |
| space group | P1 |
| a, b, c (Å) | 7.597(3), 9.730(4), 37.763(14) |
| α, β, γ (°) | 84.846(9), 86.089(8), 88.219(9) |
| Volume (Å$^3$) | 2772.76 |
| Z | 4 |

The second aspect of the invention relates to a hydrate crystal form of beta-sitosterol or a pharmaceutically acceptable ester thereof or an edible acceptable ester thereof having 1.25 molecules of water per molecule of beta-sitosterol. In an embodiment, the beta-sitosterol of the hydrate crystal of beta-sitosterol of the present invention is in form of a pharmaceutically acceptable ester thereof or an edible acceptable ester thereof.

When values of water of molecules are given it is said that these are "approximate" values due to the measurement error. It should be understood that when a water content of 1.25 is mentioned, it corresponds to a water content comprised from 1 to 1.50.

In an embodiment, the hydrate crystal form of beta-sitosterol of the present invention is characterized by having an X-ray powder diffractogram that comprises characteristic peaks at approximately 3.2 and 4.7±0.3 degrees 2 theta (Cu—K$_\alpha$ radiation, $\lambda$=1.5406 Å). In an embodiment, hydrate crystal form of beta-sitosterol of the invention is characterized by having an X-ray powder diffractogram that comprises further characteristic peaks at 9.0, 12.1 and 14.8±0.3 degrees 2 theta (Cu—K$_\alpha$ radiation, $\lambda$=1.5406 Å).

More specifically, the hydrate crystal form of beta-sitosterol of the invention is characterized by exhibiting in the X-ray powder diffractogram a pattern of peaks, expressed in 2 theta units in degrees, 2θ(°), which is shown in Table 5.

TABLE 5

List of selected peaks (only peaks with
relative intensity greater than or equal
to 1% are indicated):

| Pos. [°2Th.] | d-spacing [Å] | Rel. Int. [%] |
|---|---|---|
| 3.1537 | 28.01614 | 25.54 |
| 3.3442 | 26.4204 | 14.1 |
| 4.5013 | 19.63125 | 3.98 |
| 4.6936 | 18.82722 | 11.69 |
| 6.3251 | 13.97413 | 2.62 |
| 6.6965 | 13.19985 | 3.37 |
| 7.294 | 12.11982 | 2.45 |
| 9.0306 | 9.7928 | 5.24 |
| 12.1263 | 7.29884 | 28.44 |
| 12.5974 | 7.02696 | 4.15 |
| 13.489 | 6.56441 | 4.39 |
| 13.7934 | 6.4202 | 12.86 |
| 14.7962 | 5.98727 | 100 |
| 15.3694 | 5.76525 | 15.14 |
| 16.3535 | 5.42046 | 3.71 |
| 16.5482 | 5.35713 | 6.98 |
| 17.5034 | 5.06685 | 3.42 |
| 18.116 | 4.89689 | 27.22 |
| 20.6453 | 4.30232 | 5.41 |
| 23.5419 | 3.77911 | 6.78 |
| 23.7559 | 3.74555 | 3.22 |
| 25.6137 | 3.47794 | 1.77 |
| 27.282 | 3.26893 | 1.61 |

Figure 11:
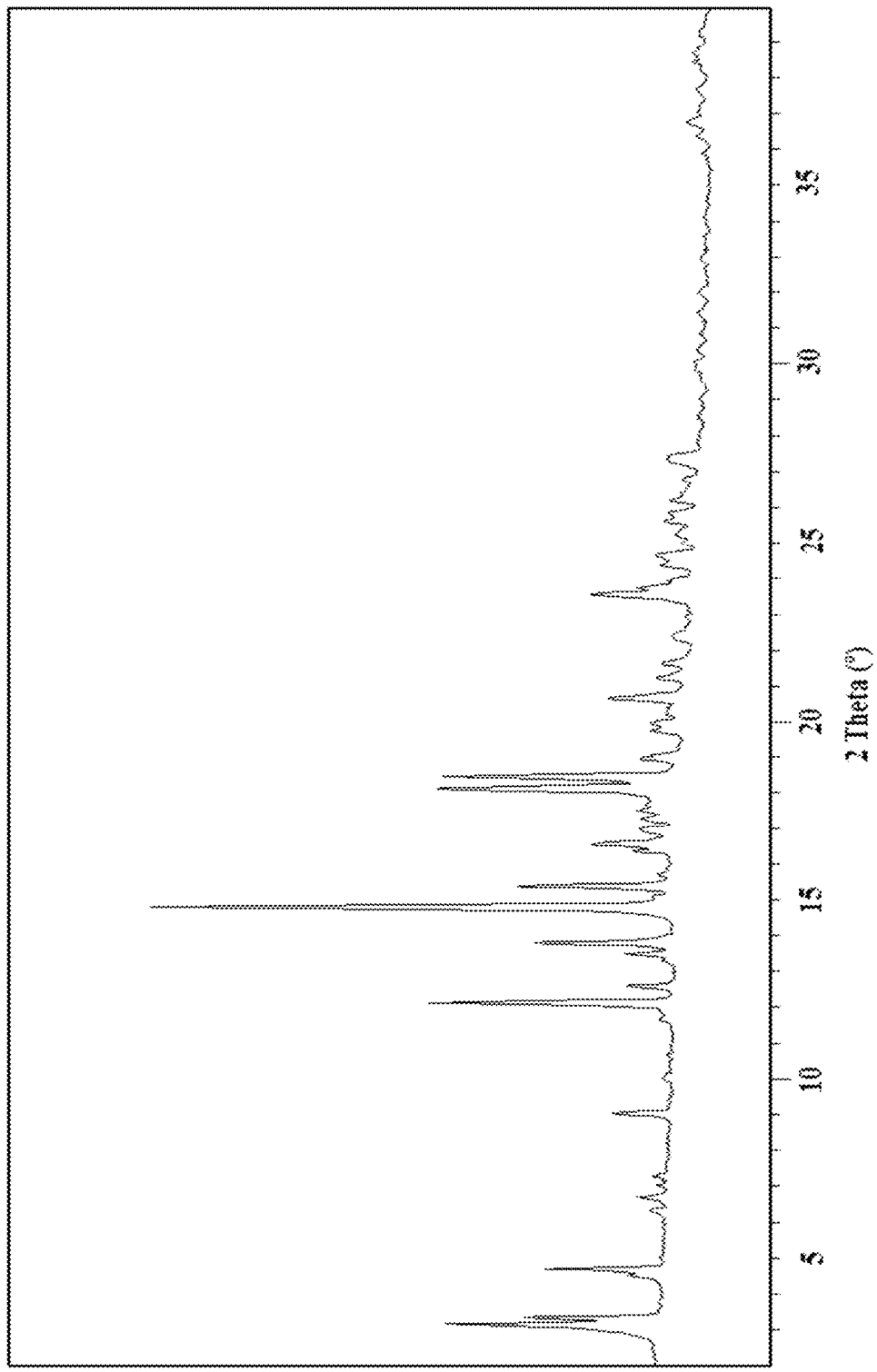
FIG. 11 shows the X-ray powder diffractogram (XRPD) of the hydrate crystal form of beta-sitosterol of the present invention. The spectrum expresses intensity (I; counts) versus degrees 2 theta (°).

The hydrate crystal form of beta-sitosterol of the invention may be further characterized by an X-ray diffractogram as in FIG. 11.

Figure 12:
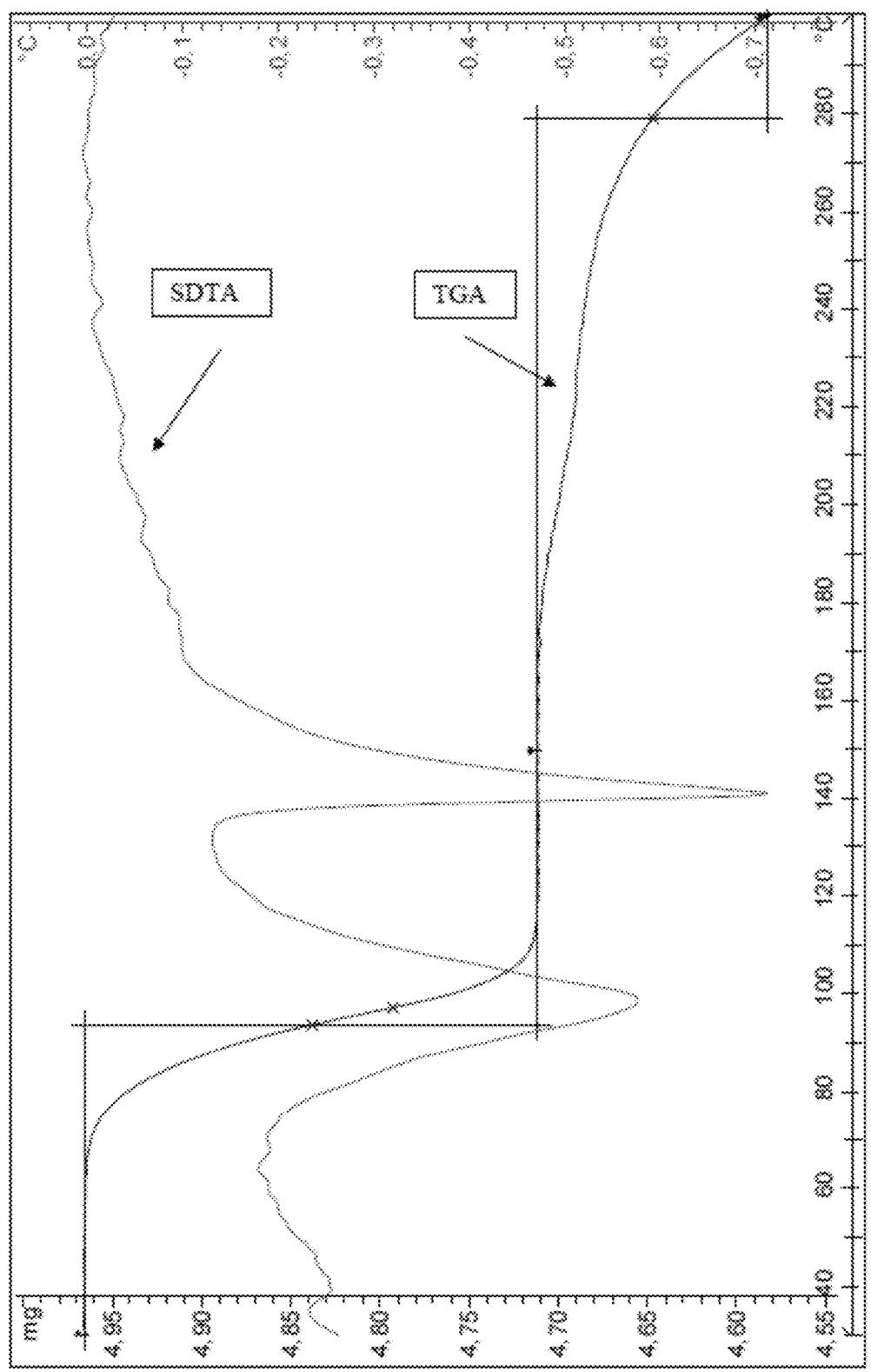
FIG. 12 shows the TGA of hydrate crystal form of beta-sitosterol of the present invention. The thermogram expresses loss weight (% w/w) versus temperature (° C.).

The thermogravimetric (TG) analysis of the hydrate crystal form of beta-sitosterol of the invention may also be further characterized by first weight loss of 5.1% from 33° C. to 154° C. which is attributed to 1.25 molecules of $H_2O$ per molecule of beta-sitosterol (theoretical weight loss of 5.8%) and a second weight loss of 2.6% from 154° C. to 300° C. (cf. FIG. 12).

Figure 13:
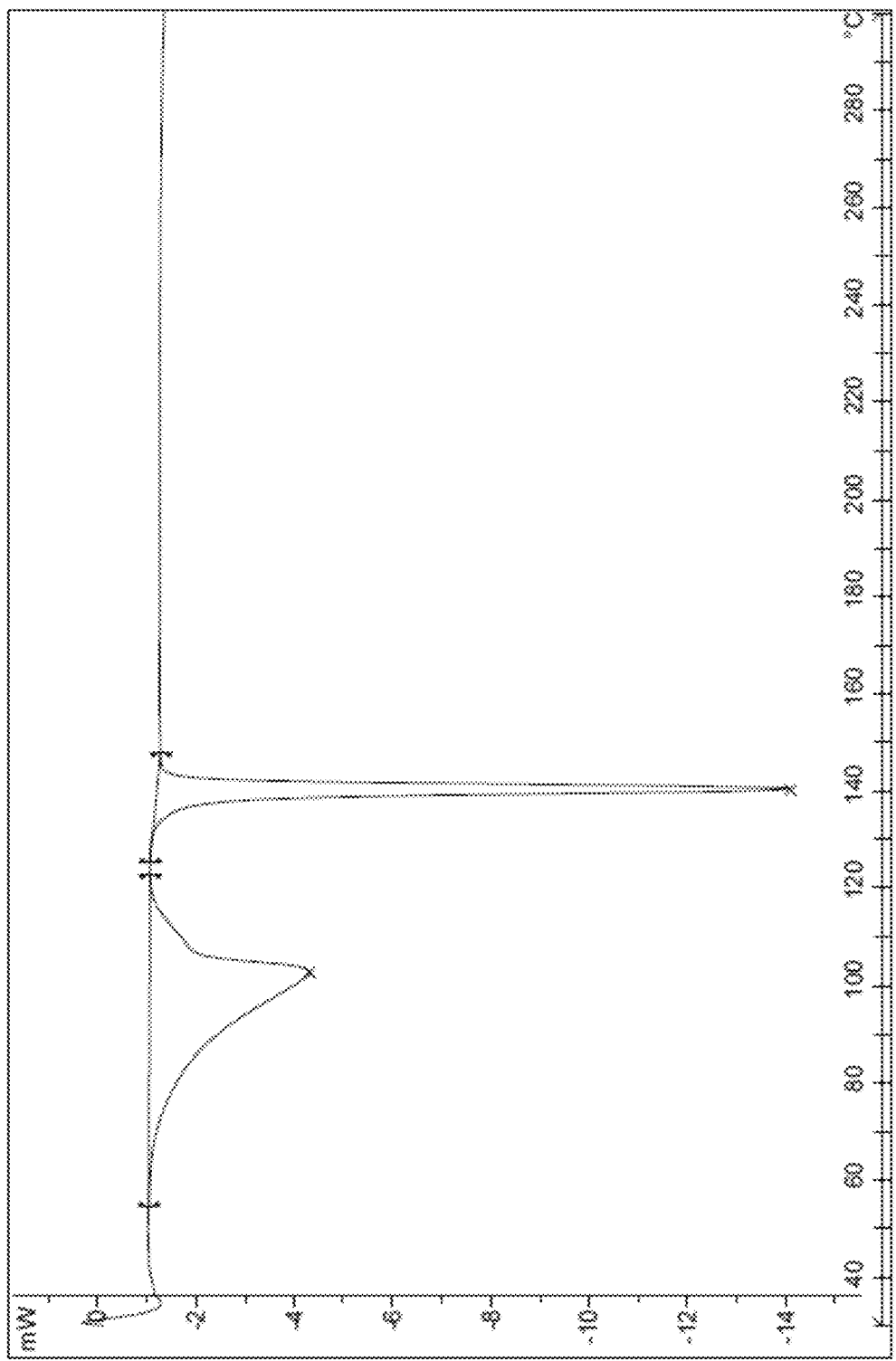
FIG. 13 shows the DSC of hydrate crystal form of beta-sitosterol of the present invention. The DSC thermal curve expresses the heat flow (m/W) versus temperature (° C.).

The hydrate crystal form of beta-sitosterol of the invention may also be further characterized by a first wide endothermic phenomenon at 77° C. with an associated heat of 94.8 J/g and a second endothermic phenomenon at 135° C. with an associated heat of 58.6 J/g by DSC (Differential scanning calorimetry) analysis (cf. FIG. 13).

It is also part of the invention the provision of processes for the preparation of the crystal forms of beta-sitosterol or a pharmaceutically acceptable ester thereof or an edible acceptable ester thereof of the first and the second aspect of the invention. The crystal forms of beta-sitosterol of the invention may be prepared as a pure form or as a mixture, including different phytosterols and phytostanols.

The processes for the preparation of the crystal forms of the present invention involve contacting the beta-sitosterol or alternatively a mixture of phytosterols/phytostanols with the corresponding coformer. The beta-sitosterol used as a starting material in the present invention is commercially available. Typically, the beta-sitosterol is available as a mixture of crystal forms. This mixture can be formed by anhydrous beta-sitosterol and hydrate beta-sitosterol, which can be in different proportions such as for example from 40:60 to 60:40. Particularly, the mixture of anhydrous and hydrate form of beta-sitosterol can be 50:50.

In an embodiment, the process for the preparation of the cocrystal of beta-sitosterol and L-lactic acid (cocrystal Form 1) of the present invention comprises: (a) slurring the beta-sitosterol in a mixture of L-lactic acid in a miscible organic solvent; and (b) isolating the cocrystal thus obtained.

In an embodiment, step (a) is carried out in the presence of a miscible organic solvent; preferably a water-miscible organic solvent selected from the group consisting of ($C_1$-$C_6$) alcohol, ($C_1$-$C_4$) alkyl-CO—($C_1$-$C_4$) alkyl, ($C_1$-$C_4$) alkyl-CO—O—($C_1$-$C_4$) alkyl and mixtures thereof. The term "alcohol" refers to an "alkane" wherein at least one hydrogen atom is substituted by a hydroxyl group and which contains the number of carbon atoms specified in the description or claims. The term "alkane" refers to a saturated, branched or linear hydrocarbon which contains the number of carbon atoms specified in the description or claims. Examples include methanol, ethanol, n-propanol, iso-propanol, butanol, iso-butanol, and sec-butanol. The term "alkyl" is as defined above. In an embodiment, step (a) is performed in the presence of ethyl acetate.

In an embodiment, the isolation step (b) may include removing the solvent such as water, for example, by one or more of the following operations: filtration, filtration under vacuum, decantation, and centrifugation, or other suitable techniques as known to a person skilled in the art. Preferably, step (b) is carried out by filtration of the solid followed by a washing step; preferably with water. In an embodiment, step (b) further comprises drying the isolated cocrystal; preferably the cocrystal is dried at room temperature, preferably under vacuum conditions. Generally, the vacuum involves a pressure comprised from 0.5 mbar to 3 mbar.

The cocrystal of beta-sitosterol and L-lactic acid of the invention may also be defined by its preparation process. Accordingly, this aspect of the invention can be formulated as the cocrystal of beta-sitosterol and L-lactic acid (cocrystal Form 1) as defined above, obtainable by any of the previous processes, optionally including any preferred or particular embodiment of the processes and possible combinations of some of the process features disclosed above.

In an embodiment, the process for the preparation of the cocrystal of beta-sitosterol and propionic acid of the present invention (cocrystal Form 2) comprises: (a') mixing the beta-sitosterol and propionic acid in a molar ratio from 1:10 to 1:50; and (b') isolating the cocrystal thus obtained.

In an embodiment, the process for the preparation of the cocrystal of beta-sitosterol and propionic acid of the present invention (cocrystal Form 2) further comprises an additional step (c) which comprises adding an anti-solvent to the mixture obtained in step (a'). As used herein, the term "anti-solvent" refers to a solvent in which the crystal has limited or no solubility, and which can promote crystallization. In an embodiment, the anti-solvent is selected from the group consisting of water, pentane, heptane, ethylene glycol, methanol, acetonitrile and ethanol.

In an embodiment, step (a') of the process for the preparation of the cocrystal of beta-sitosterol and propionic acid of the present invention (cocrystal Form 2) comprises mixing the beta-sitosterol and propionic acid in a molar ratio from 1:2 to 1:100; preferably from 1:10 to 1:50.

In an embodiment, step (b') for the preparation of the cocrystal of beta-sitosterol and propionic acid of the present invention (cocrystal Form 2) comprises: (d) firstly, drying the crystal thus obtained under a vacuum from 80 to 500 mmHg, preferably from 100 to 300 mmHg; and (e) secondly, passing an air flow through the crystal obtained in step (d).

All the embodiments disclosed above for step (a) also applies to step (a'). In an embodiment, step (a') is carried out at room temperature. In another embodiment, step (a') is carried out in neat conditions, which means in the absence of organic solvents. All the embodiments disclosed above for step (b) also applies to step (b').

The cocrystal of beta-sitosterol and propionic acid of the invention, particularly the cocrystal beta-sitosterol:propionic acid may also be defined by its preparation process. Accordingly, this aspect of the invention can be formulated as the cocrystal of beta-sitosterol and propionic acid (cocrystal Form 2) as defined above, obtainable by any of the previous processes, optionally including any preferred or particular embodiment of the processes and possible combinations of some of the process features disclosed above.

In an embodiment, the process for the preparation of the cocrystal of beta-sitosterol and zymonic acid of the present invention (cocrystal Form 3) comprises: (a") mixing the beta-sitosterol with pyruvic acid in a miscible organic solvent; and (b") isolating the cocrystal thus obtained.

All the embodiments disclosed above for step (a) also applies to step (a"). In an embodiment, step (a") is carried out at room temperature. In an embodiment, step (a") is carried out in the presence of acetone. All the embodiments disclosed above for step (b) also applies to step (b").

The cocrystal of beta-sitosterol and zymonic acid of the invention, particularly the cocrystal beta-sitosterol:zymonic acid may also be defined by its preparation process. Accordingly, this aspect of the invention can be formulated as the cocrystal of beta-sitosterol and zymonic acid (cocrystal Form 3) as defined above, obtainable by any of the previous processes, optionally including any preferred or particular embodiment of the processes and possible combinations of some of the process features disclosed above.

In an embodiment, the process for the preparation of the cocrystal of beta-sitosterol and benzyl alcohol of the present invention (cocrystal Form 4) comprises: (a''') mixing the beta-sitosterol with benzyl alcohol at a temperature comprised from 50° C. to 75° C. followed by cooling down the temperature until 4° C. to 8° C.; and (b''') isolating the cocrystal thus obtained.

All the embodiments disclosed above for step (b) also applies to step (b'''). Preferably, step (b''') is carried out by: (i) decanting the gel obtained in step (a'''); (ii) dissolving the gel obtained in step (i) in an organic water-immiscible solvent and evaporating the solvent until dryness; (iii) mixing the dry solid obtained in step (ii) in an organic water-immiscible solvent and evaporation of the solvent until dryness; and (iv) filtrating the solid obtained in step (iii) and drying the isolated cocrystal; preferably the cocrystal is dried at room temperature, preferably under vacuum conditions. Generally, the vacuum involves a pressure comprised from 0.5 mbar to 3 mbar.

In an embodiment, step (ii) of step (b''') is carried out in the presence of a water-immiscible organic solvent selected from the group consisting of ($C_1$-$C_6$)alkane, ($C_1$-$C_4$)alkyl-O—($C_1$-$C_4$)alkyl (dialkylethers) and mixtures thereof. The terms "alkane" and "alkyl" are as defined above. In an embodiment, step (ii) of (b') is carried out in the presence of pentane; and step (iii) of (b''') is carried out in the presence of diethyl ether.

The cocrystal of beta-sitosterol and benzyl alcohol of the invention may also be defined by its preparation process. Accordingly, this aspect of the invention can be formulated as the cocrystal of beta-sitosterol and benzyl alcohol as defined above (cocrystal Form 4), obtainable by any of the previous processes, optionally including any preferred or particular embodiment of the processes and possible combinations of some of the process features disclosed above.

In an embodiment, the process for the preparation of the cocrystal of beta-sitosterol and gallic acid of the present invention (cocrystal Form 5) comprises: (a$^v$) mixing the beta-sitosterol with gallic acid in a miscible organic solvent; and (b') isolating the cocrystal thus obtained.

All the embodiments disclosed above for step (a) also applies to step (a$^v$). In an embodiment, step (a$^v$) is carried out at room temperature. In an embodiment, step (a$^v$) is carried out in the presence of ethyl acetate.

All the embodiments disclosed above for step (b) also applies to step (by).

The cocrystal of beta-sitosterol and gallic acid of the invention may also be defined by its preparation process. Accordingly, this aspect of the invention can be formulated as the cocrystal of beta-sitosterol and gallic acid (cocrystal Form 5) as defined above, obtainable by any of the previous processes, optionally including any preferred or particular embodiment of the processes and possible combinations of some of the process features disclosed above.

In an embodiment, the process for the preparation of the cocrystal of beta-sitosterol and 2,4-dihydroxybenzoic acid of the present invention (cocrystal Form 6) comprises: (a$^{vi}$) mixing the beta-sitosterol with 2,4-dihydroxybenzoic acid in a miscible organic solvent; and (b$^{vi}$) isolating the cocrystal thus obtained.

All the embodiments disclosed above for step (a) also applies to step (a$^{vi}$). In an embodiment, step (a$^{vi}$) is carried out at room temperature. In an embodiment, step (a$^{vi}$) is carried out in the presence of ethyl acetate. All the embodiments disclosed above for step (b) also applies to step (b$^{vi}$).

The cocrystal of beta-sitosterol and 2,4-dihydroxybenzoic acid of the invention may also be defined by its preparation process. Accordingly, this aspect of the invention can be formulated as the cocrystal of beta-sitosterol and 2,4-dihydroxybenzoic acid (cocrystal Form 6) as defined above, obtainable by any of the previous processes, optionally including any preferred or particular embodiment of the processes and possible combinations of some of the process features disclosed above.

In an embodiment, the process for the preparation of the cocrystal of beta-sitosterol and 3,4-dihydroxybenzoic acid of the present invention (cocrystal Form 7) comprises: (a$^{vii}$) mixing the beta-sitosterol with 3,4-dihydroxybenzoic acid in a miscible organic solvent; and (b$^{vii}$) isolating the cocrystal thus obtained.

All the embodiments disclosed above for step (a) also applies to step (a$^{vii}$). In an embodiment, step (a$^{vii}$) is carried out at room temperature. In an embodiment, step (a$^{vii}$) is carried out in the presence of ethyl acetate. All the embodiments disclosed above for step (b) also applies to step (b$^{vii}$).

The cocrystal of beta-sitosterol and 3,4-dihydroxybenzoic acid of the invention may also be defined by its preparation process. Accordingly, this aspect of the invention can be formulated as the cocrystal of beta-sitosterol and 3,4-dihydroxybenzoic acid (cocrystal Form 7) as defined above, obtainable by any of the previous processes, optionally including any preferred or particular embodiment of the processes and possible combinations of some of the process features disclosed above.

In an embodiment, the process for the preparation of the Form A of the cocrystal of beta-sitosterol and 3,5-dihydroxybenzoic acid of the present invention (cocrystal Form 8) comprises: (a$^{viii}$) mixing the beta-sitosterol with 3,5-dihydroxybenzoic acid in a miscible organic solvent; and (b$^{viii}$) isolating the cocrystal thus obtained.

All the embodiments disclosed above for step (a) also applies to step (a$^{viii}$). In an embodiment, step (a$^{viii}$) is carried out at room temperature. In an embodiment, step (a$^{viii}$) is carried out in the presence of ethyl acetate. All the embodiments disclosed above for step (b) also applies to step (b$^{viii}$).

The Form A of the cocrystal of beta-sitosterol and 3,5-dihydroxybenzoic acid of the invention may also be defined by its preparation process. Accordingly, this aspect of the invention can be formulated as the Form A of the cocrystal of beta-sitosterol and 3,5-dihydroxybenzoic acid (cocrystal Form 8) as defined above, obtainable by any of the previous processes, optionally including any preferred or particular embodiment of the processes and possible combinations of some of the process features disclosed above.

In an embodiment, the process for the preparation of the Form B of the cocrystal of beta-sitosterol and 3,5-dihydroxybenzoic acid of the present invention (cocrystal Form 9) comprises: ($a^{viiii}$) mixing the beta-sitosterol with 3,5-dihydroxybenzoic acid in a miscible organic solvent; and ($b^{viiii}$) isolating the cocrystal thus obtained.

All the embodiments disclosed above for step (a) also applies to step ($a^{viiii}$). In an embodiment, step ($a^{viiii}$) is carried out at room temperature. In an embodiment, step ($a^{viiii}$) is carried out in the presence of ethyl acetate. All the embodiments disclosed above for step (b) also applies to step ($b^{viiii}$).

The Form B of the cocrystal of beta-sitosterol and 3,5-dihydroxybenzoic acid of the invention may also be defined by its preparation process. Accordingly, this aspect of the invention can be formulated as the form B of the cocrystal of beta-sitosterol and 3,5-dihydroxybenzoic acid (cocrystal Form 9) as defined above, obtainable by any of the previous processes, optionally including any preferred or particular embodiment of the processes and possible combinations of some of the process features disclosed above.

In an embodiment, the process for the preparation of the cocrystal of beta-sitosterol and 3-hydroxybenzoic acid of the present invention (cocrystal Form 10) comprises: ($a^{vv}$) mixing the beta-sitosterol with 3-hydroxybenzoic acid in a miscible organic solvent; and ($b^{vv}$) isolating the cocrystal thus obtained.

All the embodiments disclosed above for step (a) also applies to step ($a^{vv}$). In an embodiment, step ($a^{vv}$) is carried out at room temperature. In an embodiment, step ($a^{vv}$) is carried out in the presence of ethyl acetate. All the embodiments disclosed above for step (b) also applies to step ($b^{vv}$).

The cocrystal of beta-sitosterol and 3-hydroxybenzoic acid of the invention may also be defined by its preparation process. Accordingly, this aspect of the invention can be formulated as the cocrystal of beta-sitosterol and 3-hydroxybenzoic acid (cocrystal Form 10) as defined above, obtainable by any of the previous processes, optionally including any preferred or particular embodiment of the processes and possible combinations of some of the process features disclosed above.

In an embodiment, the process for the preparation of the Form A of the cocrystal of beta-sitosterol and 4-hydroxybenzoic acid of the present invention (cocrystal Form 11) comprises: ($a^{vvi}$) mixing the beta-sitosterol with 4-hydroxybenzoic acid in a miscible organic solvent; and ($b^{vvi}$) isolating the cocrystal thus obtained.

All the embodiments disclosed above for step (a) also applies to step ($a^{vvi}$). In an embodiment, step ($a^{vvi}$) is carried out at room temperature. In an embodiment, step ($a^{vvi}$) is carried out in the presence of ethyl acetate. All the embodiments disclosed above for step (b) also applies to step ($b^{vvi}$).

The Form A of the cocrystal of beta-sitosterol and 4-hydroxybenzoic acid of the invention may also be defined by its preparation process. Accordingly, this aspect of the invention can be formulated as the Form A of the cocrystal of beta-sitosterol and 4-hydroxybenzoic acid (cocrystal Form 11) as defined above, obtainable by any of the previous processes, optionally including any preferred or particular embodiment of the processes and possible combinations of some of the process features disclosed above.

In an embodiment, the process for the preparation of the Form B of the cocrystal of beta-sitosterol and 4-hydroxybenzoic acid of the present invention (cocrystal Form 12) comprises: ($a^{vvii}$) mixing the beta-sitosterol with 4-hydroxybenzoic acid in a miscible organic solvent; and ($b^{vvii}$) isolating the cocrystal thus obtained.

All the embodiments disclosed above for step (a) also applies to step ($a^{vvii}$). In an embodiment, step ($a^{vvii}$) is carried out at room temperature. In an embodiment, step ($a^{vvii}$) is carried out in the presence of ethyl acetate. All the embodiments disclosed above for step (b) also applies to step ($b^{vviii}$).

The Form B of the cocrystal of beta-sitosterol and 4-hydroxybenzoic acid of the invention may also be defined by its preparation process. Accordingly, this aspect of the invention can be formulated as the form B of the cocrystal of beta-sitosterol and 4-hydroxybenzoic acid (cocrystal Form 12) as defined above, obtainable by any of the previous processes, optionally including any preferred or particular embodiment of the processes and possible combinations of some of the process features disclosed above.

In an embodiment, the process for the preparation of the hydrate crystal form of beta-sitosterol characterized by having an X-ray powder diffractogram that comprises characteristic peaks at approximately 3.2 and 4.7±0.3 degrees 2 theta (Cu-Kα radiation, λ=1.5406 Å), comprises: ($a''''$) mixing the beta-sitosterol with an organic solvent in the presence of propionic acid; and ($b''''$) isolating the cocrystal thus obtained.

In an embodiment, the water-miscible organic solvent of step ($a''''$) is selected from the group consisting of ($C_1$-$C_4$) alkyl-CO—($C_1$-$C_4$) alkyl, ($C_1$-$C_4$) alkyl-CO—O—($C_1$-$C_4$) alkyl, water, cyclo($C_5$-$C_6$)alkane, phenyl-($C_1$-$C_4$)alkyl, halogen-($C_1$-$C_4$)alkane, and mixtures thereof. In an embodiment, the water-miscible organic solvent of step ($a''''$) is selected from the group consisting of acetone, ethyl acetate, water, cyclohexane, chloroform, tetrahydrofurane, toluene, dichloromethane and mixture thereof; preferably acetone and ethyl acetate. The term cycloalkane refers to a "cyclic" alkane which contains the number of carbon atoms specified in the description or claims. The term cycloalkane includes carbocyclic alkanes or heterocyclic alkanes. The term "carbocyclic" alkane refers to a cyclic alkane being each member of the cycle a carbon atom. Examples of carbocyclic alkanes include cyclopentane and cyclohexane. The term "heterocyclic" alkane refers to a "carbocyclic" compound in that at least one carbon atom is substituted by a N, NH, O, or S atom. Examples of heterocyclic alkane include tetrahydrofurane and tetrahydropirane. The term "halogen-alkane" refers to an alkane in that at least one hydrogen atom is substituted by an halogen atom and which contains the number of carbon atoms specified in the description or claims. Examples of halogen-alkane include chloroform, trichloroethane and dichloroethane.

In an embodiment, step ($a''''$) is carried out in the presence of an organic acid. In an embodiment, step ($a''''$) is carried out in the presence of an organic acid selected from the group consisting of propionic acid, acetic acid, formic acid and mixture thereof; preferably propionic acid.

All the embodiments disclosed above for step (a) also applies to step ($a''''$). In an embodiment, step ($a''''$) is carried out at room temperature. In an embodiment, step ($a''''$) is carried out in the presence of acetone. All the embodiments disclosed above for step (b) also applies to step ($b''''$).

The hydrate crystal form of beta-sitosterol of the present invention may also be defined by its preparation process. Accordingly, this aspect of the invention can be formulated as the hydrate crystal form of beta-sitosterol as defined above, obtainable by any of the previous processes, optionally including any preferred or particular embodiment of the processes and possible combinations of some of the process features disclosed above.

The processes for the preparation of the crystals of beta-sitosterol of the present invention are advantageous because allow obtaining the crystals in a high chemical yield and high polymorphic purity. Typically, the crystals obtained by the processes as mentioned above has a chemical purity equal to or higher than 90 area %; preferably, equal to or higher than 95 area %. Typically, the crystals obtained by the processes as mentioned above has such a polymorphic purity that no other crystalline forms of the beta-sitosterol is detectable by X-ray powder diffraction measurement when using a X-ray diffractometer with Cu-Kα radiation λ=1.5406 Å.

The third aspect of the invention relates to a combination comprising a cocrystal of beta-sitosterol or a pharmaceutically acceptable ester thereof or an edible acceptable ester thereof and an organic carboxylic acid as defined above; and a crystal of beta-sitosterol or a pharmaceutically acceptable ester thereof or an edible acceptable ester thereof selected from the group consisting of a cocrystal of beta-sitosterol and organic alcohol as defined above, and a hydrate crystal form of beta-sitosterol or a pharmaceutically acceptable ester thereof or an edible acceptable ester thereof having 1.25 molecules of water as defined above.

All the embodiments disclosed above for crystals of beta-sitosterol as defined above also apply for the combination of the present invention.

In an embodiment, the combination is one comprising: a cocrystal of beta-sitosterol and an organic carboxylic acid as defined above; and a crystal of beta-sitosterol and organic alcohol as defined above.

In an embodiment, the combination of the invention is one comprising a cocrystal of beta-sitosterol and an organic carboxylic acid selected from the group consisting of L-lactic acid, propionic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid. In an embodiment, the combination of the invention is one comprising a cocrystal of beta-sitosterol and an organic carboxylic acid selected from the group consisting of L-lactic acid, propionic acid, zymonic acid, succinic acid, ascorbic acid and gallic acid; preferably a cocrystal of beta-sitosterol and propionic acid. In an embodiment, the combination of the invention is one comprising a cocrystal of beta-sitosterol and an organic carboxylic acid selected from the group consisting of L-lactic acid, zymonic acid, succinic acid, ascorbic acid and gallic acid. In an embodiment, the combination of the invention is one comprising a crystal of beta-sitosterol and organic alcohol selected from the group consisting of benzyl alcohol, ethanol, and isopropanol; preferably benzyl alcohol.

In an embodiment, the combination of the invention is one comprising a cocrystal of beta-sitosterol and an organic carboxylic acid selected from the group consisting of L-lactic acid, propionic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid. In an embodiment, the combination of the invention is one comprising a cocrystal of beta-sitosterol and an organic carboxylic acid selected from the group consisting of L-lactic acid, propionic acid, zymonic acid, succinic acid, gallic acid and ascorbic acid; preferably a cocrystal of beta-sitosterol and propionic acid; and a crystal of beta-sitosterol and organic alcohol selected from the group consisting of benzyl alcohol, ethanol, and isopropanol; preferably benzyl alcohol. In a particular embodiment, the combination of the invention is one comprising propionic acid and benzyl alcohol.

In an embodiment, the combination of the invention is one comprising a cocrystal of beta-sitosterol and an organic carboxylic acid selected from the group consisting of L-lactic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid. In an embodiment, the combination of the invention is one comprising a cocrystal of beta-sitosterol and an organic carboxylic acid selected from the group consisting of L-lactic acid, zymonic acid, succinic acid, gallic acid and ascorbic acid; and a crystal of beta-sitosterol and organic alcohol selected from the group consisting of benzyl alcohol, ethanol, and isopropanol; preferably benzyl alcohol.

In an embodiment, the combination of the invention is one comprising a cocrystal of beta-sitosterol and an organic carboxylic acid selected from the group consisting of cocrystal Form 1, cocrystal Form 2, cocrystal Form 3, cocrystal Form 5, cocrystal Form 6, cocrystal Form 7, cocrystal Form 8, cocrystal Form 9, cocrystal Form 10, cocrystal Form 11 and cocrystal Form 12 as defined above; preferably a cocrystal Form 2 as defined above; and a crystal of beta-sitosterol and organic alcohol selected from the group consisting of benzyl alcohol, ethanol, and isopropanol; preferably cocrystal Form 4. In a particular embodiment, the combination of the invention is one comprising cocrystal Form 2 and cocrystal Form 4 as defined above.

In an embodiment, the combination of the invention is one comprising a cocrystal of beta-sitosterol and an organic carboxylic acid selected from the group consisting of cocrystal Form 1, cocrystal Form 3, cocrystal Form 5, cocrystal Form 6, cocrystal Form 7, cocrystal Form 8, cocrystal Form 9, cocrystal Form 10, cocrystal Form 11 and cocrystal Form 12 as defined above; and a crystal of beta-sitosterol and organic alcohol selected from the group consisting of benzyl alcohol, ethanol, and isopropanol; preferably cocrystal Form 4.

In an embodiment, the combination is one comprising: a cocrystal of beta-sitosterol and an organic carboxylic acid as defined above; and a hydrate crystal form of beta-sitosterol having 1.25 molecules of water as defined above.

In an embodiment, the combination of the invention is one comprising a cocrystal of beta-sitosterol and an organic carboxylic acid selected from the group consisting of L-lactic acid, propionic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid. In an embodiment, the combination of the invention is one comprising a cocrystal of beta-sitosterol and an organic carboxylic acid selected from the group consisting of L-lactic acid, propionic acid, zymonic acid, succinic acid, gallic acid and ascorbic acid; preferably a cocrystal of beta-sitosterol and propionic acid; and a hydrate crystal form of beta-sitosterol having 1.25 molecules of water per molecule of beta-sitosterol as defined above. In a particular embodiment, the combination of the invention is one comprising propionic acid and a hydrate crystal form of beta-sitosterol having 1.25 molecules of water per molecule of beta-sitosterol.

In an embodiment, the combination of the invention is one comprising a cocrystal of beta-sitosterol and an organic carboxylic acid selected from the group consisting of L-lactic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid. In an embodiment, the combination of the invention is one comprising a cocrystal of beta-sitosterol and an organic carboxylic acid selected from the group consisting of L-lactic acid, zymonic acid, succinic acid, gallic acid and ascorbic acid; and a hydrate crystal form of beta-sitosterol having 1.25 molecules of water per molecule of beta-sitosterol as defined above.

In an embodiment, the combination of the invention is one comprising a cocrystal of beta-sitosterol and an organic carboxylic acid selected from the group consisting of cocrystal Form 1, cocrystal Form 2, cocrystal Form 3, cocrystal Form 5, cocrystal Form 6, cocrystal Form 7, cocrystal Form 8, cocrystal Form 9, cocrystal Form 10, cocrystal Form 11 and cocrystal Form 12; preferably a cocrystal Form 2; and a hydrate crystal form of beta-sitosterol having 1.25 molecules of water per molecule of beta-sitosterol as defined above. In a particular embodiment, the combination of the invention is one comprising cocrystal Form 2 and a hydrate crystal form of beta-sitosterol having 1.25 molecules of water per molecule of beta-sitosterol.

In an embodiment, the combination of the invention is one comprising a cocrystal of beta-sitosterol and an organic carboxylic acid selected from the group consisting of cocrystal Form 1, cocrystal Form 3, cocrystal Form 5, cocrystal Form 6, cocrystal Form 7, cocrystal Form 8, cocrystal Form 9, cocrystal Form 10, cocrystal Form 11 and cocrystal Form 12; and a hydrate crystal form of beta-sitosterol having 1.25 molecules of water per molecule of beta-sitosterol as defined above.

As it is mentioned above, the fourth aspect of the invention relates to a composition comprising an effective amount of a cocrystal of beta-sitosterol and an organic carboxylic acid as defined above; a hydrate crystal form of beta-sitosterol as defined above; or alternatively a combination as defined above together with one or more appropriate acceptable excipients or carriers.

The term "effective amount" refers to the amount of the crystal of beta-sitosterol or alternatively of the combination of crystals of beta-sitosterol of the present invention which provides a therapeutic effect after its application.

In an embodiment, the composition of the fourth aspect of the invention is a pharmaceutical composition comprising a pharmaceutically effective amount of a cocrystal of beta-sitosterol as defined above, a hydrate crystal form of beta-sitosterol as defined above, or a combination of crystals of beta-sitosterol as defined above together with one or more appropriate pharmaceutically acceptable excipients or carriers. The term "pharmaceutical composition" refers to a mixture of the cocrystal as defined above, the hydrate crystal form as defined above or the combination as defined above with other chemical components, such as diluents or carriers. The pharmaceutical composition facilitates administration of the cocrystal to an organism.

In an embodiment, the composition of the fourth aspect of the invention is an edible composition comprising an effective amount of a cocrystal of beta-sitosterol as defined above, a hydrate crystal form as defined above or a combination as defined above together with one or more appropriate edible acceptable excipients or carriers.

The edible composition includes dietary supplement or functional food. In an embodiment, the edible composition is a dietary supplement. The term "dietary supplement", "food supplement" or "nutritional supplement" as used herein interchangeably refers to a preparation intended to supplement the diet and provide nutrients, such as vitamins, minerals, fibre, fatty acids, or amino acids, that may be missing or may not be consumed in sufficient quantity in a person's diet, as well as bioactive compounds with health beneficial effects. Dietary supplements can be in form of tablets, capsules, softgels, gelcaps, liquids, powders, bars, drinks, shakes and other food products. The terms "acceptable excipients or carriers" refers to acceptable material, composition or vehicle, which include without limitation fillers, diluents, binders, lubricants and disintegrants. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio.

In an embodiment, the edible composition is a functional food. The term "functional food" as used herein refers to any healthy or functional food which helps to maintain the body functions beyond the basic role of supplying nutrients. They can be used as a food additive to produce a functional food. Thus, they can be added to semisolid products, solid products, or liquid products, or their derivatives such as concentrates or powders. When the food additive is added to a liquid product the resulting product is known as functional beverage. The term "functional beverage" refers to drinks that have been enhanced with added ingredients which help to maintain the body functions beyond basic nutrition. Examples of food products are selected from the list consisting of milk and derivatives such as yoghurts or cheese; beverages including juices, soft drinks, sport drinks, or other beverages such as distilled and fermented beverages; salad dressing; yellow fat spread; mayonnaise; confectionary such as chocolates, candies, or jellies; pasta; cereals; and bakery.

The compositions of the present invention can be prepared according to methods well known in the state of the art. The appropriate excipients and/or carriers, and their amounts, can readily be determined by those skilled in the art according to the type of formulation being prepared.

All the embodiments disclosed above for the cocrystals of beta-sitosterol as defined above, the hydrate crystal form of beta-sitosterol as defined above, as well as the combination as defined above also applies for the compositions of the invention.

The fifth aspect of the invention relates to a cocrystal of beta-sitosterol as defined above, a hydrate crystal form as defined above, or a combination as defined above for use as a medicament. Furthermore, a composition as defined above for use as a medicament is also part of the invention.

As mentioned above, the sixth aspect of the invention relates to a cocrystal of beta-sitosterol as defined above, a hydrate crystal form as defined above or a combination as defined above for use in the prophylaxis and/or treatment of a disease or condition which involves an alteration of lipid metabolism, circulating levels of lipids in the blood and/or lipid composition in tissues and organs. This aspect could be also formulated as the use of a cocrystal of beta-sitosterol as defined above, a hydrate crystal form as defined above or a combination as defined above for the preparation of a medicament or a dietary ingredient or supplement for the prophylaxis and/or treatment of a disease or condition which involves an alteration of lipid metabolism, circulating levels of lipids in the blood and/or lipid composition in tissues and organs. It also relates to a method for the prophylaxis and/or treatment of a mammal suffering, or susceptible to suffer, from a disease or condition which involves an alteration of lipid metabolism, circulating levels of lipids in the blood and/or lipid composition in tissues and organs, wherein the method comprises administering to said mammal an effective amount of a cocrystal of beta-sitosterol as defined above, a hydrate crystal form as defined above or a combination as defined above, together with one or more acceptable excipients or carriers.

In an embodiment, the disease or condition which involves an alteration of lipid metabolism, circulating levels of lipids in the blood and/or lipid composition in tissues and organs is a pathologic, phisiologic or functional alteration selected from the group consisting of hypercholesterolemia, hypertriglyceridemia, sitosterolemia and mixed dyslipidaemia, cardiovascular diseases and diabetes. In an embodiment, the disease or condition which involves an alteration of lipid metabolism, circulating levels of lipids in the blood and/or lipid composition in tissues and organs is selected form the group consisting of hypercholesterolemia, hypertriglyceridemia, sitosterolemia and mixed dyslipidaemia.

Furthermore, a composition as defined above for use in the prophylaxis and/or treatment of a disease or condition which involves an alteration of lipid metabolism, circulating levels of lipids in the blood and/or lipid composition in tissues and organs is also part of the invention.

The term "hypercholesterolemia" refers to those diseases or conditions that involves an excess of cholesterol in the blood, a phenomenon that occurs when total cholesterol levels are higher than the standard levels, and in particular when associated to higher LDL-cholesterol. The term "hypertriglyceridemia" refers to those diseases or conditions that involve an excess of triglycerides in the blood. The term "mixed dyslipidaemia" refers to those diseases or conditions that involve an excess of cholesterol and triglyceride levels in blood.

The term "sitosterolemia" refers to those diseases or conditions that involve higher intestinal absorption and lower biliary excretion of dietary sterols (including plant sterols and cholesterol); this inherited metabolic disorder is associated with hypercholesterolemia.

In an embodiment, wherein the disease or condition is a hypercholesterolemia, then the prophylaxis and/or treatment comprises administering the cocrystal of beta-sitosterol and an organic alcohol as defined above; preferably selected from benzyl alcohol, ethanol, and isopropanol; more preferably benzyl alcohol; more much preferably the cocrystal of Form 4; or alternatively the hydrate crystal form of beta-sitosterol as defined above.

In an embodiment, wherein the disease or condition is hypertriglyceridemia, then the prophylaxis and/or treatment comprises administering the cocrystal of beta-sitosterol and an organic carboxylic acid as defined above; preferably selected from L-lactic acid, propionic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid; preferably selected from the group consisting of L-lactic acid, propionic acid, zymonic acid, succinic acid, gallic acid and ascorbic acid; more preferably cocrystal Form 1, cocrystal Form 2, cocrystal Form, cocrystal Form 5, cocrystal Form 6, cocrystal Form 7, cocrystal Form 8, cocrystal Form 9, cocrystal Form 10, cocrystal Form 11 and cocrystal Form 12; more preferably cocrystal of Form 1, cocrystal Form 2, cocrystal Form 3 and much more preferably cocrystal Form 2.

In an embodiment, wherein the disease or condition is hypertriglyceridemia, then the prophylaxis and/or treatment comprises administering the cocrystal of beta-sitosterol and an organic carboxylic acid as defined above; preferably selected from L-lactic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid; preferably selected from the group consisting of L-lactic acid, zymonic acid, succinic acid, gallic acid and ascorbic acid; more preferably cocrystal Form 1, cocrystal Form, cocrystal Form 5, cocrystal Form 6, cocrystal Form 7, cocrystal Form 8, cocrystal Form 9, cocrystal Form 10, cocrystal Form 11 and cocrystal Form 12; more preferably cocrystal of Form 1, cocrystal Form 3.

In an embodiment, wherein the disease or condition is a mixed dyslipidaemia, then the prophylaxis and/or treatment comprise administering the combination as defined above.

In an embodiment, the combination for use as defined above, wherein the treatment comprises the simultaneously, separately or sequentially administration of the cocrystal of beta-sitosterol and an organic carboxylic acid as defined above; and a crystal of beta-sitosterol selected from the group consisting of a cocrystal of beta-sitosterol and organic alcohol as defined above, and the hydrate crystal form as defined above. It means that the treatment comprises the administration of two separate compositions containing each composition one of the crystals of the present invention.

All the embodiments disclosed above for the cocrystals, the hydrate and the combination, as well as the compositions as defined above also applies for the cocrystals, hydrate, combination or composition for use.

It is also part of the invention a food ingredient which comprises a cocrystal as defined above, a hydrate as defined above, a combination as defined above. In an embodiment, the food ingredient is selected from food supplement and functional food. The term "food supplement" refers to a concentrated source of nutrients or other substances with a nutritional or physiological effect whose purpose is to supplement the normal diet. In other terms food supplement means any food the purpose of which is to supplement the normal diet and which is a concentrated source of a vitamin or mineral or other substance with a nutritional or physiological effect, alone or in combination. The term "functional food" refers to a food or ingredient of a food that provides an additional physiological benefit beyond their basic nutritional needs.

It is also part of the invention a package comprising a cocrystal as defined above, a hydrate as defined above, a combination as defined above and instructions for use in the prophylaxis and/or treatment of a disease or condition which involves an alteration of lipid metabolism, circulating levels of lipids in the blood and/or lipid composition in tissues and organs.

Furthermore, a package comprising a composition as defined above and instructions for use in the prophylaxis and/or treatment of a disease or condition which involves an alteration of lipid metabolism, circulating levels of lipids in the blood and/or lipid composition in tissues and organs is also part of the invention.

It is also part of the invention a cocrystal of beta-sitosterol as defined above, a hydrate crystal form as defined above or a combination as defined above for use in the treatment of a disease or condition selected from the group consisting of gallstones, cold, flu, acquired immunodeficiency syndrome (AIDS), rheumatoid arthritis, tuberculosis, psoriasis, allergies, cervical cancer, fibromyalgia, systemic lupus erythematosus (SLE), asthma, hair loss, bronchitis, migraine headache, benign prostatic hyperplasia (BPH), menopause, pain, chronic fatigue syndrome, swelling and sexual dysfunction.

It is also part of the invention a cocrystal of beta-sitosterol as defined above, a hydrate crystal form as defined above or a combination as defined above for use as a wound healing agent. Furthermore, a composition as defined above for use as a wound healing agent is also part of the invention. The expression "wound healing" relates to an intricate process in which the skin (or some other organ) repairs itself after injury wound healing of any kind and at any site. It can be normal and impaired wound healing. The latter is found in particular in the case of diseases, such as diabetes mellitus, vasculitis, arterial occlusive disease, chronic venous and/or infected ulcer as well as poorly healing gastric ulcer. Impaired wound healing is also found in the case of innervations impairment such as paraplegia, leprosy, neuropathy, and decubital gangrene of persons in need of care. Impaired wound healing will also be given if weak sutures and impaired healing occur after operations, particularly of the intestines and transplantations of skin and other organs, respectively. Impaired wound healing is also found in the case of bone fractures, burns, and treatments using steroids.

As used herein, the term "wound" includes an injury to any tissue, including for example, delayed or difficult to heal wounds, and chronic wounds. Examples of wounds may include both open and closed wounds. The term "wound" may also include for example, injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I wounds limited to the epithelium; ii) Grade II wounds extending into the dermis; iii) Grade III wounds extending into the subcutaneous tissue; and iv) Grade IV (or full-thickness wounds) wounds.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

General Considerations

Beta-sitosterol, benzylic acid, lactic acid, propionic acid and piruvic acid used for the preparation of the crystalls of the present invention (cf. experimental section 1) are commercially available by Sigma-Aldrich with a chemical purity of 70%, 99%, 85%, 99%, and 98% respectively. Beta-sitosterol used as a starting material in the present invention is commercially available by Sigma-Aldrich (batch number BCB50067V and BCBM5699V). having a chemical purity equal to or higher than 70%. The PXRD of the commercial beta-sitosterol showed that beta-sitosterol was a mixture of anydrous beta-sitosterol (whose PXRD corresponds to the "LOFFET" form disclosed in Evelyn Moreno-Calvo, et al. "A New Microcrystalline Phytosterol Polymorph Generated Using CO2-Expanded Solvents". Cryst. Growth. & Design., 2014, vol. 14, pp. 58-68) and monohydrate beta-sitosterol (whose PXRD corresponds to the "TEXQOC" disclosed in Argay et al. "Crystal structure of stigmast-5-en-3β-ol monohydrate, $C_{29}H_{52}O_2$". Zeitschrift für Kristallographie, 1996, vol. 211(10), pp. 725-727) in a weight ratio 1:1. Furthermore, the GC-MS analysis of the commercially beta-sitosterol chowed that beta-sitosterol was a mixture of beta-sitosterol (83-88%), stigmasterol (3-7%) and campesterol (8-10%) (cf. section 4 of the experimental part).

Powder X-Ray diffraction (PXRD) analyses were performed by sandwiching the powder samples between polyester films of 10 micrometres of thickness or polyamide (kapton) films of 15 micrometres of thickness and analysed in a PANalytical X'Pert PRO MPD q/q powder diffractometer of 240 millimetres of radius, in a configuration of convergent beam with a focalizing mirror and a flat sample transmission geometry, in the following experimental conditions: Cu Kα radiation (λ=1.5418 Å); Work power: 45 kV and 40 mA; Incident beam slits defining a beam height of 0.4 millimetres; Incident and diffracted beam 0.02 radians Soller slits;

PIXcel detector: Active length=3.347°; 2θ/θ scans from 2 to 40°2θ with a step size of 0.026°2θ and a measuring time of 76 seconds per step. The X-ray diffractogram shows the powder X-ray diffraction pattern (intensity (counts) vs. 2-theta angle (°)) of the crystal form of beta-sitosterol of the present invention.

Single crystal X-Ray diffraction (SCXRD) structures were solved on a D8 Venture system equipped with a multilayer monochromator and a Mo microfocus (λ=0.71073 Å) has been used too. Frames were integrated with the Bruker SAINT software package using a SAINT algorithm. Data were corrected for absorption effects using the multi-scan method (SADABS). The structures were solved and refined using the Bruker SHELXTL Software Package, a computer program for automatic solution of crystal structure and refined by full-matrix least-squares method with ShelXle Version 4.8.0, a Qt graphical user interface for SHELXL computer program.

Differential Scanning Calorimetry (DSC) analyses were carried out by means of a Mettler-Toledo DSC-822e calorimeter. Experimental conditions: aluminium crucibles of 40 µL volume, atmosphere of dry nitrogen with 50 mL/min flow rate, heating rate of 10° C./min. The calorimeter was calibrated with indium of 99.99% purity.

Thermogravimetric analysis (TGA) was performed on a Mettler-Toledo TGA-851e thermobalance. Experimental conditions: alumina crucibles of 70 µL volume, atmosphere of dry nitrogen with 50 mL/min flow rate, heating rate of 10° C./min.

The HPLC-MS analysis of the cocrystals of beta-sitosterol and the hydrate crystal of the present invention showed that they comprises a mixture of beta-sitosterol (83-88%), stigmasterol (3-7%) and campesterol (8-10%) (cf. section 4 of the experimental part). In particular, the cocrystals of beta-sitosterol and an organic carboxylic acid selected from the group consisting of L-lactic acid, propionic acid, zymonic acid, succinic acid, ascorbic acid, gallic acid, 2,4-dihydroxybenzoic acid, 3,4-dihydroxybenzoic acid, 3-hydroxybenzoic acid, 4-hydroxybenzoic acid and 3,5- dihydroxybenzoic acid; the cocrystals of beta-sitosterol and an organic alcohol selected from the group consisting of benzyl alcohol, ethanol and isopropoanol; and hydrate crystal form of beta-sitosterol having a 1.25 molecules if water per molecule of beta-sitosterol of the present invention comprises a mixture of beta-sitosterol (83-88%), stigmasterol (3-7%) and campesterol (8-10%).

1. Cocrystal of Beta-Sitosterol and a Hydrogen Bond Donor Coformer 1.1. Cocrystal of Beta-Sitosterol and an Organic Carboxylic Acid 1.1.1. Cocrystal of Beta-Sitosterol and L-Lactic Acid Preparation Process A suspension of beta-sitosterol (20 mg, 0.048 mmol), L-lactic acid (0.1 mL) and ethyl acetate (0.2 mL) was stirred at room temperature for 5 days. The crystal thus obtained was filtered and dried under vacuum.

1.1.2. Cocrystal of Beta-Sitosterol and Propionic Acid

Preparation Process 1

A solution of beta-sitosterol (500 mg, 1.21 mmol) and propionic acid (2.5 mL) was stirred at room temperature for one day open to air. The crystal thus obtained was filtered and dried under vacuum.

Preparation Process 2

Beta-Sitosterol (50 g) with propionic acid (500 mL) was suspended until total dissolution (1 hour). Water (1000 mL) was added at room temperature and a white solid precipitated with a gentle stirring. The crystal thus obtained was filtered and dried under vacuum (about 200 mm Hg) for 2 hours. The crystal was finally dried by passing an air flow through the filtered crystal for 8 hours.

1.1.3. Cocrystal of Beta-Sitosterol and Zymonic Acid

Preparation Process

A solution of beta-sitosterol (500 mg, 1.21 mol), pyruvic acid (2.5 mL) and acetone (5.0 mL) was stirred at room temperature for 1 day. The crystal thus obtained was filtered and dried under vacuum.

1.1.4. Cocrystal of Beta-Sitosterol and Gallic Acid

Preparation Process

Beta-sitosterol (625 mg, 1.51 mmol) and gallic acid (97.7 mg, 0.57 mmol) were suspended in ethyl acetate (5.0 mL) at room temperature and stirred overnight. The crystal thus obtained was filtered and dried under vacuum.

1.1.5 Cocrystal of Beta-Sitosterol and 2,4-Dihydroxybenzoic Acid

Preparation Process

Beta-sitosterol (100 mg, 0.241 mmol) and 2,4-dihydroxybenzoic acid (41 mg, 0.266 mmol) were suspended in ethyl acetate (0.3 mL) at room temperature and stirred overnight. The crystal thus obtained was filtered and dried under vacuum.

1.1.6 Cocrystal of Beta-Sitosterol and 3,4-Dihydroxybenzoic Acid

Preparation Process 3,4-dihydroxybenzoic acid (4.0 g, 25.95 mmol) was stirred in ethyl acetate (15 mL) during 2 hours. The suspension was filtered and beta-sitosterol (2.0 g, 4.82 mmol) was added and it was stirred at room temperature overnight. The crystal thus obtained was filtered and dried under vacuum.

1.1.7 Form a of Cocrystal of Beta-Sitosterol and 3,5-Dihydroxybenzoic Acid

Preparation Process

Beta-sitosterol (100 mg, 0.241 mmol) and 3,5-dihydroxybenzoic acid (41 mg, 0.266 mmol) were suspended in ethyl acetate (0.3 mL) at room temperature and stirred overnight. The crystal thus obtained was filtered and dried under vacuum.

1.1.8 Form B of Cocrystal of Beta-Sitosterol and 3,5-Dihydroxybenzoic Acid

Preparation Process

Beta-sitosterol (100 mg, 0.241 mmol) and 3,5-dihydroxybenzoic acid (41 mg, 0.266 mmol) were dissolved in ethyl acetate (2.0 mL) at room temperature. The solution was stirred overnight opened to the air. The crystal thus obtained was filtered and dried under vacuum.

1.1.9 Cocrystal of Beta-Sitosterol and 3-Hydroxybenzoic Acid

Preparation Process

Beta-sitosterol (100 mg, 0.241 mmol) and 3-hydroxybenzoic acid (37 mg, 0.268 mmol) were suspended in ethyl acetate (0.4 mL) at room temperature and stirred overnight. The crystal thus obtained was filtered and dried under vacuum.

1.1.10 Form A of the Cocrystal of Beta-Sitosterol and 4-Hydroxybenzoic Acid

Preparation Process 4-hydroxybenzoic acid (4.0 g, 28.96 mmol) was stirred in ethyl acetate (15 mL) during 2 hours. The suspension was filtered and beta-sitosterol (2.5 g, 6.03 mmol) was added and the mixture was stirred at room temperature overnight. The crystal thus obtained was filtered and dried under vacuum.

1.1.11 Form B of the Cocrystal of Beta-Sitosterol and 4-Hydroxybenzoic Acid

Preparation Process

Beta-sitosterol (100 mg, 0.241 mmol) and 4-hydroxybenzoic acid (37 mg, 0.268 mmol) were dissolved in ethyl acetate (2.0 mL) at room temperature and stirred opened to the air overnight. The crystal thus obtained was filtered and dried under vacuum.

1.2. Cocrystal of Beta-Sitosterol and an Organic Alcohol 1.2.1. Cocrystal of Beta-Sitosterol and Benzyl Alcohol Preparation Process A solution of beta-sitosterol (1 g, 2.411 mmol) in benzyl alcohol (4.0 mL) was heated to 70° C. and it was slowly cooled down to room temperature in 1 hour. Then, the temperature was cooled down to 4-8° C. and was kept for 1 day until a gel was precipitated. The solution was decanted and pentane was added until clear solution and then the solution was evaporation to dryness. After that, diethyl ether was added until clear solution and it was also evaporated to dryness to obtain a gel, which evolved to a solid overnight. The solid thus obtained was filtered and dried under vacuum to obtain the cocrystal of beta-sitosterol and benzyl alcohol.

2. Hydrate Crystal Form of Beta-Sitosterol

Preparation Process

A solution of beta-sitosterol (500 mg, 1.21 mmol), propionic acid (2.5 mL) and acetone (5 mL) was stirred at room temperature for one day. The crystal thus obtained was filtered and dried under vacuum to obtain the hydrate crystal form of the present invention.

3. Activity Test

The activity test is focused on determining the percentage of reduction of the circulating levels of glucose, cholesterol, triglycerides and beta-sitosterol after oral ingestion of lipids or an oral ingestion of lipids supplemented with either the crystals of beta-sitosterol of the present invention or a comparative authorized beta-sitosterol which is outside the scope of the present invention.

The comparative beta-sitosterol used in the activity test corresponds to the compound authorized in the Commission Decision of 31 Mar. 2004 authorising the placing on the market of yellow fat spreads, salad dressings, milk type products, fermented milk type products, soya drinks and cheese type products with added phytosterols/phytostanols as novel foods or novel food ingredients under Regulation (EC) No 258/97 of the European Parliament and of the Council (notified under document number C(2004) 1243)-2004/333/EC (cf. Official Journal L 105, 14 Apr. 2004 P. 0040-0042). The authorized beta-sitosterol has the following composition (measured by Gas Chromatography—Flame Ionization Detector—GC-FID): <80% beta-sitosterol, <15% beta-sitostanol, <40% campesterol, <5% campestanol, <30% stigmasterol, <3% brassicasterol, <3% other esterols/stanols.

Samples

Comparative sample A (control-vehicle): an oral load of lard (2.5 g/kg BW)

Comparative sample B (reference): an oral load of lard (2.5 g/kg BW) supplemented with commercial authorized beta-sitosterol (0.513 g/kg BW, which corresponds to 2.5× the recommended human equivalent dose translated to hamster).

Sample C: an oral load of lard (2.5 g/kg BW) supplemented with the cocrystal of beta-sitosterol and propionic acid of the present invention (0.513 g/kg BW).

Sample D: an oral load of lard (2.5 g/kg BW) supplemented with the hydrate crystal form of beta-sitosterol of the present invention (0.513 g/kg BW).

Sample E: an oral load of lard (2.5 g/kg BW) supplemented with cocrystal of beta-sitosterol and benzyl alcohol of the present invention (0.513 g/kg BW).

BW stands for bodyweight

Animals and Treatment

The animals used in the activity test were Golden Syrian male Hamsters of 16 weeks of age. Five experimental groups of 7 animals per group were established. The experimental groups were the following:

Comparative group A: treated with the comparative sample A (control-vehicle);

Comparative group B: treated with the comparative sample B (reference);

Test group C: treated with Sample C;

Test group D: treated with Sample D; and

Test group E: treated with Sample E.

The test was performed to animals subjected to a caloric restriction of 40% during the previous 24 hours. In all experimental groups, the lard was supplemented by 0.513 g/kg BW of comparative beta-sitosterol or crystals of the present invention, which is equivalent to a 2.5 times the dose recommended for human use and adapted for use in hamster (Cf. Reagan-Shaw, et al, "Dose translation from animal to human studies revisited". FASEB J. 2007, vol. 22, pp. 659-661.

Sampling

Before the test and at initial time (T0), blood was collected from the saphenous vein with heparinized capillaries. Then, at 5 hours after receiving the oral load of lard (T5), the animals received an intraperitoneal injection of lethal anaesthesia based on the active pentobarbital sodium (lethal dose at 200 mg/mL of pentobarbital, Vetoquinol). Amounts of administration of the lethal dose of sodium pentobarbital (pre-diluted with saline at 25 mg/mL) were calculated based on the individual weight of each animal.

After verifying that the animal was sedated, it was exsanguinated by making a small incision at the level of the rib cage, followed by collection of blood by cardiac puncture (5 mL syringe with 21 G needles). The interior of the needle and syringe were previously soaked with filtered EDTA (0.5M, pH=8) to prevent blood clotting. Blood was centrifuged at 3500 rpm for 10 minutes at 4° C. to obtain the plasma, which was frozen at −20° C. until use.

Determinations

Plasma cholesterol levels have been determined with the total cholesterol kit supplied by Biosystems (ref: M11505c-0518). Plasma triglyceride levels have been determined with the Sigma Triglyceride determination kit (ref.: TR0100). Blood glucose concentrations were measured by means of test strips from the Accu-check Aviva glucometer (Roche, ref.: 06453970).

Determination of phytosterols in plasma was performed after saponification and derivatization by gas chromatography (GC-7890A, Agilent Technologies) combined with ionisable flame detector (GS-FID using a HP-5MS column (length 30 m, diameter 0.25 mm) and a helium mobile phase flow of 0.8 mL·min-1. (Cf. Garcia-Llatas, G. et al. "Simultaneous quantification of serum phytosterols and cholesterol precursors using a simple gas chromatographic method". European Journal of Lipid Science and Technology, 2012, vol 114(5), pp. 520-526; and Andrade, I. et al. "Advances in analytical methods to study cholesterol metabolism: the determination of serum noncholesterol sterols". Biomedical Chromatography, 2013, vol. 27(10), pp. 1234-1242).

Statistical Analysis

Data results were presented as the mean±error of mean (SEM). Statistical analysis was performed using SPSS 1.9 software (Chicago, Ill., USA). The comparison between groups was performed by analysis of variance (ANOVA one-way) followed by Fisher's post-hoc analysis (LSD, of the least significant difference). The comparison between T0 and T5 of the different groups was performed using the ANOVA test of repeated measurements (ANOVA), followed by LSD analysis and t-test of paired means.

Results

A. Glucose

No significant differences were observed in the circulating glucose levels between all experimental groups at the times analysed.

B. Cholesterol

Figure 14:
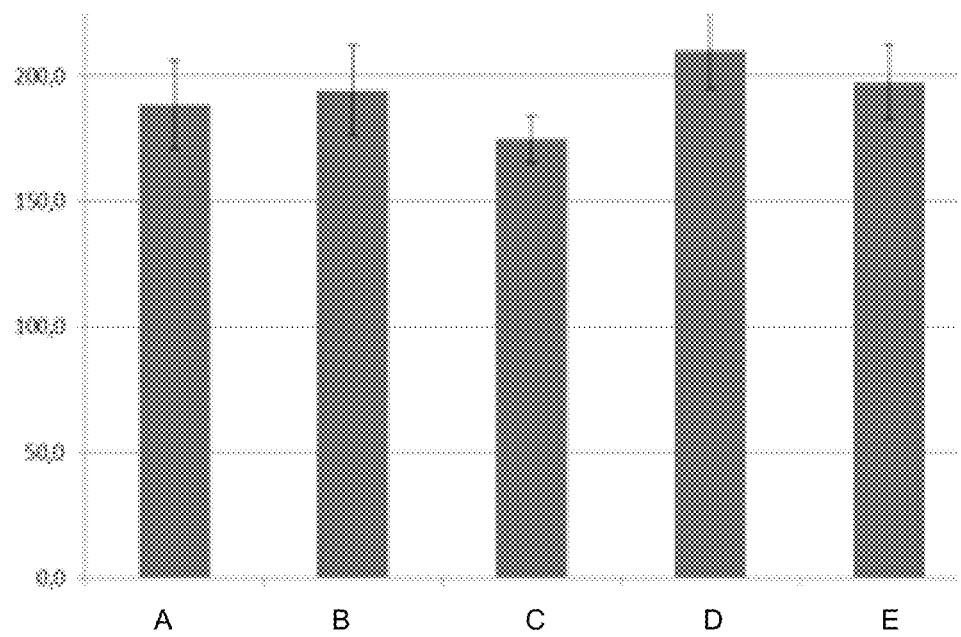
FIG. 14 section 1A shows the cholesterol concentrations expressed as mg/dL at initial time (T0; before the treatment); and section 1B shows the decrease in cholesterol concentration expressed as mg/dL at 5 h post-oral fat load (T5) versus T0 in each experimental group (adult male, Golden Syrian Hamsters). The experimental groups are the following: A corresponds to vehicle group (fat-load), B corresponds to the commercial authorized sample of beta-sitosterol, C corresponds to the cocrystal of beta-sitosterol with propionic acid of the present invention, D corresponds to the hydrate crystal form of beta-sitosterol of the present invention, and E corresponds to the crystal of beta-sitosterol and benzyl alcohol of the present invention. Letters a and b show differences between groups, wherein a denotes p=0.064 for Group D vs. A and b denotes p=0.059 for Group E vs. A.
Figure 14:
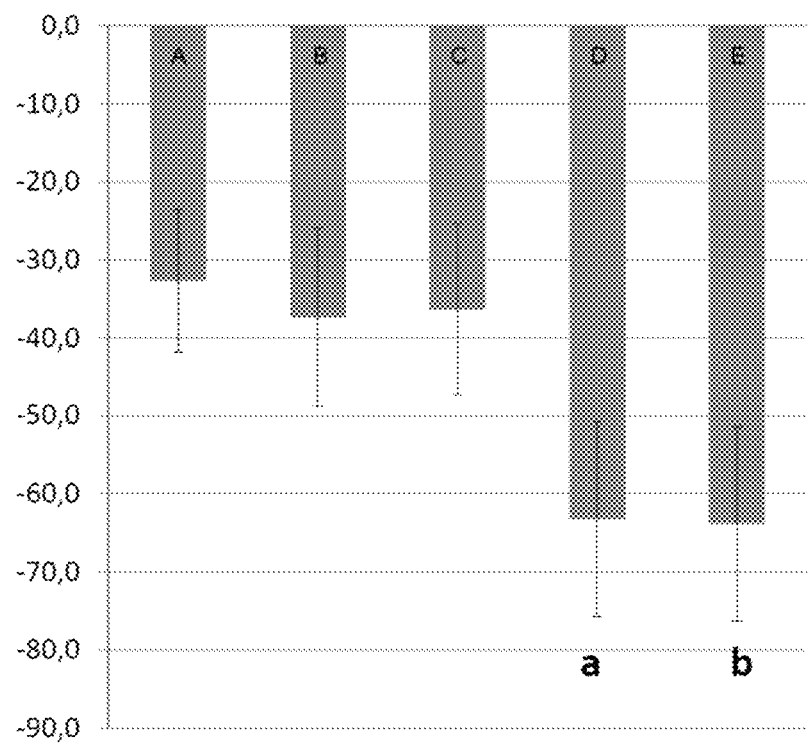

As it is shown in FIG. 14, plasma cholesterol levels at initial time (T0) did not differ between all experimental groups. Then, the administration of the cocrystal of beta-sitosterol and propionic acid (Test sample C) of the present invention decreased the plasmatic cholesterol levels (21%), measured at 5 h, in the same way as the comparative samples A and B (17% and 25% respectively).

Nevertheless, the administration of the hydrate crystal form of beta-sitosterol of the invention (test sample D) and the cocrystal of beta-sitosterol and benzyl alcohol (Test sample E) significantly lowered the plasmatic cholesterol concentrations (in absolute value) an in a percentage of 29% and 31% respectively (p=0.064 and p=0.059 respectively vs. comparative sample control A).

C. Triglycerides

Figure 15:
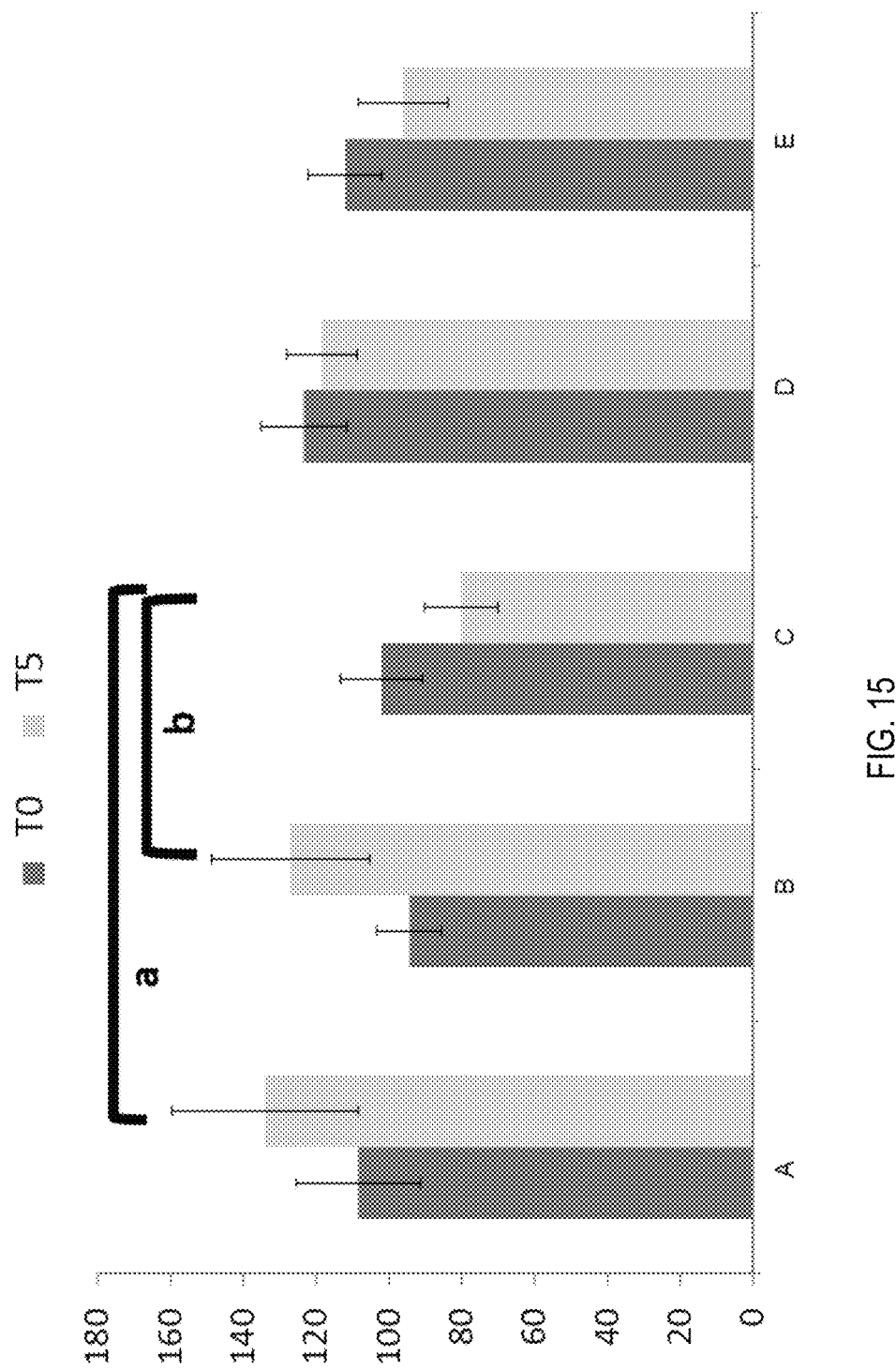
FIG. 15 shows plasma triglyceride concentrations expressed as mg/dL at initial time (T0; before treatment; left column) and at 5 h post-oral fat load (T5-right column) in each experimental group. The experimental groups are the following: A corresponds to vehicle group (fat-load), B corresponds to a commercial authorized sample of beta-sitosterol, C corresponds to the cocrystal of beta-sitosterol with propionic acid of the present invention, D corresponds to the hydrate crystal form of beta-sitosterol of the present invention, and E corresponds to the crystal of beta-sitosterol and benzyl alcohol of the present invention. Compound C showed lower levels at T5 in comparison with both Compound A and compound B. Letters a and b show differences between groups, wherein a denotes p=0.013 and b denotes p=0.032.

As it is shown in FIG. 15, plasma triglyceride levels at initial time (T0) did not differ between all experimental groups.

Nevertheless, the administration of the comparative samples A and B led to a slight increase in triglyceridemia at 5 h (T5) of 44% and 39% respectively. In comparison, the administration of hydrate crystal form of beta-sitosterol of the invention (test sample D) and the cocrystal of beta-sitosterol and benzyl alcohol (test sample E) attenuated the increase in the triglyceridemia and caused a reduction of 2% and 7% of the triglyceride concentration respectively.

Furthermore, the administration of the cocrystal of beta-sitosterol and propionic acid (test sample C) of the present invention significantly lowered in a 20% the plasmatic triglyceride concentration (p=0.012 T0 vs. T5 and p=0.06 vs. comparative sample B).

D. Sitosterolemia

Figure 16:
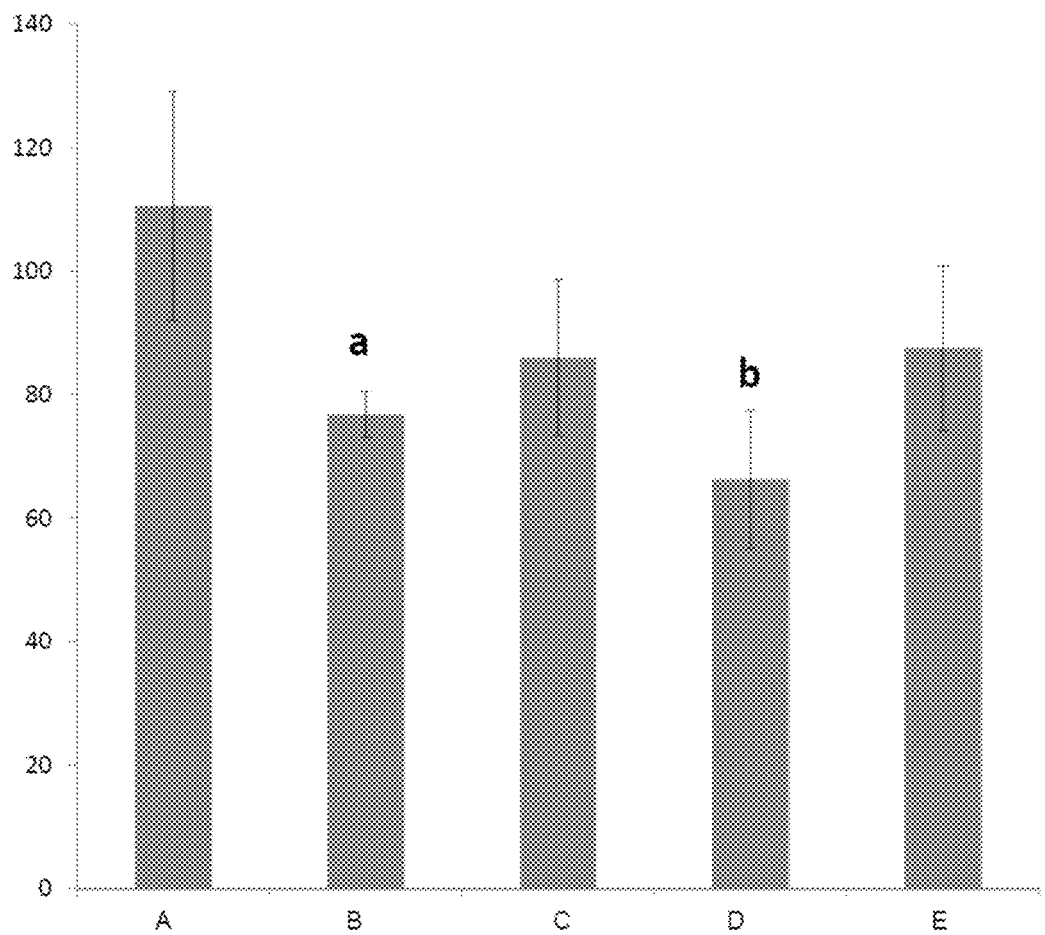
FIG. 16 shows percentage of variation on β-sitosterol plasma levels associated at 5 h post-treatment (T5) in comparison with basal levels at initial time (T0) in the different experimental groups. The experimental groups are the following: A corresponds to vehicle group (fat-load), B corresponds to a commercial authorized sample of beta-sitosterol, C corresponds to the cocrystal of beta-sitosterol with propionic acid of the present invention, D corresponds to the hydrate crystal form of beta-sitosterol of the present invention, and E corresponds to the crystal of beta-sitosterol and benzyl alcohol of the present invention. Compound B showed a decrease in comparison with control (group A) and compound D showed a decrease in comparison with control (group A). Letters a and b show differences between groups, wherein a denotes p=0.061 and b denotes p=0.020.

As it is shown in FIG. 16, just after the administration of the comparative sample A circulating β-sitosterol levels were not modified.

Meanwhile, the administration of the comparative sample B promoted a decrease in circulating levels of 23% with respect to the values at initial time (T0) (p=0.061 vs. comparative sample A-control). In the same way, the administration of the cocrystal of beta-sitosterol and propionic acid (test sample C) and the cocrystal of beta-sitosterol and benzyl alcohol (test sample E) of the present invention also decreased in a similar way the circulating levels of β-sitosterol (14% and 12%, respectively vs. their T0 value).

Nevertheless, a significantly marked effect in lowering the circulating levels of β-sitosterol for hydrate crystal form of beta-sitosterol (test sample D) was observed. Particularly, a reduction of 34% in relation to its T0 value was observed (p=0.02 vs. comparative sample A-control).

4. Determination of the Amount of Stigmasterol and Campesterol in the Beta-Sitosterol Used as Starting Material and in the Cocrystals of the Present Invention This test is focused on determining the percentage of stigmasterol and campesterol present in the commercially available beta-sitosterol used as starting material in the preparation of the cocrystals and hydrate of the present invention. Furthermore, this test is also focused on determining the percentage of stigmasterol and campesterol that is still present in the cocrystals and hydrate of the present invention.

4.1. Analytical Methodologies 4.1.1. Gas Chromatography-Mass Spectrometry (GS-MS)

Tested samples: 1.01 mg of the tested compound were dissolved in 1 mL of dichloromethane:methanol (1:1). The tested sample was the cocrystal of beta-sitosterol and gallic acid Form 5 of the present invention and beta-sitosterol commercially obtained by sigma-aldrich (batch BCB50067V).

Tested and standard samples derivatization: 100 μL of both solutions were totally dried. Then, 150 μL of N,O-Bis(trimethylsilyl)trifluoroacetamide (BSTFA) were added and the resulting solution was heated up to 150° C. for 1 hour. The solution was cooled down at room temperature and it was totally dried under Nitrogen ($N_2$) flow. Both solids were suspended in 1 mL of hexane. Finally, 1 μL of the each solution were injected.

Equipment: Thermo Scientific Trace GC Ultra connected to Thermo Scientific ITQ 900.

Column: Teknokroma Sapiens X5-MS 30 m×0.25 mm d.i.×0.25 um d.f.

Chromatographic conditions:
Injector: Injector split/splitless
Injector mode: splitless
Splitless time: 1 min.
Injector temperature: 300° C.
Gas: He (1 mL/min)
Oven method: Initial temperature: 40° C., isothermic: 1 min
Step 1: Heating from 40° C. to 180° C. at a rate of 15° C./min.
Step 2: Heating from 180° C. to 320° C. at a rate of 6° C./min., isothermic: 25 min
Detector: Ion source temperature: 200° C.
Interface temperature: 320° C.
Solvent delay: 5 min.
Mass range: 50 to 900 uma.

4.1.2. High-Performance Liquid Chromatography (HPLC)

Tested Samples: 10 mg of the tested compound were disolved in 10 mL of tetrahydrofurane (THF). Each sample was prepared three times. The tested samples were the following: cocrystal of beta-sitosterol and propionic acid Form 2, cocrystal of beta-sitosterol and zymonic acid Form 3, hydrate crystal of beta-sitosterol having 1.25 molecules of water, cocrystal of beta-sitosterol and gallic acid Form 5, cocrystal of beta-sitosterol and 2,4-dihydroxybenzoic acid Form 6, cocrystal of beta-sitosterol and 3,4-dihydroxybenzoic acid Form 7, Form A of the cocrystal of beta-sitosterol and 4-hydroxybenzoic acid cocrystal Form 11 and Form B of the cocrystal of beta-sitosterol and 4-hydroxybenzoic acid Form 12.

Standard sample: beta-Sitosterol from the Ph. Eu. Reference Standard, ref. (Y0001615), (72.5% $C_{29}H_{50}O$).

Calibration curve: a stock solution of approximately 1500 mg/L beta-Sitosterol (10 mg/5 mL) in THF was prepared. Three more standards between 0.4 mg/L and 1100 mg/L by dilution in THF were prepared. Every standard was injected twice.

Equipment:
Chromatograph: Waters Alliance 2695.
Detector: Waters PDA 2996.
Balance: Mettler Toledo AT261.
Software: Empower, Waters.
Analytical conditions:
Column: YMC-Pack Pro C18, 5 μm, 12 nm, 50×4.6 mm.
Mobile phase: Methanol/Acetonitrile 20:80 (v/v)
Flow rate: 1.0 mL/min.
Injection: 10 μL
Detection: 210 nm.

4.1.3. High Performance Liquid Chromatography-High Resolution Mass (HPLC-HRMS)

Figure 41:
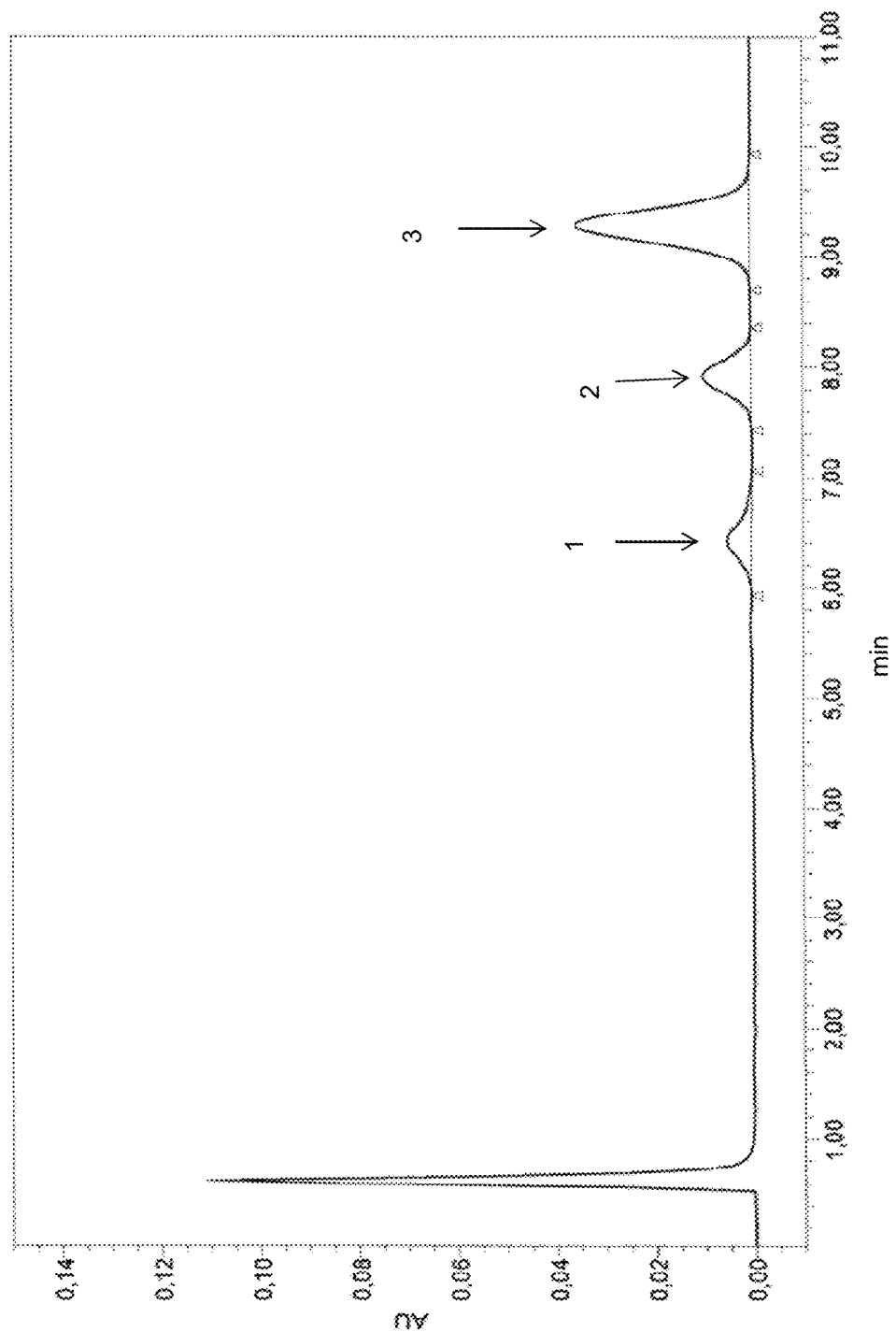
FIG. 41 shows the chromatogram of the HPLC analysis of the standard sample of beta-sitosterol of the Ph. Eur. The chromatogram expresses the area (AU) versus minutes (min). In the chromatogram: 1 corresponds to peak 1 at 6.433 min which is stigmasterol; 2 corresponds to peak 2 at 7.933 min which is campesterol and 3 corresponds to peak 3 at 9.267 min which is beta-sitosterol.
Figure 42:
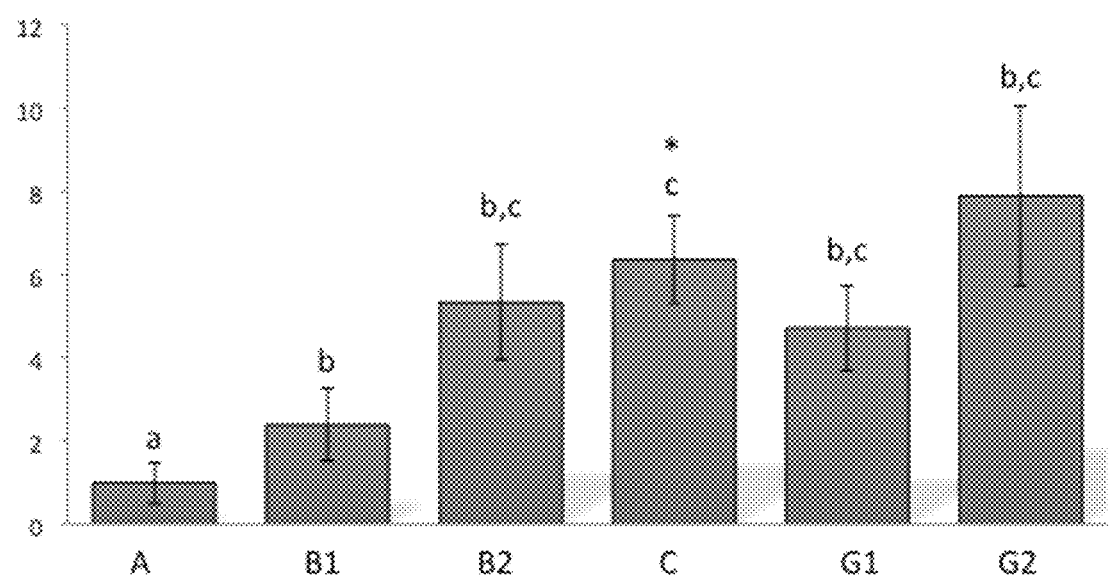
FIG. 42 shows the circulating levels of beta-sitosterol. The data is shown as the Fold-Change ratio of plasma beta-sitosterol in the reference and test groups respect to the control group (comparative group A, which was set at 1.0). Mean±SEM (n=7-8 animals/group). a≠b≠c (p≤0.050, one-way ANOVA and LSD post-hoc test); * different respect to reference B1 (p<0.05, Student's t test). The experimental groups are the following: Comparative group A corresponds to high-fat diet fed with the comparative sample A (control), comparative group B1 corresponds to high-fat diet fed with the comparative sample B1—commercial authorized beta-sitosterol (reference), comparative group B2 corresponds to high-fat diet fed with the comparative sample B2-commercial authorized beta-sitosterol (reference), test group C corresponds to high-fat diet fed with Sample C (cocrystal of beta-sitosterol and propionic acid Form 2), test group G1 corresponds to high-fat diet fed with Sample G1 (cocrystal of beta-sitosterol and gallic acid Form 5), and test group G2 corresponds to high-fat diet fed with Sample G2 (cocrystal of beta-sitosterol and gallic acid Form 5). Letters a and b show differences between groups, wherein a denotes p=0.013 and b denotes p=0.032.

The tested sample was the cocrystal of beta-sitosterol and gallic acid Form 5 of the present invention Equipment: Chromatograph: Accela (Thermo Fisher Scientific).
Detector: Accela (PDA)+LTQ-Orbitrap Velos (HRMS).
Software: Xcalibur (Thermo Fisher Scientific).
Analytical conditions: Column: YMC-Pack Pro $C_{18, 5}$ μm, 12 nm, 50×4.6 mm.
Mobile phase: Methanol/Acetonitrile 20:80 (v/v)
Flow rate: 1.0 mL/min.
Injection: 10 μL
Detection (UV): 210 nm.
Ion source (MS): APCI
Polarity (MS): Positive 4.1.4. Results 4.1.4.1. Results Obtained by the HPLC Analysis Three significant peaks have been observed during the HPLC analysis of the standard β-Sitosterol, Ph. Eur. (cf. FIGS. 41) at 6.433, 7.933 and 9.267 min. They were assigned to Stigmasterol, Campesterol and β-Sitosterol respectively according to HRMS analysis having the following structures:

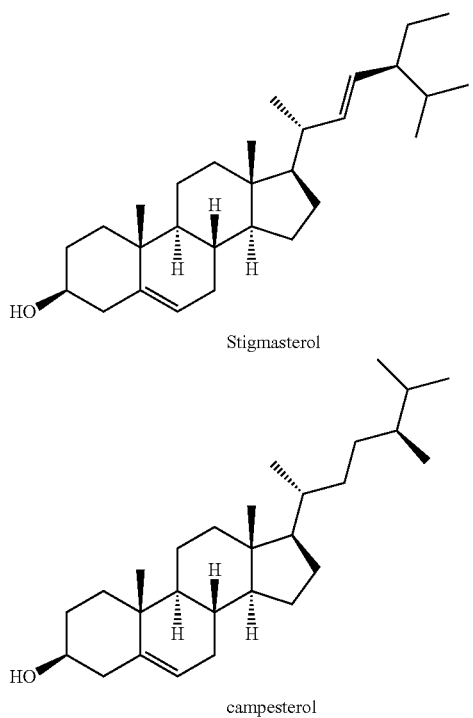

Stigmasterol campesterol

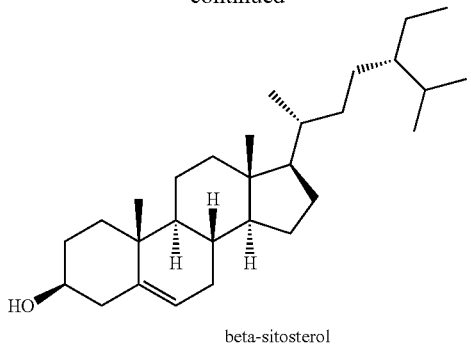

beta-sitosterol

The molecular weight of each compound were the following:

Stigmasterol (peak 1): MS (ES) (+): 395.37 $[C_{29}H_{47}]^+$.

Campesterol (peak 2): MS (ES) (+): 383.37 $[C_{28}H_{47}]^+$.

β-Sitosterol (peak 3) MS (ES) (+): 397.38 $[C_{29}H_{49}]^+$.

The same peaks have been observed in all the tested samples as defined above. The results are summarized in the following Table 14.

Table 14 represents the HPLC quantification of stigmasterol (peak 1), campesterol (peak 2) and beta-sitosterol in the tested samples. The abbreviature RT corresponds to the retention time (RT) expressed in minutes (min) and the area is expressed in percentage (W/W).

TABLE 14

| Samples | Peak 1 (Stigmasterol) | | Peak 2 (campesterol) | | β-Sitosterol | |
|---|---|---|---|---|---|---|
| | RT (min) | Area (%) | RT (min) | Area (%) | RT (min) | Area (%) |
| Standard sample of beta-Sitosterol from the Ph. Eu. Reference Standard, ref. (Y0001615) | 6.443 | 10.75 | 7.933 | 19.06 | 9.267 | 70.19 |
| cocrystal of beta-sitosterol and propionic acid Form 2 | 6.256 | 7.09 | 7.777 | 9.76 | 9.167 | 83.14 |
| cocrystal of beta-sitosterol and zymonic acid Form 3 | 6.133 | 7.33 | 7.700 | 9.35 | 9.067 | 84.32 |
| hydrate crystal of beta-sitosterol having 1.25 molecules of water | 6.267 | 3.70 | 7.800 | 9.55 | 9.200 | 86.75 |
| cocrystal of beta-sitosterol and gallic acid Form 5 | 6.367 | 5.51 | 7.822 | 9.38 | 9.222 | 85.11 |
| cocrystal of beta-sitosterol and 2,4-dihydroxybenzoic acid Form 6 | 6.284 | 3.05 | 7.717 | 8.63 | 9.084 | 88.32 |
| cocrystal of beta-sitosterol and 3,4-dihydroxybenzoic acid Form 7 | 6.284 | 5.45 | 7.767 | 9.27 | 9.167 | 85.27 |
| Form A of the cocrystal of beta-sitosterol and 4-hydroxybenzoic acid cocrystal Form 11 | 6.250 | 6.03 | 7.767 | 9.16 | 9.167 | 84.82 |
| Form B of the cocrystal of beta-sitosterol and 4-hydroxybenzoic acid Form 12 | 6.252 | 3.59 | 7.733 | 9.06 | 9.100 | 87.35 |
| Average of all the tested cocrystal samples with standard deviation (SD) | 6.262 ± 0.064 | 5.22 ± 1.62 | 7.760 ± 0.041 | 9.27 ± 0.34 | 9.147 ± 0.056 | 85.64 ± 1.71 |

4.1.4.2. Results Obtained by the GS-MS Analysis

Three significant peaks have been observed during GS-MS of both trimethylsilyl derivative samples of the cocrystal of beta-sitosterol and gallic acid Form 5 and commercially available beta-sitosterol of sigma-aldrich (Batch number BCB50067V), which confirm with high precision the identity of the three phytosterols present in all the solid forms of this invention.

The observed peaks were the following:
Beta-sitosterol-TMS: molecular weight of 488.33;
Campesterol-TMS: molecular weight 472.37; and
Stigmasterol-TMS: molecular weight of 486.36.

4.1.4.3. Conclusion

The above results show that both the beta-sitosterol used as starting material as well as the obtained cocrystals and the hydrate form of beta-sitosterol of the present invention comprises from 3 to 7 area/area measured by HPLC of stigmasterol, from 8 to 10 area/area measured by HPLC of campesterol and from 83 to 88 area/area measured by HPLC beta-sitosterol.

5. Solubility Test

This test is focused on evaluating the solubility in Fasted State Simulated Intestinal Fluid (FaSSIF-V2).

5.1. Samples

Comparative sample A (reference): Standard sample of beta-Sitosterol from the Ph. Eu. Reference Standard, ref. (Y0001615)

Sample A: hydrate crystal of beta-sitosterol having 1.25 molecules of water of the present invention Sample B: cocrystal of beta-sitosterol and gallic acid Form 5 of the present invention

5.2. Solubilization Media

Solubility is determined in FaSSIF-V2 media, prepared as stated by Biorelevant.com using maleic acid buffer (pH=6.5).

5.3. Methods

5.3.1. Shake-Flask (SF) Procedure

All experiments are done under temperature control at 25±1° C. The weight of tested samples expressed in mg, and FaSSIF final volume expressed in mL are as defined in Table below:

| Sample | Weight (mg) | FaSSIF volume (mL) |
|---|---|---|
| Comparative sample A | 10 | 2 |
| Sample A | 10 | 2 |
| Sample B | 15 | 2 |

Shaking time: 24 h in a rotational stirrer. After 4-5 h of shaking, pH is measured and readjusted to the initial value (6.5) in case it is needed.

Equilibration time: 24 h

Final pH measurement

Phase separation: filtration through a hydrophilic filter (PTFE membrane, 0.45 µm porous size, 4 mm diameter, Millex-LH, Millipore). Before the filtration, the filter was conditioned with sample solution for 1 h. After that time, filtration started rejecting the first drops of sample.

Solid form characterization: solid obtained after filtration is analysed by XRPD to know the exact solid form obtained after the shake-flask procedure. In case of cocrystals, XRPD analysis confirms that experiments are done under eutectic point conditions.

Liquid phase is used for API and coformer quantification.

5.3.2. HPLC Quantification

Instrument: Shimadzu HPLC, with diode array detector (SPD-M10AVPI), two pumps (LC-10ADVP), autoinjector (SIL-10ADVP) and column oven (CTO-10ASVP).

Column:
For comparative sample A and sample A quantification: Phenomenex Kinetex C18, 100×4.6 mm, 2.6 µm. For sample B quantification: Phenomenex Luna C18, 150×4.6 mm, 5 µm.

Conditions:
For comparative sample A and sample A quantification: Mobile phase composed of 80% Methanol-20% Acetonitrile. Isocratic conditions. Flow: 0.8 mL/min. Injection volume: 20 µL.

For sample B quantification: Mobile phase composed of 20 mM formic acid at pH=3 (A) and methanol (B). Gradient conditions: 0-3 min, 5% B; 8 min, 10% B; 15 min, 100% B; 17 min, 5% B; 25 min, 5% B. Flow: 1 mL/min. Injection volume: 10 µL.

Quantification wavelength: 210 nm for comparative sample A and 280 nm for sample A.

5.4. Results

Part 1: Calibration Curves

Table below provides the information related to the standards of the tested samples and coformers used for the calibration, as well as the average quality parameters obtained from the calibration curves.

| | | | | Calibration | | |
|---|---|---|---|---|---|---|
| Sample | Purity (%) | Solvent | $t_R$ (min) | Range concentration (mg/L) | $R_2$ | F |
| Comparative sample A | 95.17 | Methanol: acetonitrile (80:20) | 4.8 | 0.5-10 | >999 | >3000 |
| Sample B | 99.4 | Methanol: water (5:95) | 7.2 | 25-200 | >999 | >2000 |

Part 2: Limits of Detection and Quantification

LOD and LOQ for comparative sample A have been determined as follows:

LOQ: is the concentration at which S/N ratio is 10. In order to determine LOQ, different concentrations of comparative sample A have been injected, until the desired S/N ratio is obtained. LOQ=0.3 mg L-1.

LOD: is the concentration at which S/N ratio is 3. In order to determine LOD, different concentrations comparative sample A have been injected, until the desired S/N ratio is obtained. LOD=0.1 mg L-1.

Part 3: Solubility Results

The amounts of comparative sample A, sample A and sample B in the filtered solutions coming from Shake-Flask (SF) experiments have been quantified according to the described methodology.

Solubility of the samples A and B has been calculated through the equilibrium concentrations in the eutectic point as described in "S. J. Bethune, N. Huang, A. Jayasankar, N. Rodriguez-Hornedo, Crystal Growth and Design 9, 2009, 3976-3988", taking into account the stoichiometry of each sample.

Table below shows the results obtained for the different tested samples, where log S is the logarithm of S in mol/L, [API] is the concentration of beta-sitosterol in the solutions coming from SF experiments, n is the number of replicates, and PXRD analysis indicates the solid/s form/s obtained after the SF experiments.

| Sample | Log S | [API] 8 mg/mL | N | PXRD analysis |
|---|---|---|---|---|
| Comparative sample A | −6.07 (0.08) | 0.36 (0.06) | 5 | Beta-sitosterol |
| Sample A | −5.3 80.2) | 2.5 (1) | 8 | hydrate crystal of beta-sitosterol having 1.25 molecules of water + monohydrate crystal of beta-sitosterol of the state of the art |
| Sample B | −4.7 (0.1) | 3.0 (1.5) | 9 | cocrystal of beta-sitosterol and gallic acid Form 5 + monohydrate crystal of beta-sitosterol of the state of the art |

The obtained results point out that the cocrystal of beta-sitosterol and gallic acid of the present invention is more soluble than the remaining tested samples. The hydrate crystal of beta-sitosterol having 1.25 molecules of water 1:1.25 form of the present invention is more soluble than the commercially available beta-sitosterol (comparative sample A)

Without being bound to any theory, it seems that the amount of beta-sitosterol in solution depends on the solid form in equilibrium with the solution. This is in accordance with PXRD results, which indicate that in the cocrystal of beta-sitosterol and gallic acid, the amount of beta-sitosterol in solution is in equilibria with the monohydrate crystal of beta-sitosterol disclosed in the art.

6. Bioavailability Assessment

The bioavailability assessment of the crystals of beta-sitosterol of the present invention has been carried out by determining the beta-sitosterol levels in plasma samples from animals (hamsters) submitted during three weeks with a high-fat diet supplemented with either the crystals of beta-sitosterol of the present invention or a comparative standard sample of beta-Sitosterol available from the Ph. Eu. Reference Standard, ref. (Y0001615), which is outside the scope of the present invention.

6.1. Tested Samples

Comparative sample A (control): high-fat diet (60% of calories from fat, D12492, Research diets, USA)

Comparative sample B1 (reference): high-fat diet (60% of calories from fat, D12492, Research diets, USA) supplemented with comparative standard sample of beta-sitosterol (0.264 g/kg BW, which corresponds to the recommended human equivalent dose (35.71 mg/Kg or 2.5 g/70 Kg) translated to hamster).

Comparative sample B2 (reference): high-fat diet (60% of calories from fat, D12492, Research diets, USA) supplemented with commercial authorized beta-sitosterol (0.528 g/kg BW, which corresponds to 2× of the recommended human equivalent dose translated to hamster).

Sample C: high-fat diet (60% of calories from fat, D12492, Research diets, USA) supplemented with the cocrystal of beta-sitosterol and propionic acid of the present invention (cocrystal of beta-sitosterol and propionic acid Form 2) (equivalent to 0.264 g of beta-sitosterol/kg BW).

Sample G1: high-fat diet (60% of calories from fat, D12492, Research diets, USA) supplemented with the cocrystal of beta-sitosterol and gallic acid of the present invention (equivalent to 0.158 g of beta-sitosterol/kg BW).

Sample G2: high-fat diet (60% of calories from fat, D12492, Research diets, USA) supplemented with the cocrystal of beta-sitosterol and gallic acid of the present invention (cocrystal of beta-sitosterol and gallic acid Form 5) (equivalent to 0.330 g of beta-sitosterol/kg BW which is approximately 2× of Sample G1).

BW stands for bodyweight 6.2. Animals and Treatment

The animals used in this bioavailability assessment test were Golden Syrian male Hamsters of 8 months of age. Six experimental groups of 8 animals per group were established. The experimental groups were the following:

Comparative group A: fed with the comparative sample A (control);

Comparative group B1: fed with the comparative sample B1 (reference);

Comparative group B2: fed with the comparative sample B2 (reference);

Test group C: fed with Sample C;

Test group G1: fed with Sample G1; and

Test group G2: fed with Sample G2.

The test was performed to animals maintained with ad libitum feeding of each sample during 21 days. In all experimental groups, the diet was supplemented with comparative beta-sitosterol or the crystals of the present invention, in a range dose that goes up to 2 times the dose recommended for human use (2.5 g/day) and adapted for use in hamster (Cf. Reagan-Shaw, et al, "Dose translation from animal to human studies revisited". FASEB J. 2007, vol. 22, pp. 659-661).

6.3. Sampling

After 21 days of feeding with the tested samples, the animals received an intraperitoneal injection of lethal anaesthesia based on the active pentobarbital sodium (lethal dose at 200 mg/mL of pentobarbital, Dolethal, Vetoquinol) under ad libitum feeding conditions. Amounts of administration of the lethal dose of sodium pentobarbital (pre-diluted with saline at 25 mg/mL) were calculated based on the individual weight of each animal.

After verifying that the animal was sedated, it was exsanguinated by making a small incision at the level of the rib cage, followed by collection of blood by cardiac puncture (5 mL syringe with 21 G needles). The interior of the needle and syringe were previously soaked with filtered EDTA (0.5M, pH=8) to prevent blood clotting. Blood was centrifuged at 1000 g for 10 minutes at 4° C. to obtain the plasma, which was frozen at −80° C. until use.

6.4. Determinations

Determination of phytosterols in plasma was performed after saponification and derivatization by gas chromatography (GC-7890A, Agilent Technologies) combined with ionisable flame detector (GS-FID using a HP-5MS column (length 30 m, diameter 0.25 mm) and a helium mobile phase flow of 0.8 mL·min-1. (Cf. Garcia-Llatas, G. et al. "Simultaneous quantification of serum phytosterols and cholesterol precursors using a simple gas chromatographic method". European Journal of Lipid Science and Technology, 2012, vol 114(5), pp. 520-526; and Andrade, I. et al. "Advances in analytical methods to study cholesterol metabolism: the determination of serum noncholesterol sterols". Biomedical Chromatography, 2013, vol. 27(10), pp. 1234-1242).

6.5. Statistical Analysis

Data results were presented as the mean±standard error of mean (SEM). Statistical analysis was performed using IBM SPSS Statistics 24.0 (Chicago, Ill., USA). The comparison between groups was performed by analysis of variance (ANOVA one-way) followed by Fisher's post-hoc analysis (LSD, of the least significant difference). Student's t test was also used to make single comparison between 2 groups. The level of significance was set at $p \leq 0.05$.

6.6. Results

6.6.1. Sitosterolemia

Concerning the impact of treatments on sitosterolemia, data are shown as the ratio of variation respect to the control group (comparative group A), which was set to 1. Administration of an oral dose of commercial beta-sitosterol during 21 days resulted in increased circulating levels of the compound at both doses, showing a dose-dependent response; the administration of reference sample B1 resulted in a Fold-change (FC) of increase of 2.4 with respect to controls (comparative group A), and the administration of reference sample B2 resulted in a FC of increase of 5.3 with respect to controls (comparative group A). The administration of the cocrystal of beta-sitosterol and propionic acid of the present invention (test sample C) and the cocrystal of beta-sitosterol and gallic acid of the present invention (test samples G1 and G2) also promoted an increase in the circulating levels of beta-sitosterol, FC of increase of 6.4, 4.7 and 7.9 respectively, with respect to the comparative group A.

Nevertheless, a significantly marked effect in increasing the circulating levels of beta-sitosterol for cocrystal of beta-sitosterol and propionic acid of the present invention (test sample C) was observed in comparison to the reference group treated with the same dose of commercial beta-sitosterol (comparative group B1). Particularly, a FC increment of 2.7 in relation to reference sample B1 value was observed ($p=0.0126$ vs comparative sample B1, Student t test).

7. Particle Size Test

This test provides the particle size of the co-crystals of the present invention in comparison with the comparaitive Standard sample of beta-Sitosterol from the Ph. Eu. Reference Standard, ref. (Y0001615)

7.1. Tested Samples

Comparative sample A: comparaitive Standard sample of beta-Sitosterol from the Ph. Eu. Reference Standard, ref. (Y0001615)

Sample A: hydrate crystal of beta-sitosterol having 1.25 molecules of water of the present invention Sample B: cocrystal of beta-sitosterol and gallic acid Form 5 of the present invention Sample C: cocrystal of beta-sitosterol and propionic acid Form 2 of the present invention

7.2. Method

The particle size was performed by laser diffraction. For this purpose, a Beckman-Coulter model. LS13320 laser diffractometer (Fullerton, Calif., USA) was equipped with a Micro. Liquid Module (MLM) wet dispersion modul, an an optic model (Fraunhofer. Rdf, PIDS). The measurement range is 0.4-2000 μm.

7.3. Results

Table below shows the mean, the surface weighted mean diameter (D(3,2)), the standard deviation (S.D) and the D10, D50 and D90 of the tested samples.

| Samples | Mean (μm) | D(3, 2) (μm) | S.D. (μm) | D10 (μm) | D50 (μm) | D90 (μm) |
|---|---|---|---|---|---|---|
| Comparative sample A | 109.9 | 30.19 | 51.24 | 44.62 | 108.0 | 178.8 |
| Sample C | 27.77 | 13.19 | 14.82 | 6.671 | 28.01 | 47.60 |
| Sample B | 12.05 | 6.009 | 8.504 | 3.102 | 10.24 | 23.21 |
| Sample A | 18.12 | 8.558 | 11.29 | 4.145 | 16.39 | 34.63 |

The above mentioned results show that the particle size of the co-crystals of beta-sitosterol of the present invention is smaller than the beta-sitosterol.

CITATION LIST

1. Leena I. Christiansen et al. "A novel method of producing a microcrystalline beta-sitosterol suspension in oil" European Journal of Pharmaceutical Sciences, 2002, vol. 15, pp. 261-269.
2. L. Christiansen et al. "Effect of beta-sitosterol on precipitation of cholesterol from non-aqueous and aqueous solutions", International Journal of Pharmaceutics, 2003, vol. 254, pp. 155-166.
3. Anna von Bonsdorff-Nikander et al. "Physical changes of beta-sitosterol crystals in oily suspensions during heating" MPS Pharm. Sci. Tech. 2005, vol 6(3) article 51.
4. Reagan-Shaw, et al, "Dose translation from animal to human studies revisited". FASEB J. 2007, vol. 22, pp. 659-661.
5. Garcia-Llatas, G. et al. "Simultaneous quantification of serum phytosterols and cholesterol precursors using a simple gas chromatographic method". European Journal of Lipid Science and Technology, 2012, vol 114(5), pp. 520-526.
6. Andrade, I. et al. "Advances in analytical methods to study cholesterol metabolism: the determination of serum noncholesterol sterols". Biomedical Chromatography, 2013, vol. 27(10), pp. 1234-1242.
7. Evelyn Moreno-Calvo, et al. "A New Microcrystalline Phytosterol Polymorph Generated Using CO2-Expanded Solvents". Cryst. Growth. & Design., 2014, vol. 14, pp. 58-688.
8. Argay et al. "Crystal structure of stigmast-5-en-3β-ol monohydrate, $C_{29}H_{52}O_2$". Zeitschrift für Kristallographie, 1996, vol. 211(10), pp. 725-727.
9. Reagan-Shaw, et al, "Dose translation from animal to human studies revisited". FASEB J. 2007, vol. 22, pp. 659-661.
10. Garcia-Llatas, G. et al. "Simultaneous quantification of serum phytosterols and cholesterol precursors using a simple gas chromatographic method". European Journal of Lipid Science and Technology, 2012, vol 114(5), pp. 520-526.
11. Andrade, I. et al. "Advances in analytical methods to study cholesterol metabolism: the determination of serum noncholesterol sterols". Biomedical Chromatography, 2013, vol. 27(10), pp. 1234-1242.

The invention claimed is:

1. A cocrystal of beta-sitosterol or a pharmaceutically acceptable ester thereof or an edible acceptable ester thereof and an organic carboxylic acid conformer selected from the group consisting of L-lactic acid, propionic acid, zymonic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acids;
wherein the cocrystal is selected from the group consisting of:
a cocrystal of beta-sitosterol and L-lactic acid monohydrate characterized by having a X-ray diffractogram that comprises characteristic peaks at 2.3 and 4.6±0.3 degrees 2 theta at a Cu-Kα radiation, λ=1.5406 Å;
a cocrystal of beta-sitosterol and zymonic acid monohydrate characterized by having a X-ray diffractogram that comprises characteristic peaks at 2.2 and 4.5±0.3 degrees 2 theta at a Cu-K$_\alpha$ radiation, λ=1.5406 Å;
a cocrystal of beta-sitosterol and gallic acid characterized by having a X-ray diffractogram that comprises characteristic peaks at 7.9 and 16.3±0.3 degrees 2 theta at a Cu-K$_\alpha$, radiation, λ=1.5406 Å;
a cocrystal of beta-sitosterol and 2,4-dihydroxybenzoic acid characterized by having a X-ray diffractogram that comprises characteristic peaks at 11.4 and 16.2±0.3 degrees 2 theta at a Cu-K$_\alpha$ radiation, λ=1.5406 Å;
a cocrystal of beta-sitosterol and 3,4-dihydroxybenzoic acid characterized by having a X-ray diffractogram that comprises characteristic peaks at 2.3 and 15.9±0.3 degrees 2 theta at a Cu-K$_\alpha$ radiation, λ=1.5406 Å;
a cocrystal of beta-sitosterol and 3,5-dihydroxybenzoic acid characterized by having a X-ray diffractogram that comprises characteristic peaks at 10.7 and 15.9±0.3 degrees 2 theta at a Cu-K$_\alpha$ radiation, λ=1.5406 Å;
a cocrystal of beta-sitosterol and 3,5-dihydroxybenzoic acid characterized by having a X-ray diffractogram that comprises characteristic peaks at 2.3 and 4.6±0.3 degrees 2 theta at a Cu-K$_\alpha$ radiation, λ=1.5406 Å;
a cocrystal of beta-sitosterol and 3-hydroxybenzoic acid characterized by having a X-ray diffractogram that comprises characteristic peaks at 4.6 and 12.9±0.3 degrees 2 theta at a Cu-K$_\alpha$, radiation, λ=1.5406 Å;
a cocrystal of beta-sitosterol and 4-hydroxybenzoic acid characterized by having a X-ray diffractogram that comprises characteristic peaks at 6.6 and 13.5±0.3 degrees 2 theta at a Cu-K$_\alpha$ radiation, λ=1.5406 Å;
a cocrystal of beta-sitosterol and 4-hydroxybenzoic acid characterized by having a X-ray diffractogram that comprises characteristic peaks at 15.8 and 17.9±0.3 degrees 2 theta at a Cu-K$_\alpha$ radiation, λ=1.5406 Å; and
a cocrystal of beta-sitosterol and propionic acid that is a hydrate form characterized by having a X-ray diffractogram that comprises characteristic peaks at 3.2 and 4.7±0.3 degrees 2 theta at a Cu-K$_\alpha$ radiation, λ=1.5406 Å.

2. The cocrystal according to claim 1, wherein the organic carboxylic acid is selected from the group consisting of L-lactic acid, propionic acid, zymonic acid, and gallic acid.

3. The cocrystal according to claim 1, which is the cocrystal selected from the group consisting of:
the cocrystal of beta-sitosterol and gallic acid characterized by having a X-ray diffractogram that comprises characteristic peaks at 7.9 and 16.3 ±0.3 degrees 2 theta at a Cu-Kα radiation, λ=1.5406 Å; and
the cocrystal of beta-sitosterol and propionic acid that is a hydrate form characterized by having a X-ray diffractogram that comprises characteristic peaks at 3.2 and 4.7 ±0.3 degrees 2 theta at a Cu-Kα radiation, λ=1.5406 Å.

4. A composition comprising an effective amount of the cocrystal of beta-sitosterol as defined in claim 1 together with one or more acceptable excipients or carriers.

5. The cocrystal of beta-sitosterol as defined in claim 1, for use in the prophylaxis and/or treatment of a disease or condition which involves an alteration of lipid metabolism, circulating levels of lipids in the blood and/or lipid composition in tissues and organs.

6. The cocrystal according to claim 1, wherein the cocrystal is an hydrate crystal form characterized by having a X-ray diffractogram that comprises characteristic peaks at 3.2 and 4.7 ±0.3 degrees 2 theta at a Cu-Kα radiation, λ=1.5406 Å; and wherein the cocrystal is obtainable by a process which comprises:
(a'''') mixing the beta-sitosterol with a water-miscible organic solvent in the presence of propionic acid; and
(b'''') isolating the cocrystal thus obtained.

7. The cocrystal according to claim 1, wherein the organic carboxylic acid is selected from the group consisting of L-lactic acid, zymonic acid, gallic acid, 2,4-dihydroxybenzoic acid, 3,4-dihydroxybenzoic acid, 3-hydroxybenzoic acid, 4-hydroxybenzoic acid and 3,5-dihydroxybenzoic acid.

8. The cocrystal according to claim 1, wherein the organic carboxylic acid is selected from the group consisting of L-lactic acid, zymonic acid, and gallic acid.

* * * * *